(12) United States Patent
Zhang et al.

(10) Patent No.: US 12,331,350 B2
(45) Date of Patent: Jun. 17, 2025

(54) SYSTEMS AND METHODS FOR ALLELE ENRICHMENT USING MULTIPLEXED BLOCKER DISPLACEMENT AMPLIFICATION

(71) Applicant: William Marsh Rice University, Houston, TX (US)

(72) Inventors: David Yu Zhang, Houston, TX (US); Ping Song, Houston, TX (US); Xi Chen, Houston, TX (US)

(73) Assignee: William Marsh Rice University, Houston, TX (US)

( * ) Notice: Subject to any disclaimer, the term of this patent is extended or adjusted under 35 U.S.C. 154(b) by 1184 days.

(21) Appl. No.: 16/971,411

(22) PCT Filed: Feb. 20, 2019

(86) PCT No.: PCT/US2019/018690
§ 371 (c)(1),
(2) Date: Aug. 20, 2020

(87) PCT Pub. No.: WO2019/164885
PCT Pub. Date: Aug. 29, 2019

(65) Prior Publication Data
US 2021/0024989 A1  Jan. 28, 2021

Related U.S. Application Data

(60) Provisional application No. 62/649,138, filed on Mar. 28, 2018, provisional application No. 62/632,712, filed on Feb. 20, 2018.

(51) Int. Cl.
*C12Q 1/6858* (2018.01)

(52) U.S. Cl.
CPC .................. *C12Q 1/6858* (2013.01)

(58) Field of Classification Search
None
See application file for complete search history.

(56) References Cited

U.S. PATENT DOCUMENTS

| | | | |
|---|---|---|---|
| 5,891,625 A | 4/1999 | Buchardt et al. | |
| 7,157,228 B2 | 1/2007 | Hashmi et al. | |
| 8,329,397 B2 | 12/2012 | West et al. | |
| 2003/0096277 A1 | 5/2003 | Chen | |
| 2009/0023597 A1 | 1/2009 | Wong et al. | |
| 2009/0053720 A1 | 2/2009 | Newton | |
| 2010/0009355 A1 | 1/2010 | Kolodney | |
| 2010/0285478 A1 | 11/2010 | Chen et al. | |
| 2013/0149695 A1 | 6/2013 | Lee et al. | |
| 2014/0017685 A1 | 1/2014 | Fu | |
| 2017/0067090 A1 | 3/2017 | Zhang et al. | |
| 2017/0327868 A1 | 11/2017 | Huang et al. | |
| 2022/0090168 A1 | 3/2022 | Zhang et al. | |

FOREIGN PATENT DOCUMENTS

| | | | |
|---|---|---|---|
| CN | 102321741 A1 | 1/2012 | |
| CN | 102776291 B1 | 12/2014 | |
| RU | 2485046 C2 | 6/2013 | |
| WO | WO 2011/146403 | 11/2011 | |
| WO | WO 2012/151560 | 11/2012 | |
| WO | WO 2013/097173 | 7/2013 | |
| WO | WO 2014/177540 | 11/2014 | |
| WO | WO/2015/179339 | 11/2015 | |
| WO | WO-2015179339 A1 * | 11/2015 | ............. C07H 21/04 |

OTHER PUBLICATIONS

Wu et al., "Multiplexed enrichment of rare DNA variants via sequence-selective and temperature-robust amplification," Nat. Biomed. Eng. 2017, 1:714-723, published online Sep. 4, 2017. (Year: 2017).*
Anithakumari et al. "A pipeline for high throughput detection and mapping of SNPs from EST databases", Mol. Breeding, 26:65-75, 2010.
Bonnet et al., "Thermodynamic basis of the enhanced specificity of structured DNA probes." Proc. Natl. Acad. Sci. USA, 96:6171-6176, 1999.
Breslauer et al., "Predicting DNA duplex stability from the base sequence," PNAS, 83:3746-3750, 1986.
Huang et al., "Extension of base mispairs by Taq DNA polymerase: implications for single nucleotide discrimination in PCR," Nucl. Acids Res., 20:4567-4573, 1992.
International Search Report and Written Opinion for PCT/US2019/018690, dated May 19, 2019, 13 pages.
Johnson et al., "Eukaryotic polymerases ι and ζ act sequentially to bypass DNA lesions," Nature, 406:1015-1019, 2000.
Kibbe, "OligoCalc: an online oligonucleotide properties calculator," Nucl. Acids Res., 35:W43-46, 2007.
Kim et al., "Detection of DNA hybridization properties using thermodynamic method," Japanese journal of applied physics, 45.1S:509-512, 2006.
Murdock et al., "The age-related accumulation of a mitochondrial DNA control region mutation in muscle, but not brain, detected by a sensitive PNA-directed PCR clamping based method." Nucleic Acids Research, 28:4350-4355, 2000.
Picher et al., "Promiscuous mismatch extension by human DNA polymerase lambda," Nucl. Acids Res., 34:3259-3266, 2006.
SantaLucia et al., "The thermodynamics of DNA structural motifs," Ann. Rev. Biophys. Struct., 33:415-440, 2004.
Sugimoto et al., "Improved thermodynamic parameters and helix initiation factor to predict stability of DNA duplexes," Nucl. Acids Res., 24:4501-4505, 1996.
Supplementary European Search Report for EP 19757198, dated Feb. 23, 2022, 9 pages.

(Continued)

*Primary Examiner* — Kaijiang Zhang
(74) *Attorney, Agent, or Firm* — Parker Highlander PLLC

(57) ABSTRACT

Provided herein are reagents and methods for simultaneously enriching many potential rare genetic variants at different genetic loci. The rare variants enriched can include single nucleotide polymorphisms (SNPs), single nucleotide variants, or small insertions and deletions. Embodiments of the invention include procedures for integration with downstream next generation sequencing (NGS) analysis. Embodiments of the invention include analysis of nonpathogenic SNPs for the determination of cell identity and detection of cell contamination using qPCR or NGS.

12 Claims, 50 Drawing Sheets

Specification includes a Sequence Listing.

(56) References Cited

OTHER PUBLICATIONS

Supplementary Partial European Search Report for EP 19757198, dated Nov. 22, 2021, 45 pages.

Vaisman et al., "Human DNA polymerase iota promiscuous mismatch extension," J. Biol. Chem., 276:30615-30622, 2001.

Vallone & Butler, "AutoDimer: a screening tool for primer-dimer and hairpin structures," Biotechniques, 37.2:226-231, 2004.

Verhasselt et al., "DNA sequencing by a subcloning-walking strategy using a specific and semi-random primer in the polymerase chain reaction," Journal of DNA Sequence; vol. 2, Issue 5 (1992): Abstract.

Vestheim et al., "Blocking primers to enhance PCR amplification of rare sequences in mixed samples—a case study on prey DNA in Antarctic krill stomachs," Front Zool, 5(12):1-11, 2008.

Washington et al., "Human DINB1-encoded DNA polymerase κ is a promiscuous extender of mispaired primer termini," Proc. Natl. Acad. Sci USA, 99:1910-1914, 2002.

Wu et al., "Multiplexed Enrichment of Rare DNA Variants via Sequence-Selective and Temperature-Robust Amplification", Nature Biomedical Engineering, 1:714-723, 2017.

Yu et al., "Specific inhibition of PCR by non-extendable oligonucleotides using a 5' to 3' exonuclease-deficient DNA polymerase," Biotechniques, 23:714-720, 1997.

Zheng et al., "Experimental methods of molecular biology in Chinese and English medicine," Peking Union Medical College Press; 1st Ed. (Mar. 2005).

\* cited by examiner

SNP alleles, if present, enriched to higher VAFs

Library for NGS

*Standard primer dimers*
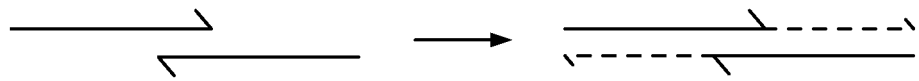
*Primer dimers due to HiFi DNA Pol.*
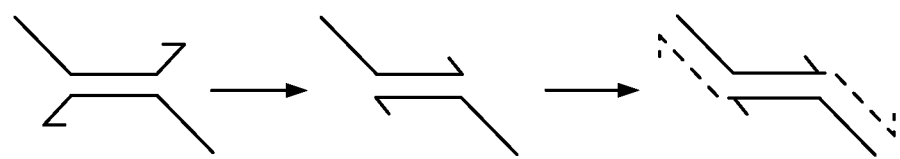
*BDA primer inactivation*
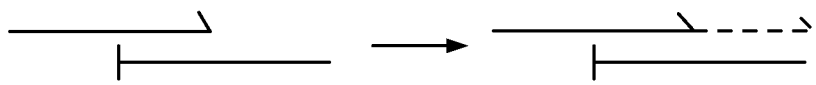
*BDA primer trimers*
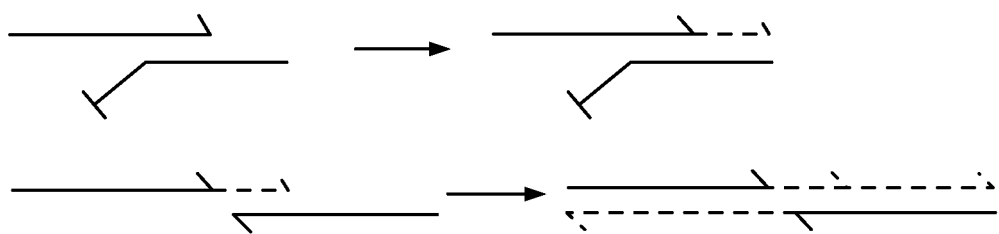
FIG. 5A

*Library for NGS*

CASE 1: Known base genotype;
  unknown contaminant genotype

| Locus: | 1 | 2 | 3 | 4 | 5 |
|---|---|---|---|---|---|
| Base: | A/T | C/C | C/T | G/G | A/A |
| Contaminant: | T/T | C/G | C/T | G/G | T/T |

1. Rule out loci where base allele is heterozygous

2. Design Blockers against base SNP alleles

| Blocker: | | C | | G | A |
| BDA amplicon: | | [G] | | G | [T] |

*Any* SNP alleles in BDA amplicon different from base SNP alleles implies contamination Contamination will lead to lower Ct in qPCR setting

FIG. 8

CASE 2: Known contaminant genotype; unknown base genotype

| Locus: | 1 | 2 | 3 | 4 | 5 |
|---|---|---|---|---|---|
| Base: | A/T | C/C | C/T | G/G | A/A |
| Contaminant: | T/T | C/G | C/T | G/G | T/T |

1. For contaminant homozygous loci, design Blockers against other allele

2. For contaminant hetomozygous loci, design Blockers against either allele

| Blocker: | A | C | C | T | A |
|---|---|---|---|---|---|
| BDA amplicon: | ⊡T | ⊡G | ⊡T | ⊡G | ⊡T |

Contaminant confirmed if <u>all</u> BDA amplicon alleles match contaminant SNP alleles

FIG. 8
*(Cont'd)*

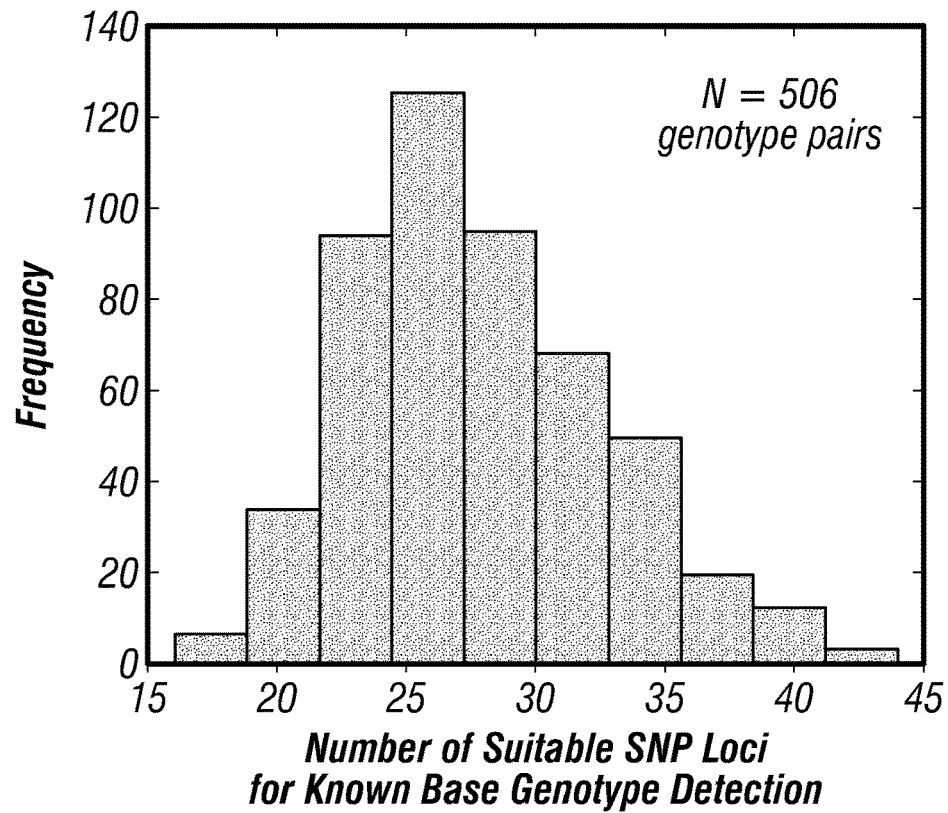
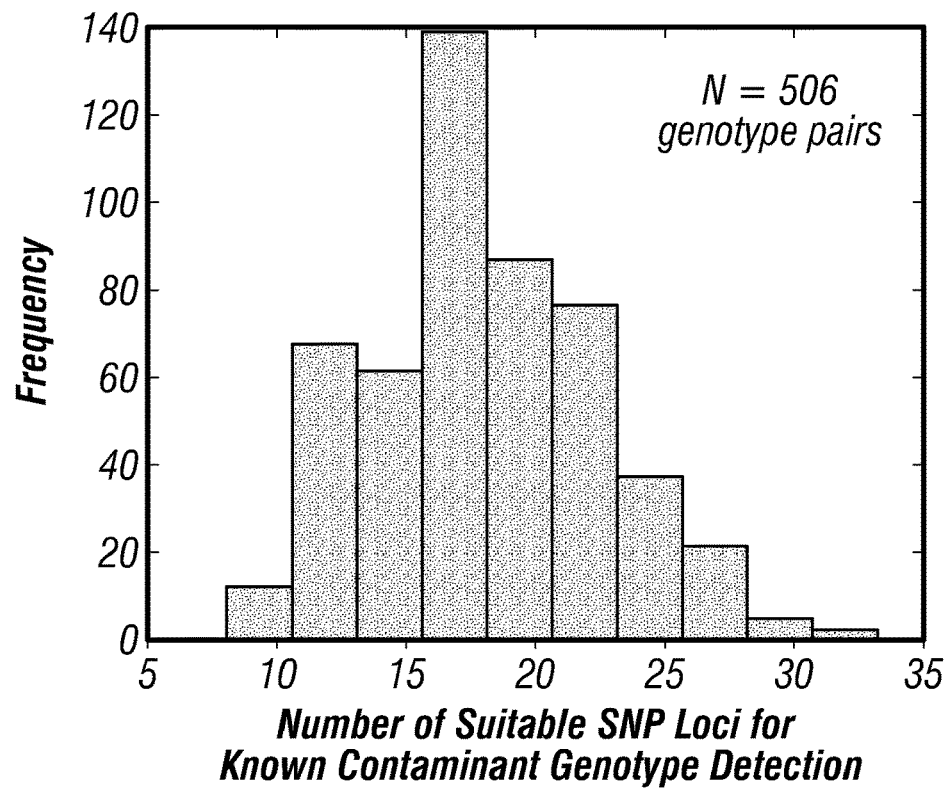
FIG. 9
(Cont'd)

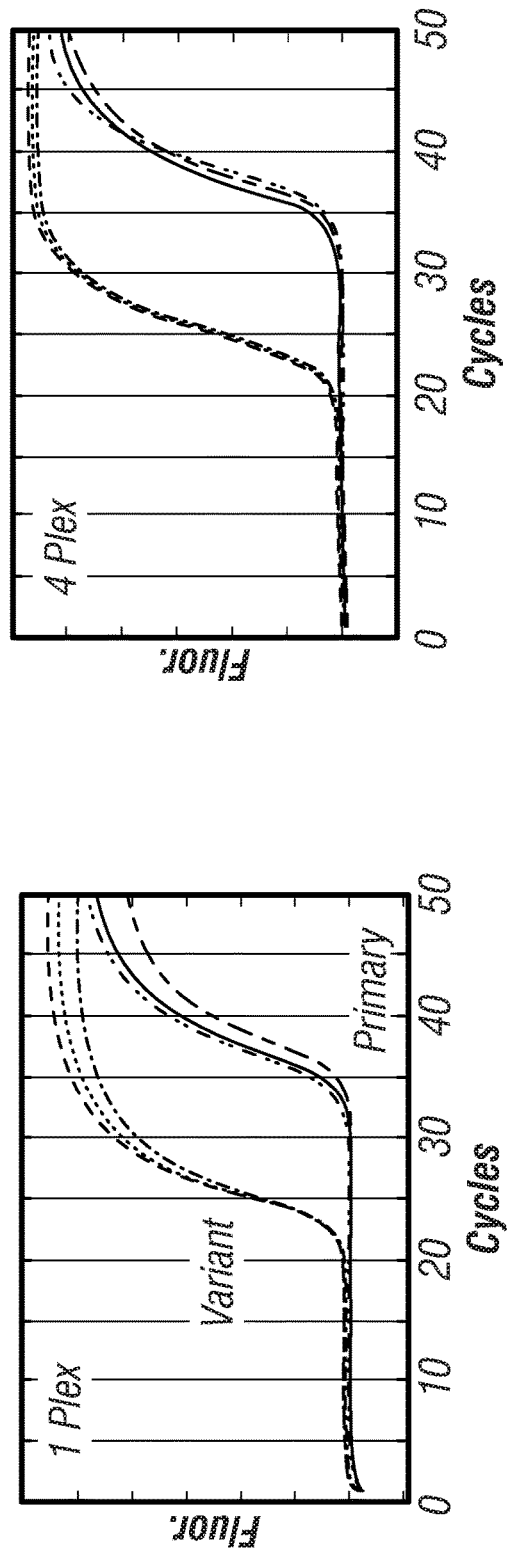
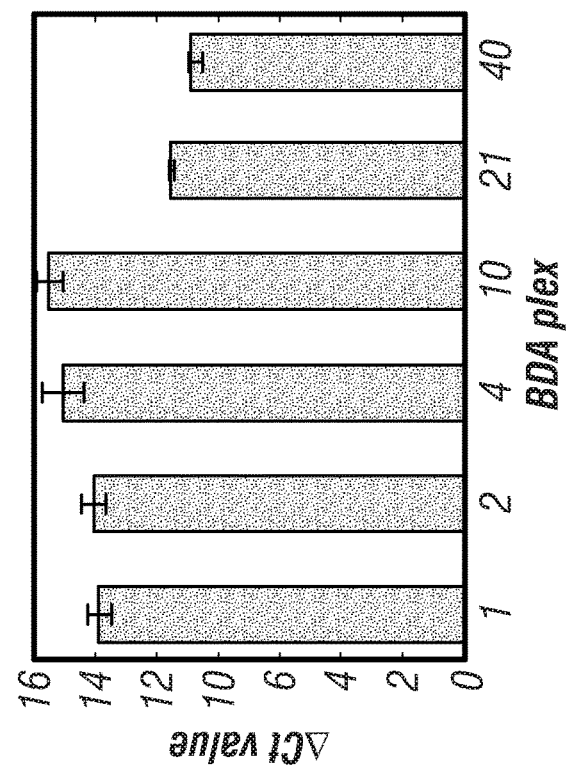
FIG. 11D

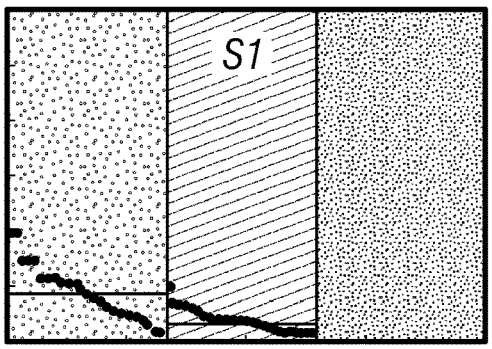
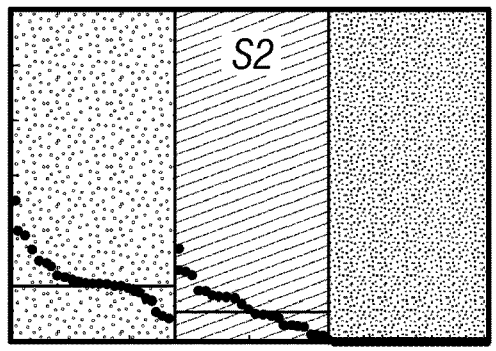
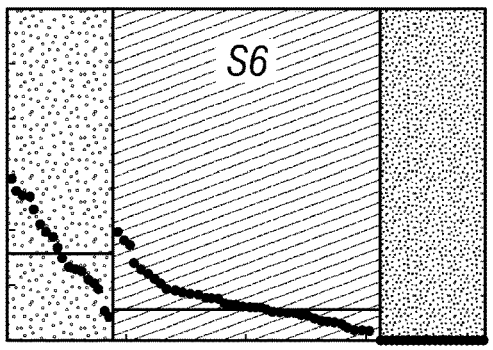
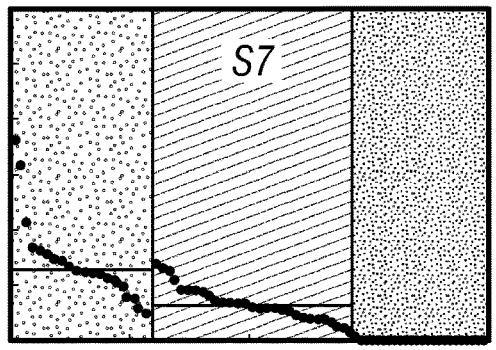
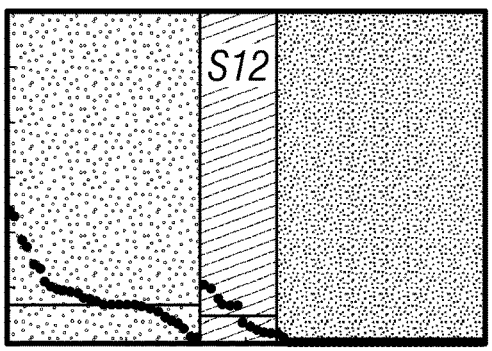
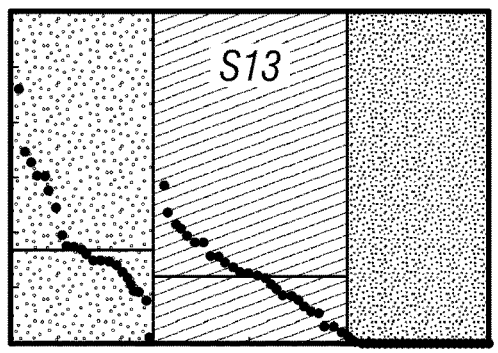
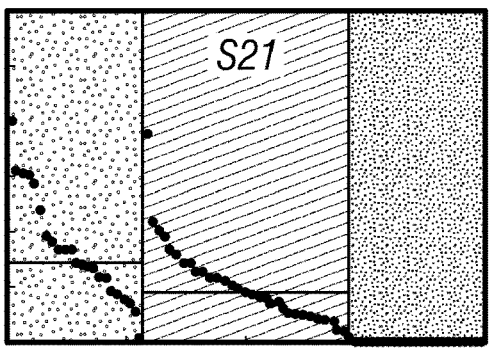
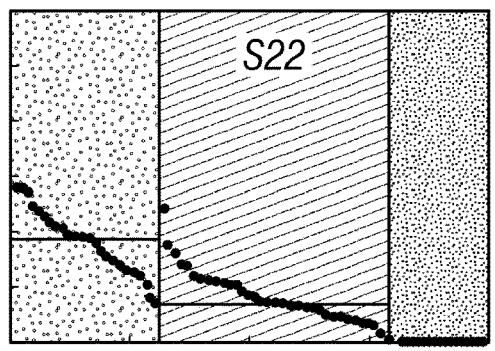
SNPs sorted by contaminant genotype and inferred VAF
FIG. 15A
*(Cont'd)*

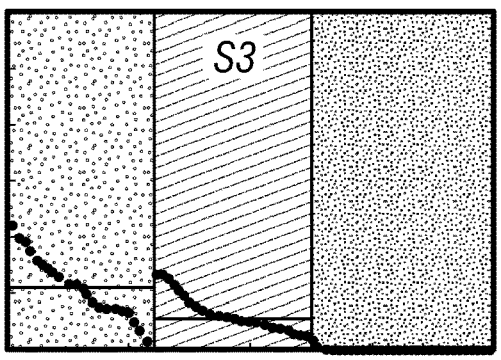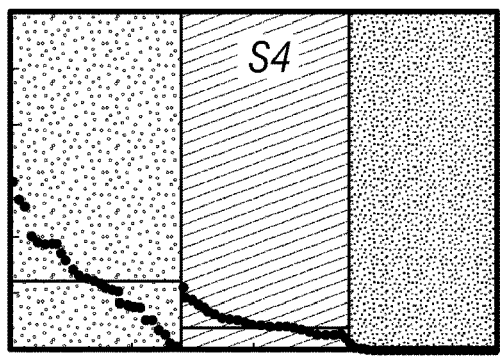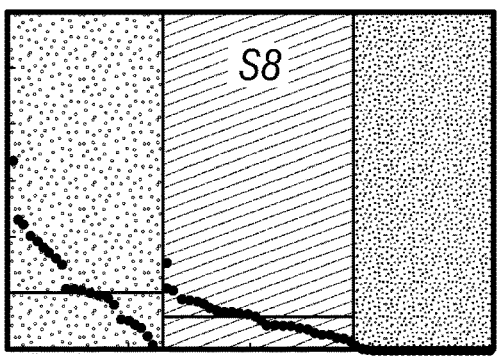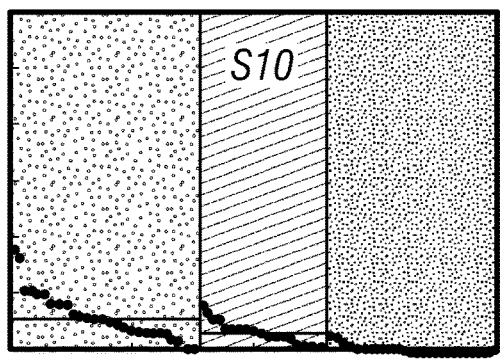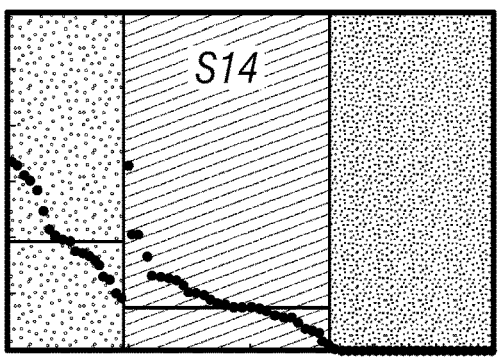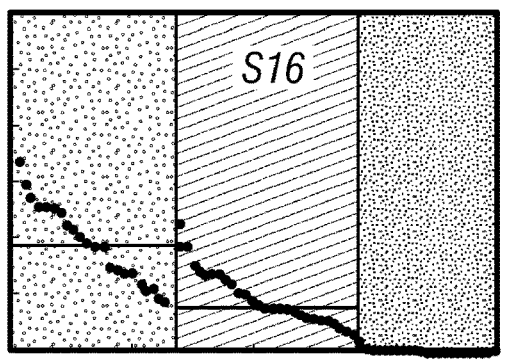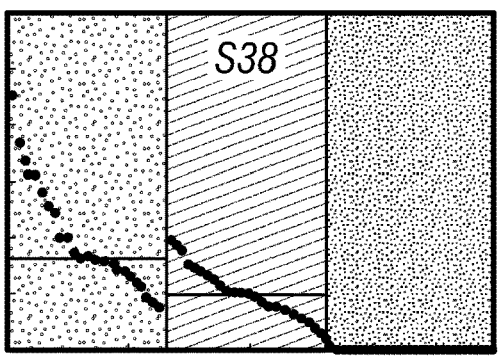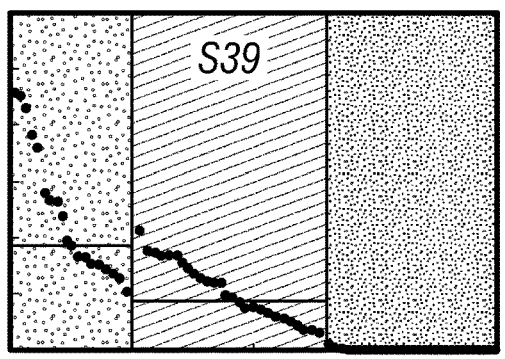
SNPs sorted by contaminant genotype and inferred VAF
FIG. 15A
*(Cont'd)*

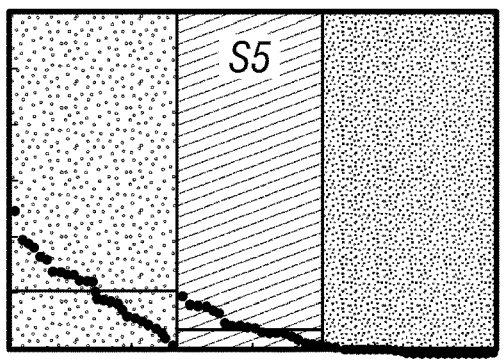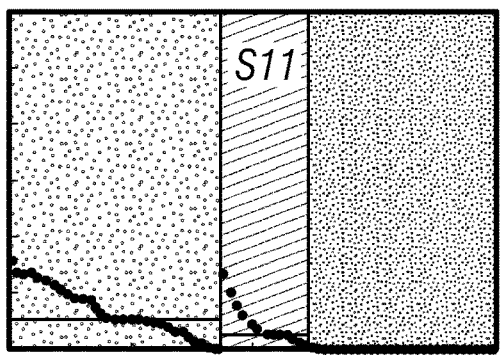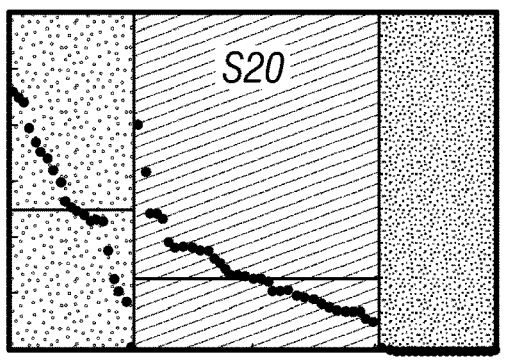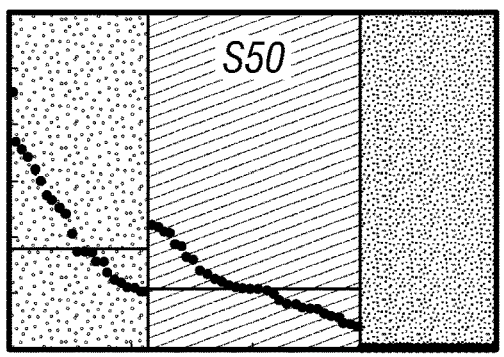
SNPs sorted by contaminant genotype and inferred VAF
*FIG. 15A*
*(Cont'd)*

```
                    SEQUENCE LISTING

<160> NUMBER OF SEQ ID NOS: 252

<210> SEQ ID NO 1
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 1
accaatggga gtcactgctg                                               20

<210> SEQ ID NO 2
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 2
gaggggtatt agaagaatga ctatgtga                                      28

<210> SEQ ID NO 3
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 3
gctcttcctc tcacatcttt atttaacc                                      28

<210> SEQ ID NO 4
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 4
cagagtaaaa tttactgctc cgtcataa                                      28

<210> SEQ ID NO 5
```

```
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 5
ggattcccta agctcttcaa tattgc                                          26

<210> SEQ ID NO 6
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 6
cctcatctgt aaagcaggga gaga                                            24

<210> SEQ ID NO 7
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 7
acttctgcca acattcaaat tcagg                                           25

<210> SEQ ID NO 8
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 8
ggatgggact ccaatgcaaa act                                             23

<210> SEQ ID NO 9
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 9
catcttgctc ttcatagata gcttcaga                                        28

<210> SEQ ID NO 10
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 10
cctgaatgtc agttttgtta gagcaac                                         27

<210> SEQ ID NO 11
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 11
```
cagacttaat caaagcccctt gaaaaga                                      27

<210> SEQ ID NO 12
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 12
cctcccatag tgattcttat gaagtca                                       27

<210> SEQ ID NO 13
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 13
aatgctttgc ttgctgagaa ctt                                           23

<210> SEQ ID NO 14
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 14
aatgggaaaa cacattttaa gggca                                         25

<210> SEQ ID NO 15
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 15
ccacactctg cctctcatgg tat                                           23

<210> SEQ ID NO 16
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 16
acttaagagg tcaacacaga tgaaaattat c                                  31

<210> SEQ ID NO 17
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 17
tccgcaaaac ctacaatctc tgaa                                          24

<210> SEQ ID NO 18
<211> LENGTH: 25
<212> TYPE: DNA

<213> ORGANISM: Artificial Sequence
<220> FEATURE:
<223> OTHER INFORMATION: Synthetic polynucleotide

<400> SEQUENCE: 18
tcagatgctt taggctcatg agtta                                        25

<210> SEQ ID NO 19
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 19
ctccttggaa tcaccaacaa acat                                         24

<210> SEQ ID NO 20
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 20
cttgtatata gacggtaaaa taaacaccaa ga                                32

<210> SEQ ID NO 21
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 21
tgaagcagat gttgaacaac aagg                                         24

<210> SEQ ID NO 22
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 22
ttcctgcttc cagacatgaa tca                                          23

<210> SEQ ID NO 23
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 23
acccaggtga gttttgtttc acat                                         24

<210> SEQ ID NO 24
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 24
ctctctgcct gcaggatgtg                                              20

<210> SEQ ID NO 25
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 25
cacttcctcc agaaggtcca aag                                           23

<210> SEQ ID NO 26
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 26
actaagagtg cagagcctgg aa                                            22

<210> SEQ ID NO 27
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 27
gcgttgtgct gtccattgg                                                19

<210> SEQ ID NO 28
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 28
gggttaaaat cttttgcttt catattgagc                                    30

<210> SEQ ID NO 29
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 29
cccgttatat aagaggacat aattgcat                                      28

<210> SEQ ID NO 30
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 30
cactttatca gacacagtta tgtgct                                        26

<210> SEQ ID NO 31
<211> LENGTH: 25
<212> TYPE: DNA
<213> ORGANISM: Artificial Sequence
<220> FEATURE:

<223> OTHER INFORMATION: Synthetic polynucleotide

<400> SEQUENCE: 31
gccctatagg ttttcctcct actgt                                               25

<210> SEQ ID NO 32
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 32
ctatctgcag gattgtgttc aatgta                                              26

<210> SEQ ID NO 33
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 33
ctctctagag tgcagattgg tagaa                                               25

<210> SEQ ID NO 34
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 34
caaagttgat aaattaaagg actaaggcac                                          30

<210> SEQ ID NO 35
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 35
ctgacctaag gcatgggact t                                                   21

<210> SEQ ID NO 36
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 36
cattctgtct gggatgaggt gat                                                 23

<210> SEQ ID NO 37
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 37
tggaatcaaa catactatgt gtcaaaca                                            28

```
<210> SEQ ID NO 38
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 38
gcgaagtcat tcggtcctc tttaa                                              25

<210> SEQ ID NO 39
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 39
cctctgattc ccagacataa tgct                                              24

<210> SEQ ID NO 40
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 40
tgaaagacgt cacagcaagg t                                                 21

<210> SEQ ID NO 41
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 41
tgtaggagag attgggctag agag                                              24

<210> SEQ ID NO 42
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 42
acagaaacca attacctatg aggagtaa                                          28

<210> SEQ ID NO 43
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 43
gaaagtggca cagaaactca gac                                               23

<210> SEQ ID NO 44
<211> LENGTH: 31
<212> TYPE: DNA
<213> ORGANISM: Artificial Sequence
<220> FEATURE:
<223> OTHER INFORMATION: Synthetic polynucleotide
```

```
<400> SEQUENCE: 44
gcattagatc atttaacaca caaaaccta t                              31

<210> SEQ ID NO 45
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 45
tgctcctaaa agcacccagc                                          20

<210> SEQ ID NO 46
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 46
ctaacttcct aactaaaact ttacagtgga                               30

<210> SEQ ID NO 47
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 47
ggatttcaca cccattagaa taactactat                               30

<210> SEQ ID NO 48
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 48
cctctagaaa aaatggagat ttgggaat                                 28

<210> SEQ ID NO 49
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 49
ggactttttt gcttttgac acctttac                                  28

<210> SEQ ID NO 50
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 50
acgtatttct aactatagtg agtgcattat g                             31

<210> SEQ ID NO 51
<211> LENGTH: 25
```

<212> TYPE: DNA
<213> ORGANISM: Artificial Sequence
<220> FEATURE:
<223> OTHER INFORMATION: Synthetic polynucleotide

<400> SEQUENCE: 51
acatgtccaa agagagaagt cgtag                                   25

<210> SEQ ID NO 52
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 52
gcacgtagat gaaattgccc cata                                    24

<210> SEQ ID NO 53
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 53
gccccaaagg ttaccccatg                                         20

<210> SEQ ID NO 54
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 54
gtagccgctt ctctgtgagt t                                       21

<210> SEQ ID NO 55
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 55
ggaaaatatg tctaaaaagg ctctggag                                28

<210> SEQ ID NO 56
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 56
gtttgttcta aggttcatct ggtgat                                  26

<210> SEQ ID NO 57
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 57

```
gtgggcttac atgattggat taactt                                           26
```

<210> SEQ ID NO 58
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 58

```
tgtcccactt tttacctccc ttc                                              23
```

<210> SEQ ID NO 59
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 59

```
gggcttcgga atcggacttg                                                  20
```

<210> SEQ ID NO 60
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 60

```
tgtgctacga cagagctaag tac                                              23
```

<210> SEQ ID NO 61
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 61

```
ccccggatgt cagggaatg                                                   19
```

<210> SEQ ID NO 62
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 62

```
ccaggcacca ctgctttgt                                                   19
```

<210> SEQ ID NO 63
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 63

```
gcagaaaaaa atgatatctg aattctggat                                       30
```

<210> SEQ ID NO 64
<211> LENGTH: 31
<212> TYPE: DNA
<213> ORGANISM: Artificial Sequence

```
<220> FEATURE:
<223> OTHER INFORMATION: Synthetic polynucleotide

<400> SEQUENCE: 64 ccttttcac tgttatgaaa tgtactttct t                              31

<210> SEQ ID NO 65
<211> LENGTH: 17
<212> TYPE: DNA
<213> ORGANISM: Artificial Sequence
<220> FEATURE:
<223> OTHER INFORMATION: Synthetic polynucleotide

<400> SEQUENCE: 65
aggatgctgg ggcttgc                                             17

<210> SEQ ID NO 66
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 66
gtaaagtgca tggggtcaag tc                                       22

<210> SEQ ID NO 67
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 67
tgagaagtct aacaagttaa attcaggac                                29

<210> SEQ ID NO 68
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 68
ggtagaatgt tagtgactat gtacaatttc a                             31

<210> SEQ ID NO 69
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 69
accttgtcaa gaacctaaat agtgagaa                                 28

<210> SEQ ID NO 70
<211> LENGTH: 30
<212> TYPE: DNA
<213> ORGANISM: Artificial Sequence
<220> FEATURE:
<223> OTHER INFORMATION: Synthetic polynucleotide

<400> SEQUENCE: 70
cgtgggctag tcaagaatat aaaatgttag                               30
```

<210> SEQ ID NO 71
<211> LENGTH: 37
<212> TYPE: DNA
<213> ORGANISM: Artificial Sequence
<220> FEATURE:
<223> OTHER INFORMATION: Synthetic polynucleotide

<400> SEQUENCE: 71
cctatataga ctaatttact taaacattta aacccca          37

<210> SEQ ID NO 72
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 72
ggttcaactc tcagttttat tagttgtgt                   29

<210> SEQ ID NO 73
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 73
agcatcgtga ggttctgaaa aga                         23

<210> SEQ ID NO 74
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 74
cctaacacca gttcttcctc cac                         23

<210> SEQ ID NO 75
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 75
tgtgtggctc agtataccac ttag                        24

<210> SEQ ID NO 76
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 76
gaaaaaaaag ggtctcatta ggaatcatta c                31

<210> SEQ ID NO 77
<211> LENGTH: 30
<212> TYPE: DNA
<213> ORGANISM: Artificial Sequence
<220> FEATURE:
<223> OTHER INFORMATION: Synthetic polynucleotide

```
<400> SEQUENCE: 77
gtttttatat gttagtgtcc ccatggtata                                    30

<210> SEQ ID NO 78
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 78
agtgatcaga aggctttgat ttga                                          24

<210> SEQ ID NO 79
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 79
gcacatcata cattatttct gttgctat                                      28

<210> SEQ ID NO 80
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 80
gaaatattgc tggggtcagc g                                             21

<210> SEQ ID NO 81
<211> LENGTH: 23
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (20)..(21)
<223> OTHER INFORMATION: n = any nucleotide, present or absent

<400> SEQUENCE: 81
actgctgcag gcgccctgtn ntc                                           23

<210> SEQ ID NO 82
<211> LENGTH: 42
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(40)
<223> OTHER INFORMATION: n = any nucleotide, present or absent

<400> SEQUENCE: 82
gactatgtga caaaatagct aaggatacag gaaatatgnn ga                      42

<210> SEQ ID NO 83
<211> LENGTH: 42
<212> TYPE: DNA
<213> ORGANISM: Artificial Sequence
<220> FEATURE:
```

<223> OTHER INFORMATION: Synthetic polynucleotide
<220> FEATURE:
<221> NAME/KEY: misc_feature
<222> LOCATION: (39)..(40)
<223> OTHER INFORMATION: n = any nucleotide, present or absent

<400> SEQUENCE: 83
catctttatt taacccatta gaaaatccta tcagctctnn cg                              42

<210> SEQ ID NO 84
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (35)..(36)
<223> OTHER INFORMATION: n = any nucleotide, present or absent

<400> SEQUENCE: 84
ccgtcataac aaaaacatat ttactttctc tggcnncc                                  38

<210> SEQ ID NO 85
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (30)..(31)
<223> OTHER INFORMATION: n = any nucleotide, present or absent

<400> SEQUENCE: 85
cttcaatatt gcagaagtgt tgcaagcctn ngt                                       33

<210> SEQ ID NO 86
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(38)
<223> OTHER INFORMATION: n = any nucleotide, present or absent

<400> SEQUENCE: 86
agggagagaa cctcctccct cacaganntc                                           30

<210> SEQ ID NO 87
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (33)..(34)
<223> OTHER INFORMATION: n = any nucleotide, present or absent

<400> SEQUENCE: 87
tcaaattcag gtaccttaga gggacagcta aannct                                    36

<210> SEQ ID NO 88
<211> LENGTH: 37
<212> TYPE: DNA
<213> ORGANISM: Artificial Sequence

```
<220> FEATURE:
<223> OTHER INFORMATION: Synthetic polynucleotide
<220> FEATURE:
<221> NAME/KEY: misc_feature
<222> LOCATION: (34)..(35)
<223> OTHER INFORMATION: n = any nucleotide, present or absent

<400> SEQUENCE: 88
aatgcaaaac tcaatgtatc agtgtgagga tgtnnat                              37

<210> SEQ ID NO 89
<211> LENGTH: 35
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (32)..(33)
<223> OTHER INFORMATION: n = any nucleotide, present or absent

<400> SEQUENCE: 89
tagcttcaga acattccag tgtatgtgca gnnga                                 35

<210> SEQ ID NO 90
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (33)..(34)
<223> OTHER INFORMATION: n = any nucleotide, present or absent

<400> SEQUENCE: 90
gttagagcaa ctttccttga ttcccagagt agnnct                               36

<210> SEQ ID NO 91
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (31)..(32)
<223> OTHER INFORMATION: n = any nucleotide, present or absent

<400> SEQUENCE: 91
ccttgaaaag agggcttagg ttttctttgc nnta                                 34

<210> SEQ ID NO 92
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (38)..(39)
<223> OTHER INFORMATION: n = any nucleotide, present or absent

<400> SEQUENCE: 92
cttatgaagt catggaacaa tgcctacttc tatatttnna g                         41

<210> SEQ ID NO 93
<211> LENGTH: 42
<212> TYPE: DNA
```

<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (39)..(40)
<223> OTHER INFORMATION: n = any nucleotide, present or absent

<400> SEQUENCE: 93
ctgagaactt agcattaatt acctttttc atgagaatnn ta         42

<210> SEQ ID NO 94
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (35)..(36)
<223> OTHER INFORMATION: n = any nucleotide, present or absent

<400> SEQUENCE: 94
agggcatttt ttacagtgtt gaatattgaa actgnntg            38

<210> SEQ ID NO 95
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (31)..(32)
<223> OTHER INFORMATION: n = any nucleotide, present or absent

<400> SEQUENCE: 95
ctctcatggt atggtgtttt tctgtgctcc nncg                34

<210> SEQ ID NO 96
<211> LENGTH: 45
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (42)..(43)
<223> OTHER INFORMATION: n = any nucleotide, present or absent

<400> SEQUENCE: 96
cagatgaaaa ttatctgtgc tttttgtaa gctgatatat tnntc      45

<210> SEQ ID NO 97
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (37)..(38)
<223> OTHER INFORMATION: n = any nucleotide, present or absent

<400> SEQUENCE: 97
caatctctga atctcagaat agtagcctag aaaacgnngc           40

<210> SEQ ID NO 98
<211> LENGTH: 39

```
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (36)..(37)
<223> OTHER INFORMATION: n = any nucleotide, present or absent

<400> SEQUENCE: 98
ctcatgagtt aacaaggaga tgatgtagtg taaagnngc                       39

<210> SEQ ID NO 99
<211> LENGTH: 32
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (29)..(30)
<223> OTHER INFORMATION: n = any nucleotide, present or absent

<400> SEQUENCE: 99
caacaaacat gccttctcct tctcctgann aa                              32

<210> SEQ ID NO 100
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(35)
<223> OTHER INFORMATION: n = any nucleotide, present or absent

<400> SEQUENCE: 100
taaacaccaa gacgtggtaa atatttacct ggtnncg                         37

<210> SEQ ID NO 101
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (31)..(32)
<223> OTHER INFORMATION: n = any nucleotide, present or absent

<400> SEQUENCE: 101
caacaaggtc agtattgata agtggttgct nnag                            34

<210> SEQ ID NO 102
<211> LENGTH: 35
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (32)..(33)
<223> OTHER INFORMATION: n = any nucleotide, present or absent

<400> SEQUENCE: 102
acatgaatca tgtcactatt caatgggatg cnntt                           35

<210> SEQ ID NO 103
```

```
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (36)..(37)
<223> OTHER INFORMATION: n = any nucleotide, present or absent

<400> SEQUENCE: 103
ttttgtttca catgataacc atatcactgg acacanncc                                39

<210> SEQ ID NO 104
<211> LENGTH: 25
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (22)..(23)
<223> OTHER INFORMATION: n = any nucleotide, present or absent

<400> SEQUENCE: 104
aggatgtgcg acgtgtgcct gnngg                                              25

<210> SEQ ID NO 105
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(26)
<223> OTHER INFORMATION: n = any nucleotide, present or absent

<400> SEQUENCE: 105
ggtccaaagc cggaagggcc taaannaa                                           28

<210> SEQ ID NO 106
<211> LENGTH: 26
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (23)..(24)
<223> OTHER INFORMATION: n = any nucleotide, present or absent

<400> SEQUENCE: 106
gcctggaacc gagacgcctc agnntg                                             26

<210> SEQ ID NO 107
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(26)
<223> OTHER INFORMATION: n = any nucleotide, present or absent

<400> SEQUENCE: 107
tccattggct actcagtctc ggctnnat                                           28
```

```
<210> SEQ ID NO 108
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (35)..(36)
<223> OTHER INFORMATION: n = any nucleotide, present or absent

<400> SEQUENCE: 108
tcatattgag cttaagagtt cagaacactg atggnnat                              38

<210> SEQ ID NO 109
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(35)
<223> OTHER INFORMATION: n = any nucleotide, present or absent

<400> SEQUENCE: 109
cataattgca tataacctac acacattctc ccanntt                               37

<210> SEQ ID NO 110
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(35)
<223> OTHER INFORMATION: n = any nucleotide, present or absent

<400> SEQUENCE: 110
gttatgtgct ggaaagagca taaattttgg aatnnaa                               37

<210> SEQ ID NO 111
<211> LENGTH: 47
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (44)..(45)
<223> OTHER INFORMATION: n = any nucleotide, present or absent

<400> SEQUENCE: 111
ctcctactgt acatacatat tatcttaagg aaaaaatcca aatnnat                    47

<210> SEQ ID NO 112
<211> LENGTH: 47
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (44)..(45)
<223> OTHER INFORMATION: n = any nucleotide, present or absent

<400> SEQUENCE: 112
tgttcaatgt attaaataat catcagcata tttttgtatt cacnnaa                    47
```

```
<210> SEQ ID NO 113
<211> LENGTH: 35
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (32)..(33)
<223> OTHER INFORMATION: n = any nucleotide, present or absent

<400> SEQUENCE: 113
gattggtaga agacactgat tgcatcttca anngt                          35

<210> SEQ ID NO 114
<211> LENGTH: 31
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(29)
<223> OTHER INFORMATION: n = any nucleotide, present or absent

<400> SEQUENCE: 114
aaggcacaga acaatcatgc aacttgcnna t                              31

<210> SEQ ID NO 115
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (26)..(27)
<223> OTHER INFORMATION: n = any nucleotide, present or absent

<400> SEQUENCE: 115
gggactttct tgagggatgg catccnnct                                 29

<210> SEQ ID NO 116
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (33)..(34)
<223> OTHER INFORMATION: n = any nucleotide, present or absent

<400> SEQUENCE: 116
gaggtgatat ctcatttggg cttctatttg cannta                         36

<210> SEQ ID NO 117
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(26)
<223> OTHER INFORMATION: n = any nucleotide, present or absent

<400> SEQUENCE: 117
tgtcaaacac ccatgctcac ccttnnca                                  28
```

<210> SEQ ID NO 118
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(35)
<223> OTHER INFORMATION: n = any nucleotide, present or absent

<400> SEQUENCE: 118
ggtcctcttt aaggtctcta caataaattg ccannaa                               37

<210> SEQ ID NO 119
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(35)
<223> OTHER INFORMATION: n = any nucleotide, present or absent

<400> SEQUENCE: 119
gacataatgc ttttggttgg actttcaaaa aggnngt                               37

<210> SEQ ID NO 120
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (33)..(34)
<223> OTHER INFORMATION: n = any nucleotide, present or absent

<400> SEQUENCE: 120
gcaaggttca aatcattctc tcctatctca tcnntt                                36

<210> SEQ ID NO 121
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (36)..(37)
<223> OTHER INFORMATION: n = any nucleotide, present or absent

<400> SEQUENCE: 121
gctagagaga taattgagtg tcatcagaac tagatnntt                             39

<210> SEQ ID NO 122
<211> LENGTH: 40
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (37)..(38)
<223> OTHER INFORMATION: n = any nucleotide, present or absent

<400> SEQUENCE: 122
atgaggagta attgaaatca ttaatacccca caaacanntt    40

<210> SEQ ID NO 123
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (33)..(34)
<223> OTHER INFORMATION: n = any nucleotide, present or absent

<400> SEQUENCE: 123
aactcagacc aatttggcca tagattatta gcnntt    36

<210> SEQ ID NO 124
<211> LENGTH: 43
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (40)..(41)
<223> OTHER INFORMATION: n = any nucleotide, present or absent

<400> SEQUENCE: 124
acaaaaccct ataaggaaga tgtcattacc catattttan ntt    43

<210> SEQ ID NO 125
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (35)..(36)
<223> OTHER INFORMATION: n = any nucleotide, present or absent

<400> SEQUENCE: 125
acccagcttt atacattcac aaagatatgg tttgnnaa    38

<210> SEQ ID NO 126
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (30)..(31)
<223> OTHER INFORMATION: n = any nucleotide, present or absent

<400> SEQUENCE: 126
acagtggaac agctctctcc ttcttttttn nca    33

<210> SEQ ID NO 127
<211> LENGTH: 47
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (44)..(45)
<223> OTHER INFORMATION: n = any nucleotide, present or absent

<400> SEQUENCE: 127
attagaataa ctactattaa aaaaacccca caaaataact cttnnct         47

<210> SEQ ID NO 128
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (38)..(39)
<223> OTHER INFORMATION: n = any nucleotide, present or absent

<400> SEQUENCE: 128
tttgggaatt aaaagccaat agattagctg aaaattcnna t         41

<210> SEQ ID NO 129
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (33)..(34)
<223> OTHER INFORMATION: n = any nucleotide, present or absent

<400> SEQUENCE: 129
acacctttac atgaaggctt tgaagtactc ttnnat         36

<210> SEQ ID NO 130
<211> LENGTH: 46
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (43)..(44)
<223> OTHER INFORMATION: n = any nucleotide, present or absent

<400> SEQUENCE: 130
gtgcattatg ggtaagaatg ttcatttatt atttcactta tannga         46

<210> SEQ ID NO 131
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (30)..(31)
<223> OTHER INFORMATION: n = any nucleotide, present or absent

<400> SEQUENCE: 131
gaagtcgtag ctattcggca aaggaaatgn ntt         33

<210> SEQ ID NO 132
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(28)
<223> OTHER INFORMATION: n = any nucleotide, present or absent

<400> SEQUENCE: 132
tgccccatag gcagtgtttg gtgaagnngt                                    30

<210> SEQ ID NO 133
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (30)..(31)
<223> OTHER INFORMATION: n = any nucleotide, present or absent

<400> SEQUENCE: 133
taccccatgt gtatcaaatg gtcagcaagn ntt                                33

<210> SEQ ID NO 134
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(26)
<223> OTHER INFORMATION: n = any nucleotide, present or absent

<400> SEQUENCE: 134
ctgtgagttg ggagcaaagg agcannat                                      28

<210> SEQ ID NO 135
<211> LENGTH: 31
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(29)
<223> OTHER INFORMATION: n = any nucleotide, present or absent

<400> SEQUENCE: 135
ctctggagac gggggatgtt aagttganna a                                  31

<210> SEQ ID NO 136
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(28)
<223> OTHER INFORMATION: n = any nucleotide, present or absent

<400> SEQUENCE: 136
tctggtgatt gagaaagcgt tccagannga                                    30

<210> SEQ ID NO 137
<211> LENGTH: 36
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (33)..(34)
<223> OTHER INFORMATION: n = any nucleotide, present or absent

<400> SEQUENCE: 137
attggattaa ctttggtgga acctacttcg atnnat    36

<210> SEQ ID NO 138
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (30)..(31)
<223> OTHER INFORMATION: n = any nucleotide, present or absent

<400> SEQUENCE: 138
ctcccttctt tcatccctac atcatgtccn naa    33

<210> SEQ ID NO 139
<211> LENGTH: 27
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (24)..(25)
<223> OTHER INFORMATION: n = any nucleotide, present or absent

<400> SEQUENCE: 139
cggacttggc tggggtagag cttnnaa    27

<210> SEQ ID NO 140
<211> LENGTH: 31
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (28)..(29)
<223> OTHER INFORMATION: n = any nucleotide, present or absent

<400> SEQUENCE: 140
gagctaagta ccaggtatga tgctcgcnna t    31

<210> SEQ ID NO 141
<211> LENGTH: 33
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (30)..(31)
<223> OTHER INFORMATION: n = any nucleotide, present or absent

<400> SEQUENCE: 141
agggaatgct ctagacaaaa cactgttccn nta    33

<210> SEQ ID NO 142
<211> LENGTH: 32
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (29)..(30)

<223> OTHER INFORMATION: n = any nucleotide, present or absent

<400> SEQUENCE: 142
tgctttgtgc tagctcaaag actcacatnn tt                                  32

<210> SEQ ID NO 143
<211> LENGTH: 38
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (35)..(36)
<223> OTHER INFORMATION: n = any nucleotide, present or absent

<400> SEQUENCE: 143
aattctggat caaattaaat atgtcgcatt ctccnngt                            38

<210> SEQ ID NO 144
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (36)..(37)
<223> OTHER INFORMATION: n = any nucleotide, present or absent

<400> SEQUENCE: 144
tgtactttct ttttagccat aagatgattt cccatnnat                           39

<210> SEQ ID NO 145
<211> LENGTH: 28
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (25)..(26)
<223> OTHER INFORMATION: n = any nucleotide, present or absent

<400> SEQUENCE: 145
gcttgctttc ccacaccact acctnnta                                       28

<210> SEQ ID NO 146
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(28)
<223> OTHER INFORMATION: n = any nucleotide, present or absent

<400> SEQUENCE: 146
ggtcaagtct gaggctgttg agcttannga                                     30

<210> SEQ ID NO 147
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature

```
<222> LOCATION: (26)..(27)
<223> OTHER INFORMATION: n = any nucleotide, present or absent

<400> SEQUENCE: 147
ttcaggacgt gaaagcacga gaacgnnat                                              29

<210> SEQ ID NO 148
<211> LENGTH: 35
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (32)..(33)
<223> OTHER INFORMATION: n = any nucleotide, present or absent

<400> SEQUENCE: 148
atgtacaatt tcaactggag tttccattgc anngt                                       35

<210> SEQ ID NO 149
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(28)
<223> OTHER INFORMATION: n = any nucleotide, present or absent

<400> SEQUENCE: 149
aaatagtgag aacgagcagc tgcaggnnct                                             30

<210> SEQ ID NO 150
<211> LENGTH: 41
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (38)..(39)
<223> OTHER INFORMATION: n = any nucleotide, present or absent

<400> SEQUENCE: 150
aagaatataa aatgttagag aaccacatac aacgagcnnc t                                41

<210> SEQ ID NO 151
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(28)
<223> OTHER INFORMATION: n = any nucleotide, present or absent

<400> SEQUENCE: 151
aaccccagaa cactagcagc taagggnnta                                             30

<210> SEQ ID NO 152
<211> LENGTH: 45
<212> TYPE: DNA
<213> ORGANISM: Artificial Sequence
<220> FEATURE:
<223> OTHER INFORMATION: Synthetic polynucleotide
<220> FEATURE:
```

-continued

<221> NAME/KEY: misc_feature
<222> LOCATION: (42)..(43)
<223> OTHER INFORMATION: n = any nucleotide, present or absent

<400> SEQUENCE: 152 tttattagt tgtgtaatcc agttacttaa ctttaaaagc cnnat          45

<210> SEQ ID NO 153
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(28)
<223> OTHER INFORMATION: n = any nucleotide, present or absent

<400> SEQUENCE: 153
gttctgaaaa gagcctccac tcctgtnntt          30

<210> SEQ ID NO 154
<211> LENGTH: 30
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (27)..(28)
<223> OTHER INFORMATION: n = any nucleotide, present or absent

<400> SEQUENCE: 154
cctccactcc accatggcac ctattannaa          30

<210> SEQ ID NO 155
<211> LENGTH: 45
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (42)..(43)
<223> OTHER INFORMATION: n = any nucleotide, present or absent

<400> SEQUENCE: 155
gtataccact taggctatag ttattctaaa ctttgataaa cnngt          45

<210> SEQ ID NO 156
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (36)..(37)
<223> OTHER INFORMATION: n = any nucleotide, present or absent

<400> SEQUENCE: 156
aggaatcatt acaggaaaac atcgtttaaa ttggannaa          39

<210> SEQ ID NO 157
<211> LENGTH: 37
<212> TYPE: DNA
<213> ORGANISM: Artificial Sequence
<220> FEATURE:
<223> OTHER INFORMATION: Synthetic polynucleotide

```
<220> FEATURE:
<221> NAME/KEY: misc_feature
<222> LOCATION: (34)..(35)
<223> OTHER INFORMATION: n = any nucleotide, present or absent

<400> SEQUENCE: 157
ccatggtata ttgtaagttg taggtacata cccnnaa                               37

<210> SEQ ID NO 158
<211> LENGTH: 37
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (34)..(35)
<223> OTHER INFORMATION: n = any nucleotide, present or absent

<400> SEQUENCE: 158
tttgatttga ataaaccaga gaactcttct gagnntt                               37

<210> SEQ ID NO 159
<211> LENGTH: 34
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (31)..(32)
<223> OTHER INFORMATION: n = any nucleotide, present or absent

<400> SEQUENCE: 159
tgttgctatc ttgcttttag catttagtgc nnaa                                  34

<210> SEQ ID NO 160
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (26)..(27)
<223> OTHER INFORMATION: n = any nucleotide, present or absent

<400> SEQUENCE: 160
tcagcgttga gtaataccgt ctgccnnca                                        29

<210> SEQ ID NO 161
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 161
taagtggaaa gaactggggt gtc                                              23

<210> SEQ ID NO 162
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 162
```
acatggttag atattagcct gacctatg                                    28

<210> SEQ ID NO 163
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 163
gcagccaagt gtgaaagtat tga                                         23

<210> SEQ ID NO 164
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 164
tgatgttgag ttgagacagg ttaca                                       25

<210> SEQ ID NO 165
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 165
aaatgtagtt ctattatggt cagcacac                                    28

<210> SEQ ID NO 166
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 166
agtatcccca aaaggttgca gat                                         23

<210> SEQ ID NO 167
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 167
gtgcaagctg gaggcact                                               18

<210> SEQ ID NO 168
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 168
acaggaaaag aaactaaaat tgtaccctt                                   29

<210> SEQ ID NO 169
<211> LENGTH: 23
<212> TYPE: DNA
<213> ORGANISM: Artificial Sequence

```
<220> FEATURE:
<223> OTHER INFORMATION: Synthetic polynucleotide

<400> SEQUENCE: 169
gaagccagat ctcaaagtgt cct                                            23

<210> SEQ ID NO 170
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 170
gttattggga atgctatgaa agagaca                                        27

<210> SEQ ID NO 171
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 171
agaactcatt tccttatagc tgaagaact                                      29

<210> SEQ ID NO 172
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 172
gcagacactt aggatgtttc cagt                                           24

<210> SEQ ID NO 173
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 173
gagccttagt tcctccatca gtaaa                                          25

<210> SEQ ID NO 174
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 174
aaatttacgt tggtaattgg gtcttgt                                        27

<210> SEQ ID NO 175
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 175
cacagaggtg acagaacaca gt                                             22
```

<210> SEQ ID NO 176
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 176
tagttattca tggtgggaag gcaa                                    24

<210> SEQ ID NO 177
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 177
aaaagataat gttcttgttt atatgcccct g                            31

<210> SEQ ID NO 178
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 178
tacagcaact cacaaactaa tgactct                                 27

<210> SEQ ID NO 179
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 179
ggctgcgatg agacaggaa                                          19

<210> SEQ ID NO 180
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 180
aggcaccaga agtcatcaga atg                                     23

<210> SEQ ID NO 181
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 181
gaccaagctt ttatgcacca ca                                      22

<210> SEQ ID NO 182
<211> LENGTH: 31
<212> TYPE: DNA
<213> ORGANISM: Artificial Sequence
<220> FEATURE:
<223> OTHER INFORMATION: Synthetic polynucleotide

```
<400> SEQUENCE: 182
tgaaagatag caatagatac ataaaacacc a                              31

<210> SEQ ID NO 183
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 183
tgaaaccaca tacacacaaa ttcact                                    26

<210> SEQ ID NO 184
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 184
cttcctgctg tgcatctgta agt                                       23

<210> SEQ ID NO 185
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 185
aaaaagaaga aacggaaggc agag                                      24

<210> SEQ ID NO 186
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 186
tgctgcccca ccctttatta ac                                        22

<210> SEQ ID NO 187
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 187
cctattggaa gaacctgcca gaa                                       23

<210> SEQ ID NO 188
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 188
tgcaaaatga agcacagccc                                           20

<210> SEQ ID NO 189
```

```
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 189
gcagatggaa aatacttggg aaaaaaat                                          28

<210> SEQ ID NO 190
<211> LENGTH: 33
<212> TYPE: DNA
<213> ORGANISM: Artificial Sequence
<220> FEATURE:
<223> OTHER INFORMATION: Synthetic polynucleotide

<400> SEQUENCE: 190
gcaaaaatta ctataccgac tttaataacg aaa                                    33

<210> SEQ ID NO 191
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 191
actcattgta ggctgaacct tgg                                               23

<210> SEQ ID NO 192
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 192
tgtattgagc atttagcaca tgcc                                              24

<210> SEQ ID NO 193
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 193
caatttccaa gacagaagca ctcc                                              24

<210> SEQ ID NO 194
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 194
acttactgag cacatggcct g                                                 21

<210> SEQ ID NO 195
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 195
```

```
ggagagggtg agaagttgca c                                              21

<210> SEQ ID NO 196
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 196
ggcaaagaca ttttttccaag gaagatat                                      28

<210> SEQ ID NO 197
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 197
cactgccagc ttgtgcct                                                  18

<210> SEQ ID NO 198
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 198
gccctaaatc ctaaatgaaa ttggca                                         26

<210> SEQ ID NO 199
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 199
agaggagaaa tagatgtagc tgcc                                           24

<210> SEQ ID NO 200
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 200
aatccagtga cattctttaa actgtctt                                       28

<210> SEQ ID NO 201
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 201
gctgagctgt cacatcactt ca                                             22

<210> SEQ ID NO 202
<211> LENGTH: 25
<212> TYPE: DNA
```

<213> ORGANISM: Artificial Sequence
<220> FEATURE:
<223> OTHER INFORMATION: Synthetic polynucleotide

<400> SEQUENCE: 202
gctgtgtagc ttggcaaatt aacta                                           25

<210> SEQ ID NO 203
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 203
gcactcttgg gtaacaggct tt                                              22

<210> SEQ ID NO 204
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 204
ccatgcccag cctggc                                                     16

<210> SEQ ID NO 205
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 205
tggctcctca taagttatgc agattt                                          26

<210> SEQ ID NO 206
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 206
cagtaggatt ggctttatca aagagatc                                        28

<210> SEQ ID NO 207
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 207
accataatgt tttccataga agatgcac                                        28

<210> SEQ ID NO 208
<211> LENGTH: 32
<212> TYPE: DNA
<213> ORGANISM: Artificial Sequence
<220> FEATURE:
<223> OTHER INFORMATION: Synthetic polynucleotide

<400> SEQUENCE: 208
ggttctgtac tgaagtaaaa atctcatact at                                   32

<210> SEQ ID NO 209
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 209
ggcaaagaaa catggcagaa atatcata                                        28

<210> SEQ ID NO 210
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 210
cctttggcat tttggtcaag attgt                                           25

<210> SEQ ID NO 211
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 211
gggggaaaat ggtttcttag gatga                                           25

<210> SEQ ID NO 212
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 212
ctcccatttt tctaagacat tttttttct c                                     31

<210> SEQ ID NO 213
<211> LENGTH: 16
<212> TYPE: DNA
<213> ORGANISM: Artificial Sequence
<220> FEATURE:
<223> OTHER INFORMATION: Synthetic polynucleotide

<400> SEQUENCE: 213
agcatgccgc ccttgg                                                     16

<210> SEQ ID NO 214
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 214
tcacaggtca aaattatgag ttcttcg                                         27

<210> SEQ ID NO 215
<211> LENGTH: 22
<212> TYPE: DNA
<213> ORGANISM: Artificial Sequence
<220> FEATURE:

<223> OTHER INFORMATION: Synthetic polynucleotide

<400> SEQUENCE: 215
tgagagtgtg caagtcactt gt                                            22

<210> SEQ ID NO 216
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 216
gcaggcagca tgtatcccag                                               20

<210> SEQ ID NO 217
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 217
gtttaatgga cagtagatgc taaattctag a                                  31

<210> SEQ ID NO 218
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 218
cgccatagtt agccgcttcc                                               20

<210> SEQ ID NO 219
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 219
tgagcctcgg tctctacctg                                               20

<210> SEQ ID NO 220
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 220
cctttaaggc ccagcaactg                                               20

<210> SEQ ID NO 221
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 221
gggtgacctt tcccttttga tga                                           23

```
<210> SEQ ID NO 222
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 222
tgtgtgtgaa agcactttat aaacca                                          26

<210> SEQ ID NO 223
<211> LENGTH: 34
<212> TYPE: DNA
<213> ORGANISM: Artificial Sequence
<220> FEATURE:
<223> OTHER INFORMATION: Synthetic polynucleotide

<400> SEQUENCE: 223
ctatcctcag aattttccat tgatactaga aata                                 34

<210> SEQ ID NO 224
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 224
gagtgtctcc caaacaagga tca                                             23

<210> SEQ ID NO 225
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 225
acagccatca gatatccagc ag                                              22

<210> SEQ ID NO 226
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 226
acttcgagaa ttgactctaa gtggt                                           25

<210> SEQ ID NO 227
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 227
aatttagctt ccttgaggat agaagtaac                                       29

<210> SEQ ID NO 228
<211> LENGTH: 17
<212> TYPE: DNA
<213> ORGANISM: Artificial Sequence
<220> FEATURE:
<223> OTHER INFORMATION: Synthetic polynucleotide
```

<400> SEQUENCE: 228
cccggccacc catacag                                                    17

<210> SEQ ID NO 229
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 229
gaaaactacc ttaaactatg tgagaaagaa c                                    31

<210> SEQ ID NO 230
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 230
accctcacta atctttttct gtttgttt                                        28

<210> SEQ ID NO 231
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 231 gttttctctcc cagctgtaaa agca                                           24

<210> SEQ ID NO 232
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 232
gctttagttt ctttgcatat tttctgcaat a                                    31

<210> SEQ ID NO 233
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 233
agctgatctg caaggtctat ttga                                            24

<210> SEQ ID NO 234
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 234
tgggctcaag tgatccacct a                                               21

<210> SEQ ID NO 235
<211> LENGTH: 25

<212> TYPE: DNA
<213> ORGANISM: Artificial Sequence
<220> FEATURE:
<223> OTHER INFORMATION: Synthetic polynucleotide

<400> SEQUENCE: 235
gtaaagagaa gggctaccag gatta                                        25

<210> SEQ ID NO 236
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 236
ccctatgcct gggatacttc ctt                                          23

<210> SEQ ID NO 237
<211> LENGTH: 31
<212> TYPE: DNA
<213> ORGANISM: Artificial Sequence
<220> FEATURE:
<223> OTHER INFORMATION: Synthetic polynucleotide

<400> SEQUENCE: 237
acaaatcttt catttgtcta aggtatcaac t                                 31

<210> SEQ ID NO 238
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 238
agtgtcttgc attttcaagt attcct                                       26

<210> SEQ ID NO 239
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 239
cctaggttat ttgctgttct ctttcatta                                    29

<210> SEQ ID NO 240
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 240
gcttgcatat agacctacaa ataccact                                     28

<210> SEQ ID NO 241
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 241

```
ggcaccatgc atccagcc                                              18
```

<210> SEQ ID NO 242
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 242

```
gtccaagagt ggaggattgg g                                          21
```

<210> SEQ ID NO 243
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 243

```
ggaaatcgta cagttccaaa gtacaa                                     26
```

<210> SEQ ID NO 244
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 244

```
acagcaacag aaactaccca aaag                                       24
```

<210> SEQ ID NO 245
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 245

```
caagcatctt ctccttcctc tct                                        23
```

<210> SEQ ID NO 246
<211> LENGTH: 25
<212> TYPE: DNA
<213> ORGANISM: Artificial Sequence
<220> FEATURE:
<223> OTHER INFORMATION: Synthetic polynucleotide

<400> SEQUENCE: 246

```
cctagtcctt aaccactcct tacag                                      25
```

<210> SEQ ID NO 247
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 247

```
tccaaactgg aaatggctgt atct                                       24
```

<210> SEQ ID NO 248
<211> LENGTH: 33
<212> TYPE: DNA
<213> ORGANISM: Artificial Sequence

```
<220> FEATURE:
<223> OTHER INFORMATION: Synthetic polynucleotide

<400> SEQUENCE: 248
gctttctatt tatttaaaag aaagtgaagt ccc                              33

<210> SEQ ID NO 249
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 249 tttccccct tctctcttct tttt                                         24

<210> SEQ ID NO 250
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 250
cagcagtaca ctgaacagaa tcc                                         23

<210> SEQ ID NO 251
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 251
agggaccagg taaatattta ccacgtcttg gtctttattt taccgtctat atacaag    57

<210> SEQ ID NO 252
<211> LENGTH: 57
<212> TYPE: DNA
<213> ORGANISM: Artificial Sequence
<220> FEATURE:
<223> OTHER INFORMATION: Synthetic polynucleotide

<400> SEQUENCE: 252
agggaccagg taaatattta ccacctcttg gtgtttattt taccgtctat atacaag    57
```

SYSTEMS AND METHODS FOR ALLELE ENRICHMENT USING MULTIPLEXED BLOCKER DISPLACEMENT AMPLIFICATION

REFERENCE TO RELATED APPLICATIONS

The present application is a national phase application under 35 U.S.C. § 371 of International Application No. PCT/US2019/018690, filed Feb. 20, 2019, which claims the priority benefit of U.S. provisional application No. 62/632,712, filed Feb. 20, 2018, and U.S. provisional application No. 62/649,138, filed Mar. 28, 2018, the entire contents of each of which is incorporated herein by reference.

STATEMENT REGARDING FEDERALLY SPONSORED RESEARCH

This invention was made with government support under Grant No. R01 CA203964 awarded by the National Institutes of Health. The government has certain rights in the invention.

REFERENCE TO A SEQUENCE LISTING

The instant application contains a Sequence Listing, which has been submitted in ASCII format via EFS-Web and is hereby incorporated by reference in its entirety. Said ASCII copy, created on Feb. 15, 2019, is named RICEP0042WO_ST25.txt and is 88 kilobytes in size.

BACKGROUND

1. Field

The present invention relates generally to the field of molecular biology. More particularly, it concerns compositions and methods for multiplex enrichment of many different sequence variations having low VAFs.

2. Description of Related Art

Sequence variations in genomic DNA include nonpathogenic single nucleotide polymorphisms (SNPs) that can collectively distinguish individuals from each other, pathogenic germline mutations that can cause or increase the likelihood of genetic diseases, and pathogenic somatic mutations that cause cancer. The technical difficulty distinguishing these sequence variations depends strongly on both the fraction of the DNA that contains the variation (the variant allele fraction; VAF) and the number of variations that need to be simultaneously profiled.

For profiling a few sequence variations (<5) at relatively high VAF (e.g., 5%), quantitative PCR is the standard approach that is used for many FDA-approved or cleared diagnostic tests. For profiling many (1000+) sequence variations at relatively high VAF, microarrays or low-depth next-generation sequencing (NGS) is the commercially preferred method. For profiling a few sequence variations at very low VAF (e.g., <0.1%), digital droplet PCR and ultradeep NGS with unique molecular barcodes are being developed. However, simultaneously profiling many sequence variations each at potentially low VAF remains a significant challenge because microarrays lack the sensitivity for low VAFs, digital PCR cannot be multiplexed past a very small number, and ultradeep NGS is slow and cost prohibitive when applied to many potential mutations.

SUMMARY

Provided herein are reagents and methods to simultaneously enrich, by 100-fold or more, many different sequence variations having low VAFs. For example, sequence variations originally at 0.1% VAF may be enriched to 10% VAF or higher, allowing profiling via low-depth NGS or microarrays in highly multiplexed settings. Applications of these methods include detection of cell line contamination and analysis of rare cancer mutations in liquid biopsy settings.

In one embodiment, provided herein are methods for simultaneously amplifying allelic variants at least ten genetic loci, the method comprising: (a) mixing a sample comprising DNA with a DNA polymerase and a blocker displacement amplification (BDA) oligo set for each genetic locus, each BDA oligo set comprising (i) a BDA forward primer, (ii) a BDA blocker, and (iii) a BDA reverse primer, wherein at least four nucleotides at the 3' end of each BDA forward primer sequence are also present at or near the 5' end of its respective BDA blocker sequence, wherein each BDA blocker contains a 3' sequence or modification that prevents extension by DNA polymerase, and wherein the concentration of each BDA blocker is at least twice that of its respective BDA forward primer; and (b) subjecting the mixture to at least four cycles of amplification, thereby producing amplicons. In some aspects, the methods simultaneously amplify allelic variants at between ten and 1,000,000 genetic loci. In some aspects, the DNA comprises an allelic variant at at least one of the genetic loci.

In some aspects, the final concentrations of all BDA forward primers in the mixture sum to more than 50 nanomolar and less than 50 micromolar. In some aspects, each cycle of amplification in step (b) comprises: (i) a denaturation step at a temperature between 75° C. and 105° C. for between 1 second and 300 seconds; and (ii) an anneal step at a temperature between 45° C. and 75° C. for between 15 seconds and 3 hours. In some aspects, the DNA polymerase is a high-fidelity DNA polymerase, such as, for example, Phusion, NEB Q5, or Kapa HiFi. In certain aspects, the DNA polymerase has 3' to 5' exonuclease activity. In certain aspects, each BDA blocker has a 3' modification that prevents 3' to 5' exonuclease activity. In certain aspects, the 3' modification that prevents 3' to 5' exonuclease activity comprises inverted DNA nucleotides, a phosphorothioate backbone, one or more carbon spacers, or one or more polyethylene glycol (PEG) spacers. In some aspects, step (a) further comprises mixing an intercalating dye that selectively fluoresces when bound to double-stranded DNA, such as, for example, a SybrGreen, EvaGreen, or Syto dye.

In some aspects, the methods further comprise (c) selecting the amplicons produced by step (b) by size. In certain aspects, the selection is performed using affinity beads, affinity columns, gel electrophoresis, or capillary electrophoresis.

In some aspects, the methods further comprise (d1) amplifying the size-selected amplicons by polymerase chain reaction using primers having next-generation sequencing (NGS) adapters and/or sample index sequences, thereby producing adapter and/or sample index modified amplicons. In some aspects, the methods further comprise (d2) ligating onto both ends of the size-selected amplicons oligonucleotides having next-generation sequencing (NGS) adapters and/or sample index sequences, thereby producing adapter and/or sample index modified amplicons.

In some aspects, the methods further comprise (e) performing next-generation sequencing of the adapter and/or sample index modified amplicons.

In some aspects, the concentration of each BDA reverse primer is determined based on a reads analysis of a previous calibration NGS experiment, wherein the concentration of each BDA reverse primer is increased relative to the concentration used for the previous calibration NGS experiment. In certain aspects, the concentration of each BDA reverse primer follows a formula: [rP]new=[rP]old*(Reads_median/Reads_amplicon)^X, where [rP]old is the previous concentration of the reverse primer, Reads_median is the median reads mapped to each amplicon, Reads_amplicon is the reads mapped to the amplicon corresponding to said reverse primer, and X is an adjustment factor between 0.25 and 1.

In some aspects, the concentration of each BDA forward primer is determined based on a reads analysis of a previous calibration NGS experiment, wherein the concentration of each BDA forward primer is increased relative to the concentration used for the previous calibration NGS experiment. In certain aspects, the concentration of each BDA forward primer follows a formula: [fP]new=[fP]old*(Reads_ median/Reads_amplicon)^X, where [fP]old is the previous concentration of the forward primer, Reads_median is the median reads mapped to each amplicon, Reads_amplicon is the reads mapped to the amplicon corresponding to said forward primer, and X is an adjustment factor between 0.25 and 1.

In one embodiment, provided herein are methods for designing the sequences of BDA oligo sets, each comprising a BDA forward primer, a BDA blocker, and a BDA reverse primer, for a locus group of interest, the method comprising: (1) selecting either the (+) or (−) DNA strand to be used as a BDA template for the locus group of interest; (2) removing loci that require incompatible enrichment regions; (3) creating a list of candidate BDA forward primers, BDA blockers, and BDA reverse primers for each remaining locus; (4) selecting a random BDA forward primer, BDA blocker, and BDA reverse primer from the candidate list for each locus; (5) evaluating the likelihood of primer dimer formation for the set of all selected BDA forward primers, BDA blockers, and BDA reverse primers; (6) replacing with other candidate sequences from (3) some BDA forward primers, BDA blockers, or BDA reverse primers identified in step (5) as forming primer dimers; and (7) repeating steps (5) and (6) for a fixed number of cycles, or until the evaluation in step (6) returns an acceptable result.

In some aspects, the BDA oligonucleotide sets are for use in simultaneously amplifying allelic variants at multiple genomic loci. In some aspects, evaluating in step (5) comprises evaluating the potential reverse complementarity between the 3'-most 4-8 nucleotides of all possible pairs of BDA forward primers, BDA blockers, and BDA reverse primers. In some aspects, evaluating in step (5) comprises evaluating the potential reverse complementarity between any continuous subsequences 6-10 nucleotides in length of all possible pairs of BDA forward primers, BDA blockers, and BDA reverse primers.

In one embodiment, provided herein are methods for analyzing NGS reads generated by a method of the present embodiments, the method comprising: (a) removing read sequences having a quality below a set quality threshold; (b) aligning the remaining read sequences to the expected wildtype amplicon sequences; (c) identifying each variation in read sequences that differ from the corresponding wildtype amplicon sequence in an enrichment region; (d) calculating the fraction of read sequences aligned to each amplicon that correspond to each variation; and (e) discarding reads corresponding to variations in which the calculated fraction is below a set threshold value.

In some aspects, the threshold value in step (e) is between 0.1% and 10%. In some aspects, the methods further comprise calculating a variant allele fraction (VAF) for each variation not discarded in step (e) by using the formula of VAF=RF/(E*(1−RF)+RF), where E is the expected fold-enrichment of the variation and RF is the observed reads fraction of the variation. In certain aspects, the value of E for some variants is determined based on calibration experiments using reference samples bearing said variants at known VAFs. In certain aspects, the value of E for some variants is determined based on the nucleotide identities of the wildtype sequence, the variant sequence, and the sequence located 50 nt upstream and 50 nt downstream of the variant sequence (e.g., based on statistical or machine learning of E values for similar sequences). In certain aspects, the methods further comprise calculating a quantitative estimate of the fraction of the minority cell type from a heterogeneous cell sample by taking a median of the inferred VAF values for 3 or more different variants. In some aspects, the methods further comprise calculating a quantitative estimate of the fraction of the minority cell type from a heterogeneous cell sample by taking a mean of the inferred VAF values for 3 or more different variants In one embodiment, provided herein are aqueous solutions of oligonucleotides molecules, the solution comprising at least 10 BDA oligo sets, each BDA oligo set comprising (i) a BDA forward primer, (ii) a BDA blocker, and (iii) a BDA reverse primer, wherein at least four nucleotides at the 3' end of each BDA forward primer sequence are also present at or near the 5' end of its corresponding BDA blocker sequence, wherein each BDA blocker contains a 3' sequence or modification that prevents extension by DNA polymerase, and wherein the concentration of each BDA blocker is at least twice that of its corresponding BDA forward primer, wherein each BDA blocker is complementary to a genomic region bearing a single nucleotide polymorphism (SNP) in which the alternative allele has a population frequency of between 10% and 90%, and wherein each corresponding BDA forward primer is not complementary to the SNP locus. In some aspects, the solution comprises between ten and 1,000,000 BDA oligo sets. In some aspects, none of the BDA forward primers and none of the BDA reverse primers are complementary to any SNP in which the alternative allele has a population frequency of over 1%. In some aspects, the genomic position that each BDA reverse primer binds is located between 100 nt and 500 nt away from the genomic position that its corresponding BDA forward primer binds. In some aspects, the calculated $\Delta G°$'s for each BDA forward primer binding to its corresponding complement are all within 2 kcal/mol of each other at 60° C. in 0.18 M Na+. In some aspects, the calculated $\Delta G°$ for each BDA blocker binding to its corresponding complement is between 0.5 kcal/mol and 3.5 kcal/mol more favorable than the $\Delta G°$ of binding between the corresponding BDA forward primer and its complement at 60° C. in 0.18 M Na+.

In one embodiment, provided herein are methods for detecting contamination of a base cell line, the method comprising: (a) extracting genomic DNA from a cell sample; (b) mixing the genomic DNA with a DNA polymerase, dNTPs, and the aqueous solution of any one of the present embodiments; (c) subjecting the mixture to at least four cycles of amplification, thereby producing amplicons; and (d) analyzing the amplification reaction or the amplicon mixture. In some aspects, the SNPs are nonpathogenic. In some aspects, the BDA blockers selectively hybridize to the SNP alleles of the base cell line. In some aspects, the BDA blockers do not selectively hybridize to the SNP alleles of the base cell line.

In some aspects, each cycle of amplification in step (c) comprises: (i) a denaturation step at a temperature between 75° C. and 105° C. for between 1 second and 300 seconds; and (ii) an anneal step at a temperature between 45° C. and 75° C. for between 15 seconds and 3 hours. In some aspects, step (b) further comprises mixing the genomic DNA with an intercalating dye that selectively fluoresces when bound to double-stranded DNA. In some aspects, between 10 and 80 cycles of amplification are performed in step (c). In some aspects, step (d) comprising comparing the amplification Cycle Threshold (Ct) value to a reference value.

In some aspects, step (b) further comprises mixing the genomic DNA with an internal control set of primers and a Taqman probe to the internal control, and wherein the reference value is the Taqman probe-derived Ct value of the internal control. In certain aspects, the at least 3 aliquots of the genomic DNA sample are run, and wherein the analysis in step (d) is performed based on the difference between the median intercalating dye Ct value and the median Taqman probe Ct value. In certain aspects, at least 3 aliquots of the genomic DNA sample are run, and wherein the analysis is performed based on the difference between the mean intercalating dye Ct value and the mean Taqman probe Ct value.

In some aspects, step (d) comprises: (i) preparing an NGS library based using the amplicons produced in step (c); (ii) performing high-throughput sequencing of the NGS library to obtain NGS reads; and (iii) interpreting the NGS reads. In certain aspects, the BDA blockers selectively hybridize to the SNP alleles of the base cell line, and wherein a positive result for contamination is obtained if the analysis of the NGS reads indicates the presence of any SNP alleles differing from the base cell sample SNP alleles above a threshold reads fraction. In certain aspects, the threshold reads fraction is between 0.1% and 10%. In certain aspects, the methods further comprise identifying the contaminant based on the pattern of detected SNP alleles that differ from the SNP alleles of the base cell lines. In certain aspects, the BDA blockers do not selectively hybridize to the SNP alleles of the base cell line, and wherein a positive result for contamination is obtained if the analysis of the NGS reads indicates the presence of contaminant SNP alleles above a threshold reads fraction. In certain aspects, the threshold reads fraction is between 0.1% and 10%.

In one embodiment, provided herein are panels of non-pathogenic SNPs comprising at least 30 nonpathogenic SNPs, wherein each SNP has an alternative allele with a population frequency of between 10% and 90%, wherein each pair of SNPs is either on different chromosomes or has a genomic distance of at least 2,000 nucleotides, wherein the sequence 50 nucleotides upstream and 50 nucleotides downstream of the SNP is unique within the organism's genome. In some aspects, the panel is for use in verifying the genomic identity of an individual or an organism. In some aspects, the sequence 50 nucleotides upstream and 50 nucleotides downstream of the SNP are unique within the organism's genome if no other region of the organism's genome has a greater than 90% homology to the sequence. In some aspects, each SNP has an alternative allele with a population frequency of between 20% and 80%. In some aspects, the organism is *Homo sapiens*. In some aspects, the panels comprise SNPs from each of the 22 pairs of autosomes in the human genome.

In one embodiment, provided herein are methods of preparing the panel of any one of the present embodiments, the method comprising: (a) obtaining a list of candidate SNPs with exact genomic positions and estimates of population frequencies; (b) removing candidate SNPs with alternative alleles having population frequency of below 10% or above 90%; (c) randomly selecting roughly double the number of desired SNPs from the remaining list, wherein the randomly selected SNPs are spaced by at least 2,000 nucleotides from any other randomly selected SNPs located on the same chromosome; (d) removing SNPs where the sequence 50 nucleotides upstream and 50 nucleotides downstream of the SNP exists in duplicate or with high homology to other regions of the genome; and (e) selecting a final list of SNPs for the panel from the remaining candidate SNPs. In some aspects, the methods further comprise preparing a BDA oligonucleotide set for each of the remaining candidate SNPs.

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.05%, preferably below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 5A-B: Considerations for fP, B, and rP sequence design for mBDA. (FIG. 5A) Examples of potential nonselective binding interactions between fP, B, and/or rP that can lead to primer dimer formation. (FIG. 5B) Subgrouping variants/loci for mBDA.

(FIG. 6A) Inference of VAF from unenriched multiplex PCR library, based on fraction of reads mapped to variant allele at each locus. (FIG. 6B) Relationship between initial VAF and post-mBDA NGS reads fraction mapped to variant allele. (FIG. 6C) Summary of fold enrichment E for different SNP types. (FIG. 6D) Inferred VAF from reads fraction (from post-mBDA NGS) and fitted E values.

FIG. 8: Detection of cell line contamination using SNP patterns.

FIGS. 11A-E: Detection of minute cell line contamination using multiplex blocker displacement amplification (mBDA). (FIG. 11A) A list of SNPs in which the primary cell line is homozygous (either for the human reference allele, or the minor allele). (FIG. 11B) The Blocker is designed to be perfectly complementary to the DNA template bearing primary SNP allele, and mismatched to the variant SNP allele. (FIG. 11C) A 21-plex mBDA set designed against the primary alleles for all 21 SNP positions selected. (FIG. 11D) mBDA maintains a large Ct difference between the primary and variant alleles in highly multiplexed reactions. (FIG. 11E) Detection of different frequencies of HeLa contamination in NA18537 via mBDA using qPCR.

(FIG. 12A) SNP genotypes for 21 different contaminant samples. (FIG. 12B) Simulated distribution of the number of unique contaminant alleles out of the 21 SNPs observed, against NA18537, based on reported SNP population allele frequencies and assuming independence between SNPs. (FIG. 12C) Simulated distribution of the number of homozygous SNPs out of 80 for an arbitrary cell line, based on reported SNP population allele frequencies and assuming independence between SNPs. (FIG. 12D) Summary of qPCR results for detection of 5% contaminant in NA18537 with 37 different human DNA contaminants.

(FIG. 13A) Summary of the mBDA NGS library preparation workflow. (FIG. 13B) Summary of NGS results on an amplicon library without using mBDA. (FIG. 13C) Summary of NGS results for the mBDA NGS library on the sample 0.1% VAF sample. (FIG. 13D) Summary of the variant read fraction (VRF) for each SNP locus in the libraries described in panels (FIG. 13B) and (FIG. 13C). (FIG. 13E) Reproducibility of the VRFs in two replicate mBDA NGS libraries using the 0.1% VAF sample.

(FIG. 14A) Theoretical relationship between VRF and VAF for different allele enrichment-fold (EF). (FIG. 14B) The relationship between (1-VRF)/VRF and (1-VAF)/VAF. (FIG. 14C) Summary of inferred EF for each of the 80 variant SNP alleles using NA18537 as the primary alleles. (FIG. 14D) Relative EF values for different VAF inputs. (FIG. 14E) VAF limit of detection (LoD) for standard amplicon NGS vs. mBDA NGS.

(FIG. 15A) Results for 22 mBDA libraries on a single MiSeq chip. (FIG. 15B) Comparison libraries using standard amplicon NGS on the samples contaminated with S9 (HeLa). (FIG. 15C) Summary of variant call accuracy using the 0.019% VAF LoD threshold described in FIG. 14E. (FIG. 15D) Receiver operator characteristic (ROC) plot for variant calls using the data in panel (FIG. 15C).

(FIG. 16A) Calculation of contaminant likelihood based on mBDA variant calls. (FIG. 16B) Heatmap plot of log 10(L) values for all pairwise combinations of all 22 tested samples (with contamination fraction between 0.07% and 0.22%) vs. 35 database genotypes, based on data from FIG. 15A. (FIG. 16C) Representative distributions of log 10(L) for 4 different samples. (FIG. 16D) Plot of highest and second-highest log 10(L) values against the contamination fraction.

DETAILED DESCRIPTION

A typical blocker displacement amplification (BDA) system uses three different oligonucleotides: the forward primer (fP), the blocker (B), and the reverse primer (rP). The forward primer and the reverse primer are designed to function as standard PCR primers. In some embodiments, the binding of the forward and reverse primers to their respective reverse complement sequences have a computed melting temperature of approximately 50° C., approximately 55° C., approximately 60° C., approximately 65° C., or approximately 70° C. in a buffer suitable for PCR, at primer concentrations of between 100 nM and 5 μM. In some embodiments, the binding of the forward and reverse primers to their reverse complement sequences have a computed standard free energy of binding (4WD and ΔG° rP, respectively) of approximately −11 kcal/mol at approximately 50° C., approximately 55° C., approximately 60° C., approximately 65° C., or approximately 70° C. in a buffer suitable for PCR.

Figure 1:
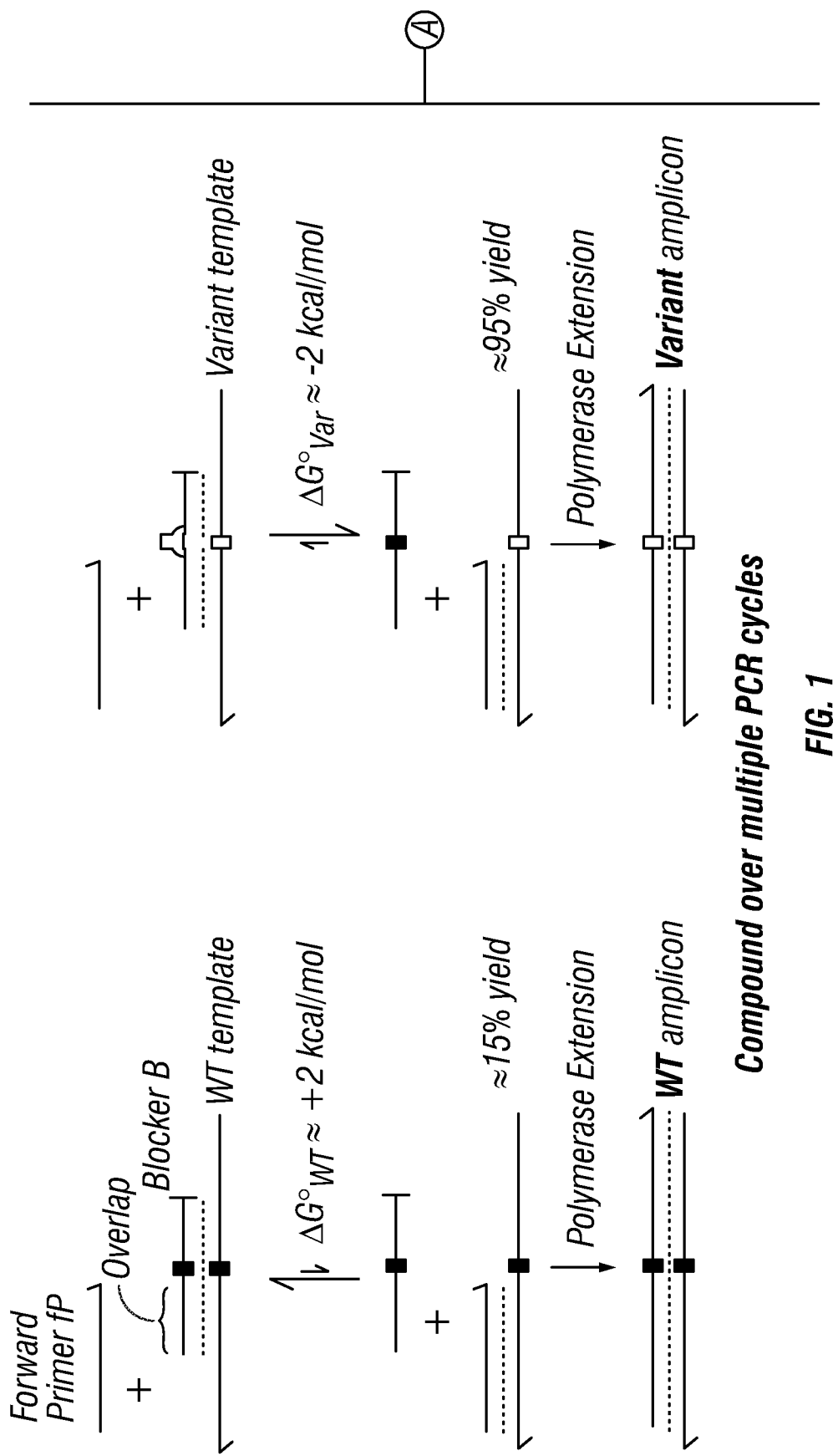
FIG. 1: Schematic and mechanism of single-plex blocker displacement amplification (BDA). The sequence of fP is provided in SEQ ID NO: 20. The sequence of B is provided in SEQ ID NO: 100. The sequence of WT (NA18537) is provided in SEQ ID NO: 251. The sequence of Variant (NA18562) is provided in SEQ ID NO: 252.
Figure 1:
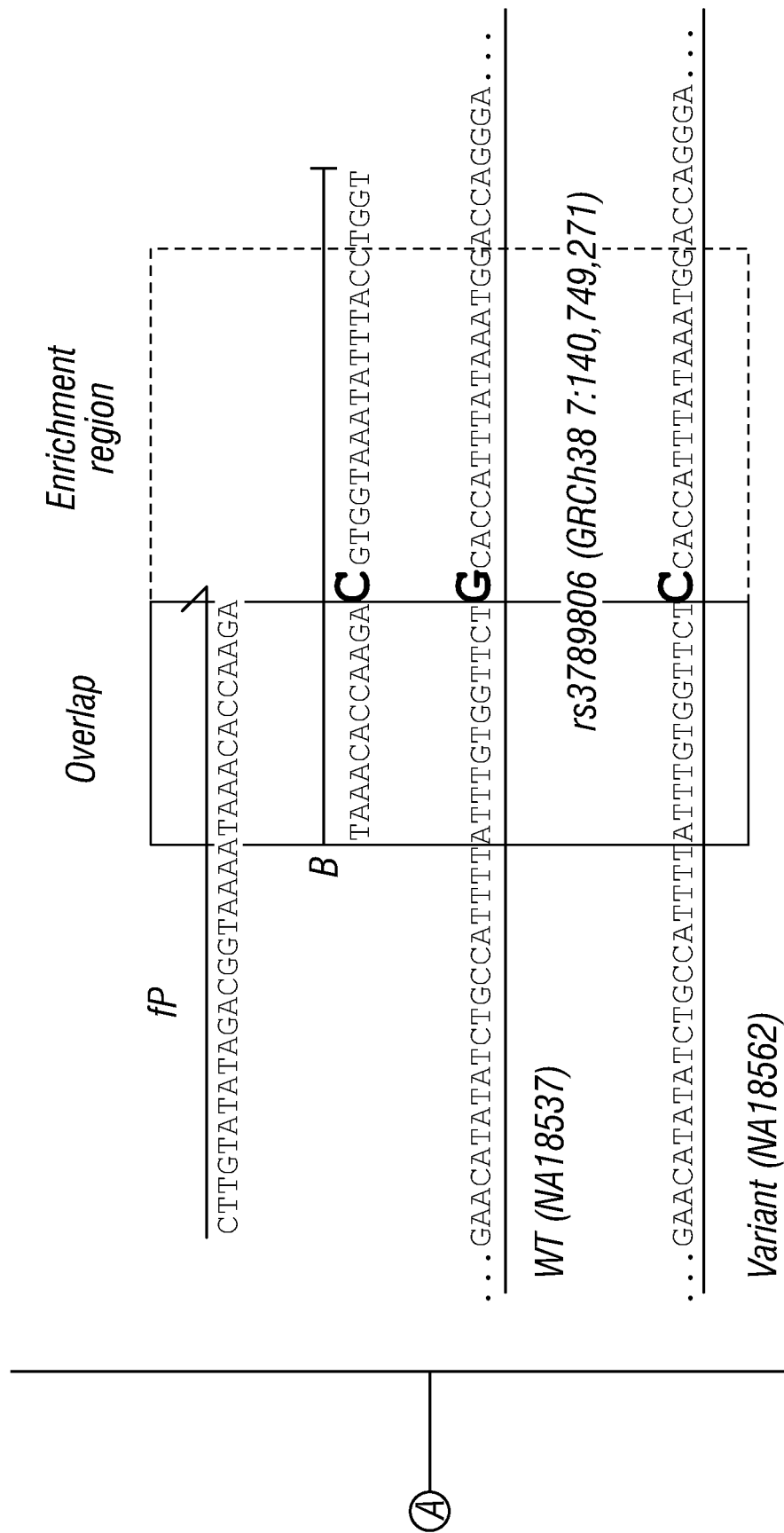

The forward primer (fP) and the blocker (B) are designed to have a certain degree of sequence overlap, with several 3' most nucleotides of fP being identical to several nucleotides on B near the 5' end. This forces the binding of fP and the binding of B, to overlapping regions on a template DNA molecule, to be mutually exclusive (FIG. 1). With high probability, a three-stranded molecule comprising the template, fP, and B colocalized via DNA hybridization interactions will rapidly dissociate, releasing either a single-stranded fP or single-stranded B into solution. In some embodiments, the number of nucleotides of overlap between the forward primer and the blocker is 4, 5, 6, 7, 8, 9, 10, 11, 12, 13, 14, 15, 16, 17, 18, 19, or 20. In some embodiments, the standard free energy of binding (ΔG°) of the overlapping nucleotides to their reverse complement sequences is −4 kcal/mol at approximately 50° C., approximately 55° C., approximately 60° C., approximately 65° C., or approximately 70° C. in a buffer suitable for PCR.

In some embodiments, the binding of the blocker to its reverse complement sequence has a computed melting temperature of approximately 55° C., approximately 60° C., approximately 65° C., approximately 70° C., approximately 75° C., or approximately 80° C. in a buffer suitable for PCR, at blocker concentrations of between 100 nM and 5 µM. In some embodiments, the binding of the blocker to its reverse complement sequence has a computed standard free energy of binding ($\Delta G°$ B) of approximately −14 kcal/mol at approximately 50° C., approximately 55° C., approximately 60° C., approximately 65° C., or approximately 70° C. in a buffer suitable for PCR.

The blocker (B) is designed to be perfectly complementary to a wildtype sequence, so any template with a variant allele in the enrichment region produces a destabilizing mismatch bubble when B is bound to the template. Consequently, fP will more favorably displace B on variant templates than on wildtype templates, and this results in a difference in the per-cycle amplification yield. The yield difference is compounded across multiple cycles of PCR. The enrichment region typically includes all bases to the 3' of the overlap region, except for the four 3'-most nucleotides on B. All variants at any position in the enrichment region will be enriched.

In some embodiments, the standard free energy of the blocker binding to its reverse complement ($\Delta G°_B$) is stronger than the standard free energy of the forward primer binding to its reverse complement ($\Delta G°_{fP}$) by between −1 kcal/mol and −4 kcal/mol at approximately 50° C., approximately 55° C., approximately 60° C., approximately 65° C., or approximately 70° C. in a buffer suitable for PCR. In some embodiments, the blocker comprises a sequence at or near the 3' end that does not hybridize to the template and prevents DNA polymerase extension. In some embodiments, the blocker comprises a chemical modification at or near the 3' end that prevents DNA polymerase extension. In some embodiments, the blocker comprises a chemical modification at or near the 3' end that prevents 3'->5' exonuclease activity by error-correct DNA polymerases. In some embodiments, the said chemical modification comprises inverted DNA nucleotides. In some embodiments, the said chemical modification comprises 3-carbon spacers (C3 spacers).

In the design of the present probe system, the $\Delta G°$ term denotes the standard free energy of hybridization between two complementary strands. In one instance, the standard free energies of hybridization between regions of the present probe system can be approximately calculated based on a base pair stacking approach. In this method, two adjacent base pairs comprise one stack, which has a defined enthalpy ($\Delta H°$) and entropy ($\Delta S°$) value.

The standard free energy of each stack ($\Delta G°$) at a particular temperature $\tau$ (in Kelvin) can be calculated from the equation $\Delta G° = \Delta H° - \tau \Delta S°$. The standard free energies of several stacks can be summed to evaluate the standard free energy of a binding region. The $\Delta H°$ and $\Delta S°$ values of DNA-DNA stacks can be found in SantaLucia and Hicks (2004). Because current literature-provided standard free energy values are incomplete and of limited accuracy, experimental testing is needed to determine a true value of $\Delta G°$ for any two complementary strands, but the literature-guided values provide a rough (typically within 3 kcal/mol or 15%) estimate of the $\Delta G°$.

Figure 2:
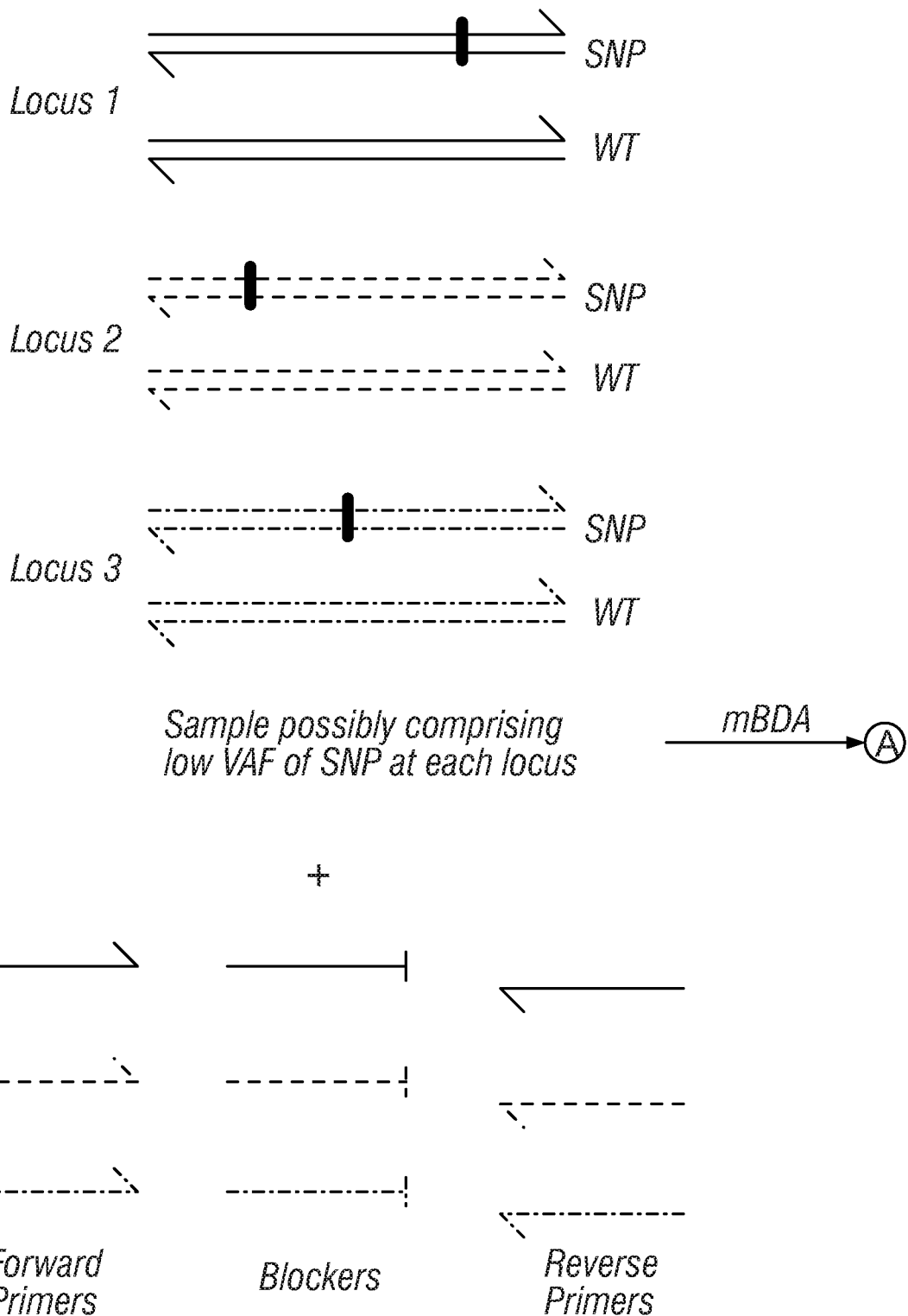
FIG. 2: Multiplex BDA (mBDA) to simultaneously enrich potential sequence variants at many groups of genetic loci.
Figure 2:
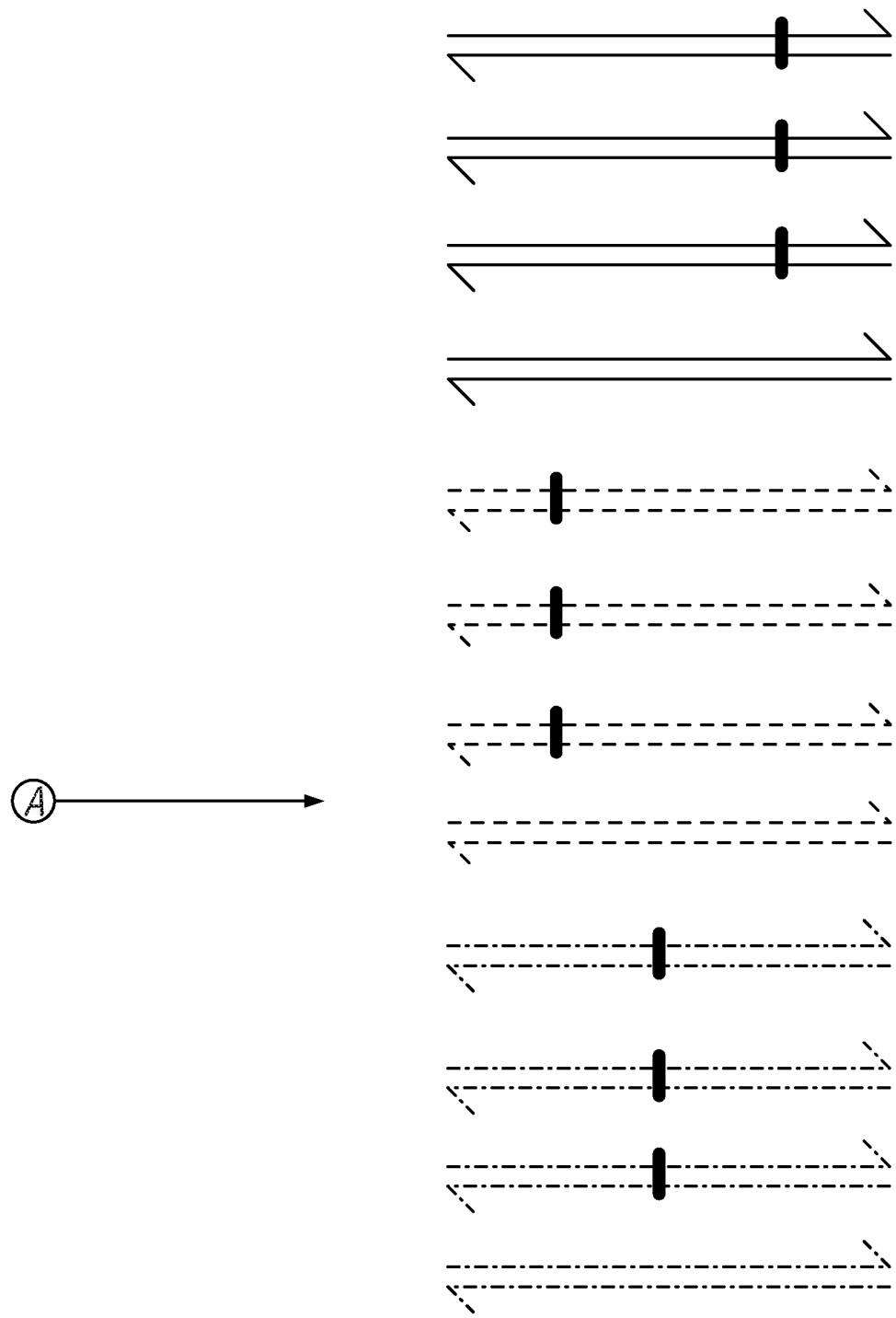

For multiplex BDA (mBDA) to simultaneously enrich potential sequence variants at many groups of genetic loci, different fP, B, and rP species are employed for each BDA system. These are all combined in solution simultaneously with the sample, a DNA polymerase, dNTPs, and buffers amenable for PCR (FIG. 2). To prevent DNA-based inhibition of PCR, the total concentration of all oligo species should be kept under 50 micromolar. The length of the anneal/extend step of the PCR reaction is inversely proportional to the concentration of the lowest of the forward primer species. To prevent excessively long protocols, it is recommended that all fP and rP concentrations be at least 100 picomolar. The concentration of each B species should be at least 2× that of its corresponding fP species. The concentration of each rP species can be adjusted to allow relatively uniform amplification of all BDA amplicons. In some embodiments, the concentration of each rP species is determined based on the observed reads for each BDA amplicon from a prior NGS experiment with known rP concentrations.

I. DESIGN OF OLIGOS FOR MULTIPLEX BDA

In addition to the standard design principles of single-plex BDA described above, oligo design for multiplex BDA (mBDA) requires further consideration to prevent formation of unintended amplicons from two reverse primers in opposite directions and undesired "primer dimer" species. The first issue can largely be avoided if all BDA systems target the same (+) or (−) strand of template DNA, or alternatively if the template is short (e.g., cell-free DNA from blood plasma, or genomic DNA sheared by ultrasonication or fragmentase).

The primer dimer issue is more complex, because the possibility of primer dimer formation increases nonlinearly with the number of different primer and blocker species in solution. For example, in a 10-plex mBDA system, there are 20 primers and 10 blockers, for a total of Combination(30, 2)=435 pairwise interactions; for a 20-plex mBDA system, there are 40 primers and 20 blockers, for a total of Combination(60,2)=1,770 pairwise interactions. The complexity of the problem becomes worse because some primer "dimer" species arise from more complex mechanisms involving three different oligo species or more (FIG. 5A). Shown are examples of potential nonselective binding interactions between fP, B, and/or rP that can lead to primer dimer formation. Algorithms for mBDA sequence design should penalize candidate sequence sets when they are predicted to exhibit any of the listed interactions.

One embodiment of an algorithm that designs mBDA primers and blockers to largely avoid primer dimers is described below. Many potential variations of this algorithm should be obvious to those of ordinary skill in the art of nonconvex optimization software.

1. Determine the preferred direction of each mBDA system, in terms of the blocker binding to either the (+) or the (−) strand of biological DNA. The direction preference may be informed (1) by predicted $\Delta\Delta G°$ of the blocker binding to a specific variant vs. the wildtype, (2) by consideration of other compatibility with other loci of interest as briefly described in FIG. 5B, and (3) by the average expected length of the DNA to be analyzed.

Figure 5B:
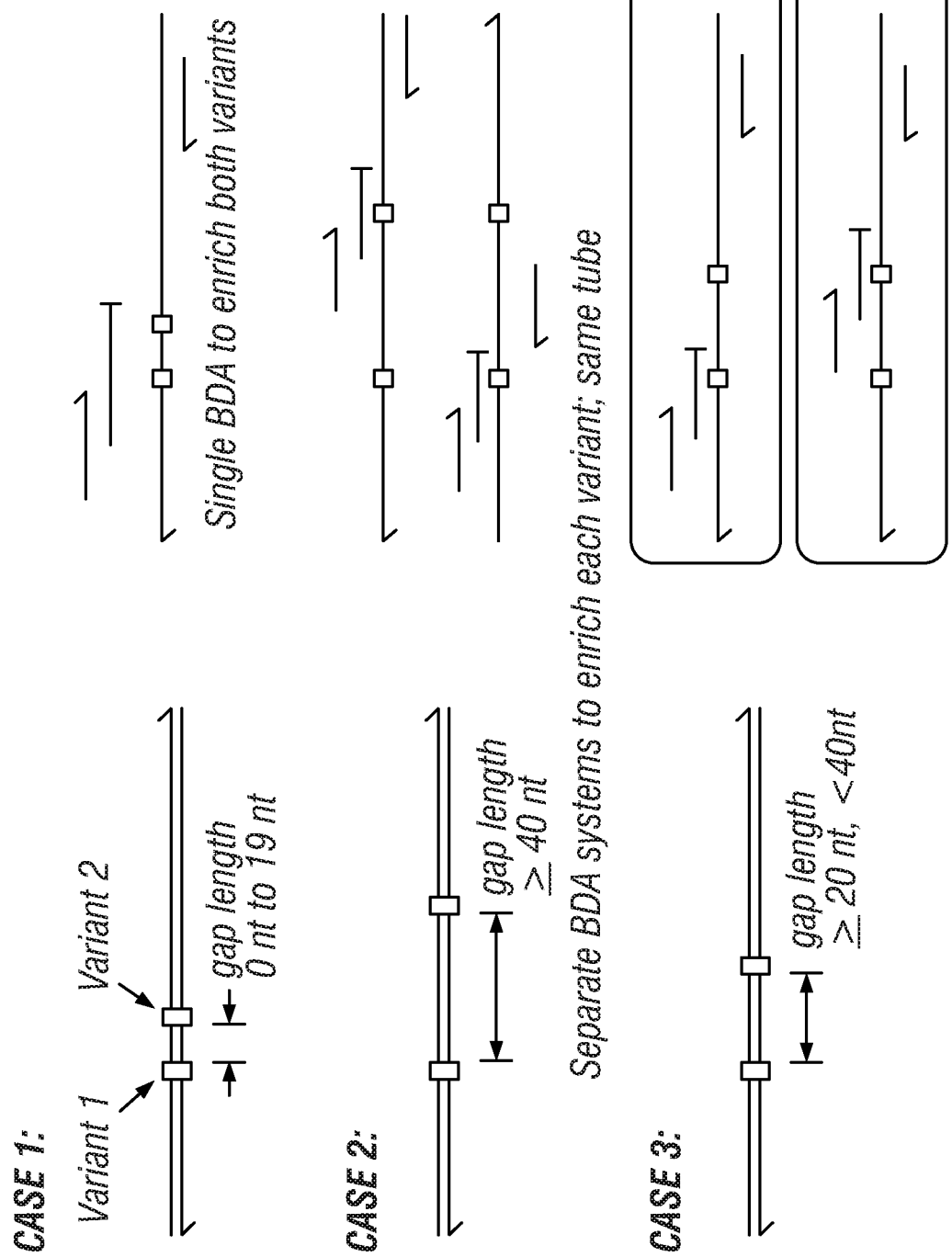

2. Partitioning the loci of potential variants into one or more groups, based on the distance between loci of variants as illustrated in FIG. 5B. When the distance is fewer than about 20 nucleotides, a single blocker B can cover both variant loci within its enrichment region (Case 1). When the distance is farther than about 40 nucleotides, two separate BDA systems can be designed to function within the same reaction without expected adverse effects (Case 3). However, when the distance is between about 20 and about 40 nucleotides, there is insufficient room to place a second BDA system, so two separate BDA systems in two separate reactions are needed (Case 2). BDA oligos for enriching different loci within the same group are meant to be used in the same solution. Disjoint potential variations in which each group of <20 nt loci are spaced from all other loci by over 100 nt are all compatible with each other and can be placed in the same group. At the other extreme, when potential variations can exist at any position in a very long stretch of DNA, such as in a tumor suppressor gene like TP53, the loci may need to be partitioned into 3 to 5 different groups. The remainder of the mBDA sequence design protocol is performed on fP, B, and rP species within a single group.

3. Creating a list of candidate fP, B, and rP sequences for each BDA system within the group. In some embodiments, fP and B candidate sequences satisfy the following constraints: (1) the fP and rP each binds to the template with a calculated $\Delta G°$ between −10 kcal/mol and −15 kcal/mol at the temperature and salinity condition of the anneal cycle of PCR; (2) B binds to the template with a calculated $\Delta G°$ between −12 kcal/mol and −18 kcal/mol at the temperature and salinity condition of the anneal cycle of PCR; (3) the portion of fP that does not overlap with B binds to the templates with a calculated $\Delta G°$ of between −5.5 kcal/mol and −8.5 kcal/mol at the temperature and salinity condition of the anneal cycle of PCR; (4) the amplicon length is between 60 nt and 300 nt long; and (5) B's enrichment region should cover the loci bearing potential sequence variations. Depending on the number of continuous loci to be enriched, there may be between 1 and 25 different candidate sequences for each of fP and B in each BDA system. Depending on the stringency of the amplicon length, there may be between 10 and 200 candidate sequences for each rP. For example, for a 20-plex BDA, there will be 20 different sets of fP candidates, 20 different sets of B candidates, and 20 different sets of rP candidates.

4. Selecting a random initial set of sequences, the set comprising one randomly selected fP sequence for each BDA system, one randomly selected B sequence for each BDA system, and one randomly selected rP sequence for each BDA system. For example, for a 20-plex BDA with 15 candidates for each fP, B, and rP species, there will be $15^{60} \approx 3.7 * 10^{70}$ possible sets of initial random sequences.

5. Performing a heuristic evaluation of the primer dimer likelihood of the randomly selected set of sequences through the calculation of a quantitative "Badness" or "Loss" score that is initialized to 0, and then is incremented based on evaluation of individual oligo properties and/or pairwise oligo interactions. In some embodiments, a pair of oligos in the set contributes to Badness/Loss if the five 3'-most nucleotides of the first oligo are the reverse complement of the five 3'-most nucleotides of the second oligo. In some embodiments, the number of nucleotides at the 3'-most end evaluated for potential reverse complementary with other 3'-most nucleotides is 4, 5, 6, 7, 8, 9, 10, 11, 12, 13, 14, 15, 16, 17, 18, 19, or 20. In some embodiments, a pair of oligos contribute to Badness/Loss based on the calculated standard free energy of interaction $\Delta G°_i$; in some embodiments, the Badness/Loss contribution may be linear, quadratic, or exponential in $\Delta G°_i$. In some embodiments, a pair of oligos contribute to Badness/Loss based on the number of continuous nucleotides of the first strand that are reverse complementary to a number of continuous nucleotides on the second strand. In some embodiments, a single oligo contributes to Badness/Loss based on the calculated free energy of its predicted secondary structure.

6. Creating a new mBDA oligo set based on the existing BDA oligo set, except with one randomly selected fP, B, or rP species replaced by another candidate of the same type. The Badness/Loss of the new mBDA oligo set is evaluated.

7. Deciding whether to accept the potential sequence change based on the Badness/Loss of the new set, compared to the Badness/Loss of the old sequence set. In some embodiments, the new mBDA oligo set is accepted only if the Badness/Loss is improved over the old set. In the field of computer optimization, this strategy is known as gradient descent or stochastic gradient descent. Alternatively, mBDA oligo sets with slightly worse Badness/Loss are also accepted with some probability inversely proportional to the amount of Badness/Loss change. In some embodiments, this probability diminishes over time. In the field of computer optimization, this strategy is known as simulated annealing. Other methods for nonconvex optimization, such as genetic algorithms, may also be applied.

8. Repeating steps (6) and (7) for a fixed number of cycles, or until the Badness/Loss of the BDA oligo set is below an acceptable threshold.

In some embodiments, the above algorithm is applied with the variation that the fP and B candidate sequences are evaluated as a pair rather than as individual oligos. In Step 6, the attempted replacement will be either for a pair of fP/B or for an individual rP oligo. For example, for a 20-plex BDA with 15 candidates for each fP/B pair and 30 candidates for each rP, there will be $15^{20} * 30^{20} = 1.2 * 10^{53}$ possible sets of oligos.

II. OPERATION OF mBDA IN QUANTITATIVE PCR (QPCR) ASSAYS mBDA amplicons can be read out by qPCR using either an intercalating dye (e.g., SybrGreen, EvaGreen, Syto) or with amplicon-specific Taqman probes. The design of Taqman probes for qPCR is known to one of ordinary skill in the art of molecular probe design. The observed solution fluorescence thus can correspond to either the total quantity of amplified DNA, or the quantity of the specific amplicon that the Taqman probe targets.

To accommodate the increased number of oligonucleotide species (fP, B, and rP) in mBDA systems, primer and blocker concentrations are reduced from standard single-plex PCR and BDA reactions. There are two reasons for using lower oligo concentrations: (1) reduced oligo concentrations quadratically reduce the likelihood of primer dimer formation, and (2) high concentrations of ssDNA and dsDNA are known to inhibit PCR. In some embodiments, the total concentrations of all fP, B, and rP species in the final PCR solution are kept between 50 nM and 50 μM.

The most straightforward division of the total concentration among the different mBDA oligos is to have identical fP and rP concentrations, and B concentrations a fixed multiple of the fP concentration. For example, a 20-plex mBDA system targeting 2 μM total oligo concentration could have all fP and rP species each at 20 nM, and all B species each at 60 nM. The cycle threshold (Ct) value of the qPCR amplification can be used to detect or quantitate sequence variations in the enrichment loci of the mBDA. Depending on the exact nature of the readout (intercalating dye vs. Taqman probe), the Ct value reflects either a specific sequence variation, any variation at a locus or a group of adjacent loci, or any variation across all loci enriched by mBDA.

Figure 3:
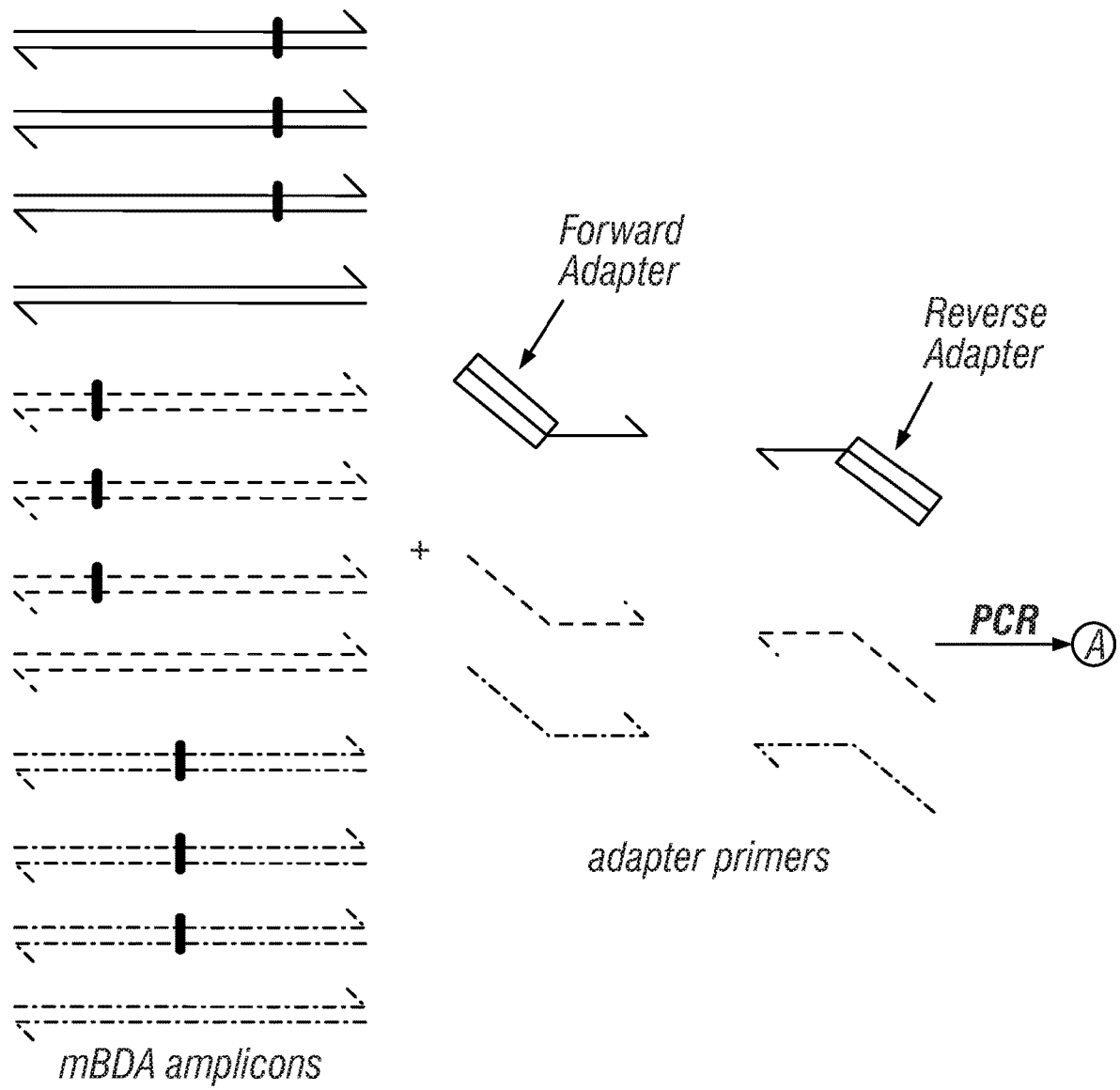
FIG. 3: Appending NGS sequencing adapters to mBDA amplicons via PCR.
Figure 3:
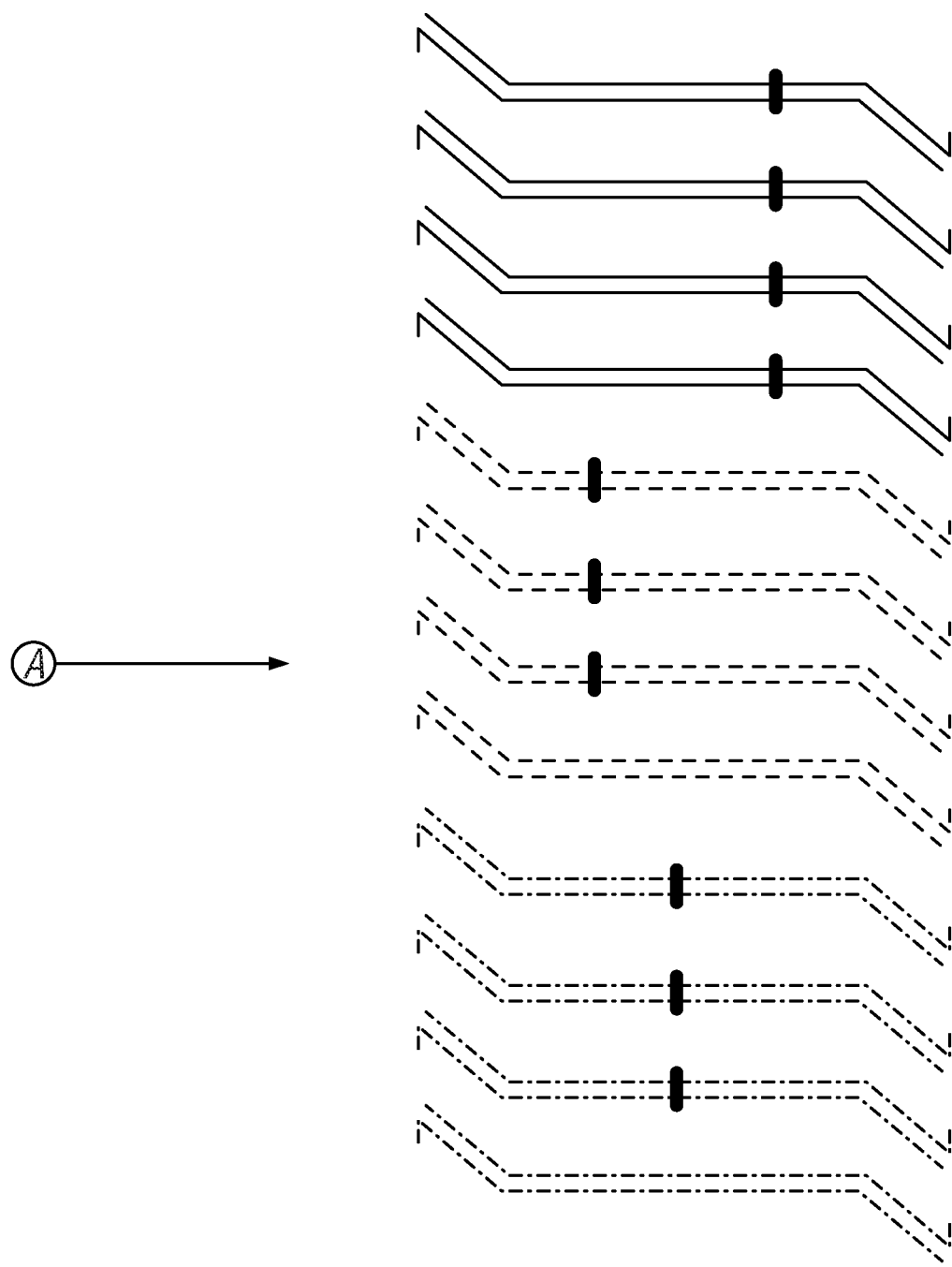
Figure 7:
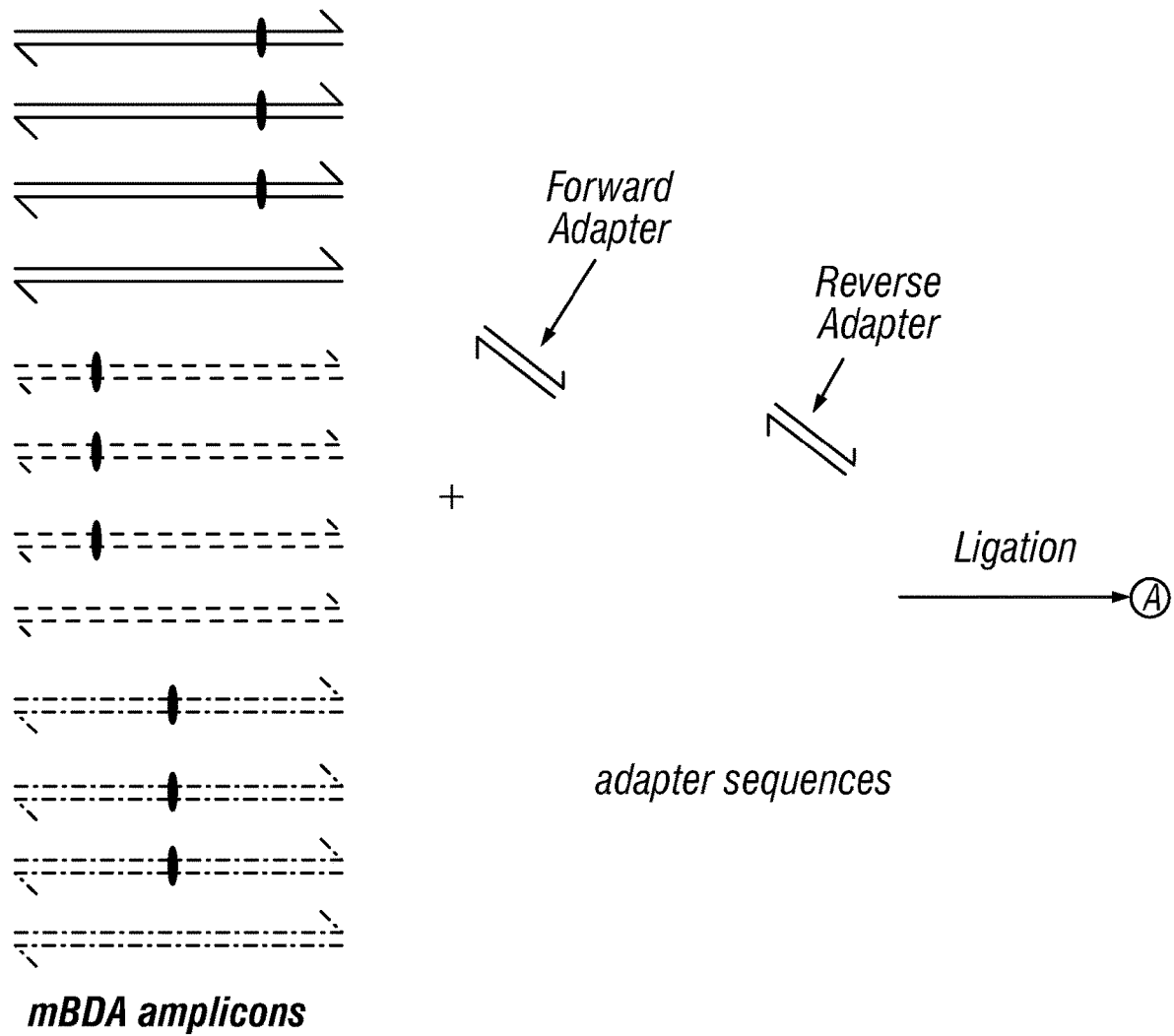
FIG. 7: Alternative ligation-based method for appending adapter sequences onto mBDA amplicons.
Figure 7:
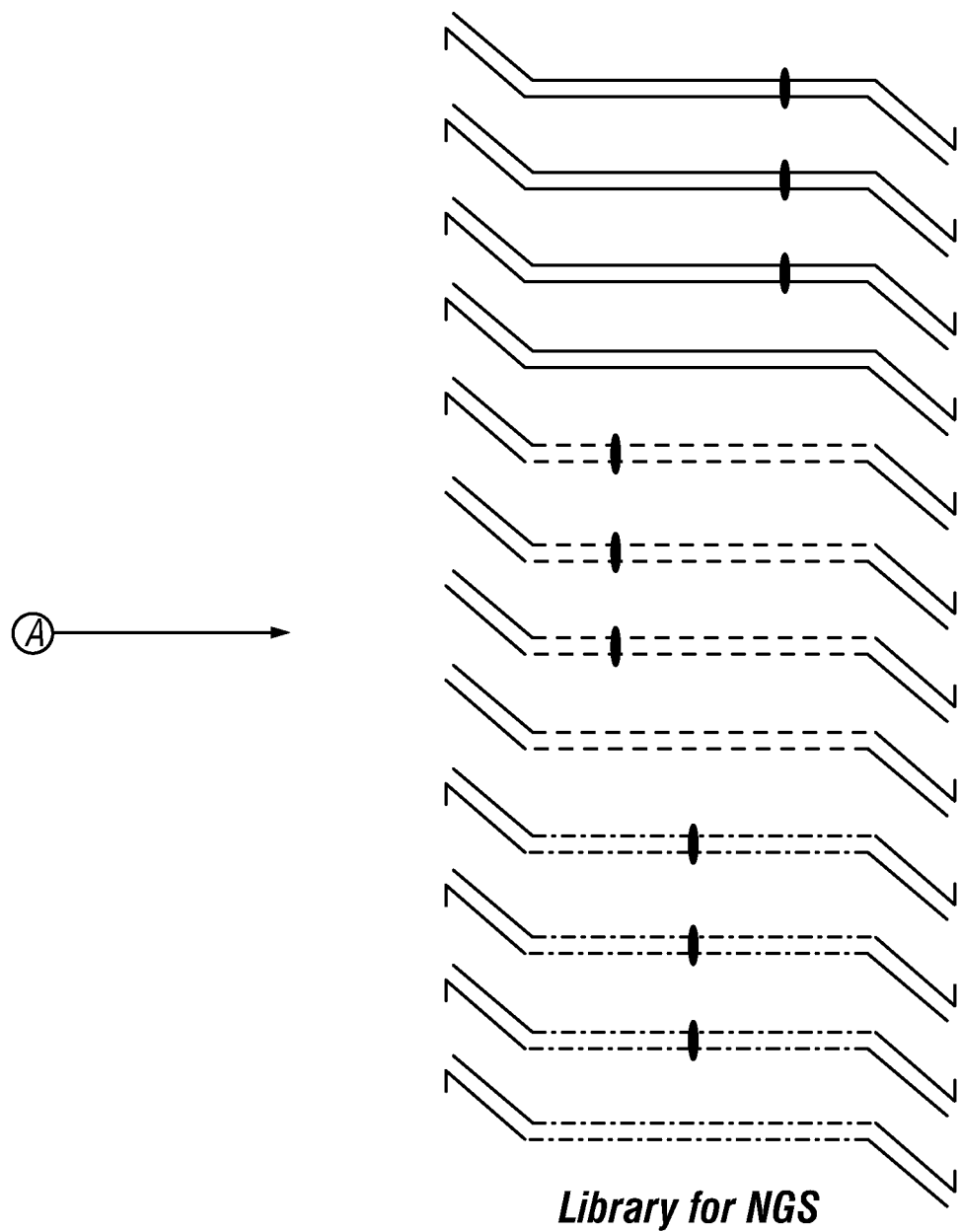

III. OPERATION OF mBDA IN NEXT GENERATION SEQUENCING (NGS) ASSAYS mBDA amplicons can be more precisely analyzed by downstream NGS. Commercial NGS systems (e.g., Illumina, Ion Torrent) require that special adapter sequences flank the sequence of interest (a.k.a. the insert). These can be appended to mBDA amplicons via either PCR or ligation, as shown in FIGS. 3 and 7.

For appending mBDA amplicons by PCR (FIG. 3), adapter primers bearing both universal NGS adapter sequences and gene-specific sequences are introduced to the mBDA amplicon mixture, and 2 or more cycles of PCR results in an amplicon mixture with sequencing adapters appended on either side of each mBDA amplicon. In some embodiments, the mBDA amplicon mixture is purified via size selection to remove primer dimers before appending adapter sequences. In some embodiments, the adapter-appended amplicons are subject to another round of PCR to append sample indexes or other adapter sequences. In some embodiments, the adapter-appended amplicons are subject to further purification or quality control before next-generation sequencing (NGS).

For appending mBDA amplicons by ligation (FIG. 7), the 5' phosphate needed for ligation can be introduced to the mBDA amplicons through use of primers with 5' phosphate modifications, or via kinase after mBDA. Unlike in the PCR method for introducing adapters, only 1 pair of universal adapter sequences is needed. However, this ligation approach requires a purification step to remove excess adapters and unligated amplicons.

NGS analysis of mBDA amplicons offers two significant advantages over NGS analysis of a library constructed from direct multiplex PCR amplification of a sample and that of libraries constructed from ligation and hybrid-capture. First, mBDA enriches rare mutations by 100- to 10,000-fold, allowing sensitive detection of rare sequence variants. All NGS platforms suffer from an intrinsic sequencing error rate that varies between roughly 0.1% (Illumina) and 8% (Oxford Nanopore). Without complex unique molecular identifier barcodes or other technologies to suppress sequencing error rates, the NGS intrinsic error rate limits the analytic sensitivity of NGS to rare mutations. For example, if the NGS error rate is 1%, then out of 1,000 reads to a locus, if 987 are mapped to A, 7 are mapped to T, 2 are mapped to C, and 4 are mapped to G, it would not be clear if a T variant actually exists, or whether the 7 reads mapped to T are simply due to sequencing error. When BDA enriches a T variant from 0.2% VAF to 40% VAF, then the T allele reads can be clearly distinguished against the sequence error background.

Unique molecular identifier (UMI) barcodes have been recently demonstrated to suppress NGS sequencing error, and are used by commercial products such as Roche Avenio and Guardant 360. However, UMIs increase the sequencing reads required (and thereby NGS cost) by roughly 10-fold, and furthermore are difficult to both experimentally implement and bioinformatically interpret.

The second advantage of sequencing mBDA amplicons is that the number of NGS reads required is significantly reduced compared to both standard NGS and NGS with UMIs. For example, a sample that has a particular mutation at 1% VAF may require 500 reads for standard NGS (5 reads out of 500), and 5000 reads for NGS with UMIs, but after mBDA enrichment to >80% VAF, just 10 reads is likely sufficient for a confident call of a positive detection of the said mutation.

NGS analysis of mBDA amplicons can also be used to inform adjustments of primer concentrations to achieve more uniform amplification of all mBDA amplicons. Different primer sequences bind to their respective targets with kinetics that can vary by more three orders of magnitude, and currently even the best biophysical models and machine learning algorithms are unable to predict primer binding rate constants with better than about 90% accuracy. Consequently, an initial design of mBDA oligos using the same concentrations for all fP and rP species will likely result in significant bias of reads, with some amplicons being sequenced to perhaps 10-fold higher depth than others.

The reads mapped to each mBDA amplicon in an initial NGS run can be used to inform the adjustment of fP and rP concentrations. Because the concentration ratio of fP and B should be maintained as a constant to achieve reproducible fold-enrichment of sequence variants, it is preferable to adjust rP concentrations based on observed reads. Experimentally, using $[rP]_{new}=[rP]_{old}*(Reads\_median/Reads\_amplicon)^X$ works well, where $[rP]_{old}$ is the previous concentration of the reverse primer, Reads_median is the median reads mapped to each amplicon, Reads_amplicon is the reads mapped to the amplicon corresponding to said reverse primer, and X is a constant adjustment factor. For different NGS library preparation protocols, the optimal value of X may be 0.33, 0.5, or some other value between 0.25 and 1.

IV. INTERPRETATION OF NGS RESULTS THAT UTILIZE mBDA ENRICHMENT

One embodiment of an algorithm to analyze NGS reads from FASTQ files is described below. Similar algorithms from FASTQ or SAM files can similarly be constructed by one of ordinary skill in the art of bioinformatic processing of NGS reads.

1. Trim off adapter sequences or parts of adapter sequences, if any, from all reads.
2. Remove reads with low quality score (e.g., median Q across <30).
3. Align trimmed sequences to reference amplicon sequence list, obtaining a sam/bam file. Alignment may be either end-to-end alignment to amplicon sequences with adapter sequences on both sides, or local alignment to the original mBDA amplicon sequences.
4. Clip the read sequence to the enrichment region of the relevant mBDA blocker, using the pileup column or through nearby conserved sequences.
5. Check the quality of the read at the enrichment loci, discarding the read if the Q score is <30 at the loci of interest. Alternatively, if paired end sequencing is allowed, discarding the paired reads if they disagree with each other at the loci of interest.
6. Tabulate the number of reads mapped to the wildtype amplicon sequence, and any expected variant sequences, and other variant sequences.

From the above algorithm, a reads fraction (RF) is calculated for each mBDA amplicon. Given RF and an estimate on the fold-enrichment (E) achieved by mBDA for that locus/variant, the VAF of the variant in the initial sample can be estimated via $VAF=RF/(E*(1-RF)+RF)$. Because of the NGS intrinsic error issues discusses previously, the user may wish to discard consideration of variants with RF below a threshold (e.g., 1%).

V. APPLICATION CONSIDERATIONS FOR NONINVASIVE CANCER PROFILING VIA CELL-FREE DNA IN PLASMA

Cell-free DNA (cfDNA) in plasma are derived from dying cells (due to apoptosis, necrosis, or immune system attack).

Because cfDNA is cleared from the bloodstream via the kidneys with a reported half-life of between 10 and 60 minutes, cfDNA offers a snapshot in time of the body. Numerous studies have shown that tumor-derived cfDNA detected in patients consistently provides similar mutation profiles as biopsy samples. Because cfDNA requires only a minimally invasive blood draw, rather than invasive biopsies that risks infection, cfDNA analyses have also been referred to as liquid biopsies.

Unlike DNA derived from tumor samples, however, cfDNA is much shorter, with an average length of between 160 and 180 nt. Because the breakpoints for cfDNA are more or less uniformly distributed, use of longer amplicons risks losing sensitivity. For example, if the average length of cfDNA is 160 nt, and the length of a mBDA amplicon is 120 nt, then only about 1 in 4 cfDNA molecules bearing an enrichment locus of interest will have a breakpoint outside the amplicon and be amplifiable. For this reason, mBDA fP and rP sequences should be designed such that all amplicons are shorter than 120 nt, and preferably shorter than 90 nt.

On the other hand, the short length of cfDNA means that the risk of unintended longer amplification products, e.g., from rP species from different BDA systems, is essentially nonexistent. This means that for mBDA oligo sets designed for cfDNA analysis, the design constraint of having all BDA systems close to each other target the same (+) or (−) template strand does not apply, allowing more options for B sequence selection.

VI. APPLICATION CONSIDERATIONS FOR CELL LINE CONTAMINATION ASSAYS

Human cell line samples are used both by academic and industry research laboratories, and by cell therapy providers (e.g., stem cell therapy or autologous CAR-T therapy). Potential cell contamination is a significant concern for these industries, because it could lead to incorrect scientific conclusions for research and immune reactions leading to adverse patient outcomes for therapeutics.

The cell contamination detection problem can be classified into two primary cases: (1) problems where the base (desired cell) genotype is known, but the contaminant is unknown, or (2) problems where the contaminant genotype is known, but the base genotype is unknown. In both classes of problems, mBDA can be used to enrich for nonpathogenic single nucleotide polymorphisms (SNPs).

Figure 9:
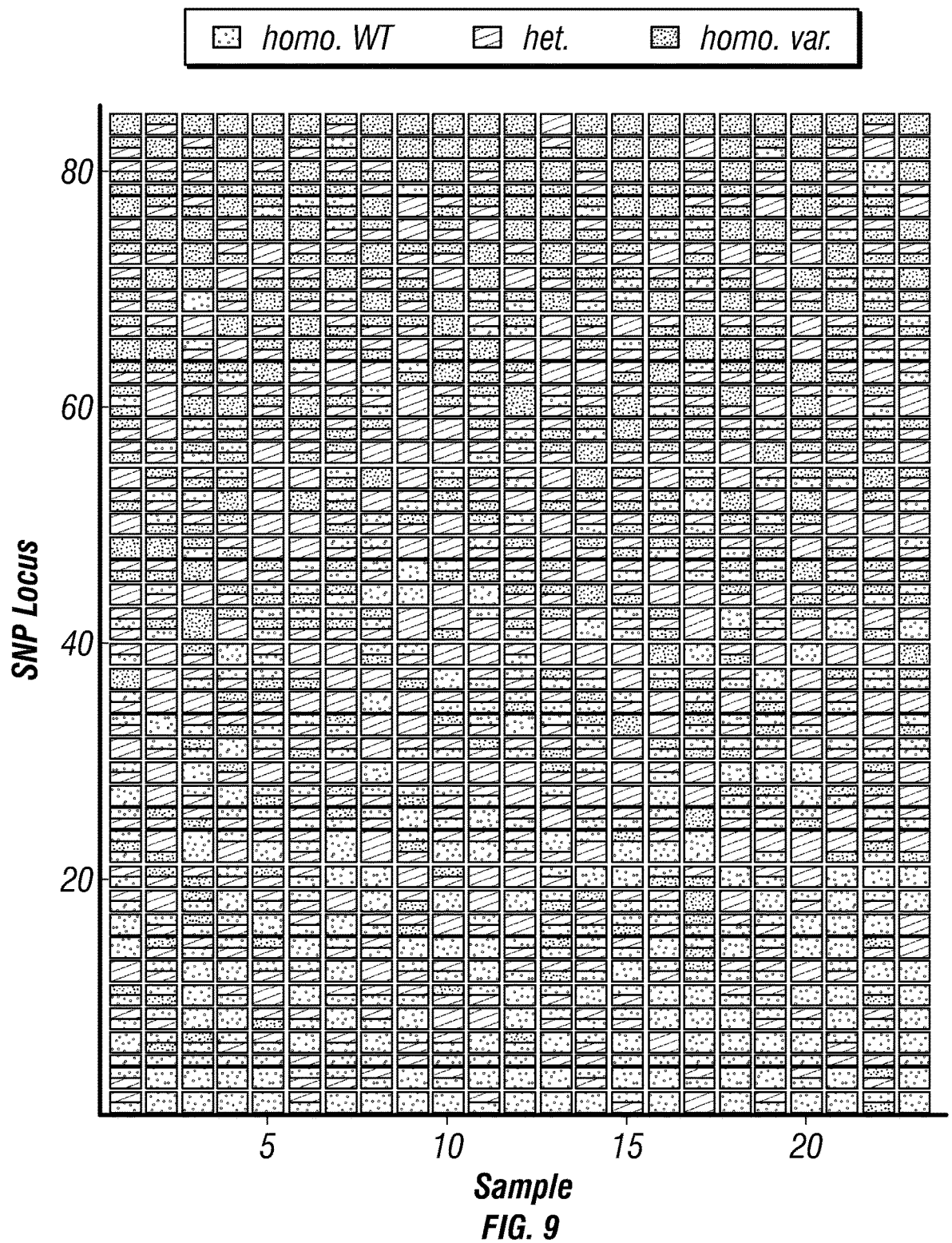
FIG. 9: Patterns of SNPs across 85 SNP loci for 23 individuals (volunteers from the Houston area).

Traditionally, criminal forensics and other fields use short tandem repeat (STR) profiling for determining genomic identity, but STR profiling requires electrophoresis and is not convenient to do in a high throughput manner, and furthermore has limited sensitivity. A panel of roughly 80 SNPs, each selected so that a variant allele has a population frequency between 5% and 95%, is with high probability capable of distinguish any two non-identical genomes. FIG. 9 shows the SNP genotype profiles of 23 individuals (volunteers from the Houston area). For any pair of individuals, there are on average more than 25 SNP allele differences out of the 85 characterized, and always more than 15 for all pairs analyzed. Mathematics suggests that any two people alive in the world today would still likely be different in at least 6 of the 85 SNPs profiled. Thus, nonpathogenic SNPs can serve as reliable markers of genomic identity.

For the first class of problems (known base genotype, Case 1), which is more relevant to cell therapy facilities, mBDA oligos can be designed to selectively block the amplification of all homozygous SNP alleles specific to the base genotype (FIG. 8). In other words, mBDA blockers are designed to suppress the homozygous SNP alleles of the base cell line. The amplification and detection of any alternative allele in any of the mBDA systems would suggest a contamination. Importantly, this method does not require prior knowledge of contaminant genotype and should be generally applicable to all contaminants that are not genetically identical to the base. Assuming that the contaminant cell line is not identical to the base cell line in the panel of SNPs profiled, there will be at least 1 SNP locus that is not suppressed by the blocker and will amplify very efficiently. This results in both an alternative allele in NGS data, and a shift to a lower Ct value in qPCR; both can be used for cell line contamination detection. There is a small probability that the contaminant has the same SNP alleles within the panel observed, but this probability exponentially decreases with the number of SNP sites characterized, and is expected to be very small for a panel of 80 SNPs.

The second class of problems (known contaminant genotype, Case 1) is more relevant to academic research labs, where HeLa cells are known to be a primary contaminant. Although it is of course possible to perform genomic profiling of the base cell line, doing so may be inconvenient or too costly for cell lines that see only limited use as part of a larger set of experiments. Cellular contamination can be detected based on only the SNP allele profile of the contaminant, without knowledge of the base SNP genotype (FIG. 8). mBDA oligos can be designed to suppress SNP alleles other than the ones present in the contaminant genome. Thus, presence of the contaminant would mean that all mBDA amplicons will show contaminant-specific SNPs. At loci where the contaminant is heterozygous, either allele may be blocked. Assuming that the base cell line is not identical to the contaminant in the panel of the SNPs profiled, a lack of contamination means that some of the blockers will suppress amplification. In contrast, if there is contamination, all alternative alleles will be efficiently amplified, and the Ct value of a qPCR reaction will be low.

There is also a third case of cell contamination detection, in which the SNP genotypes of both the base and the contaminant are known. This is a relatively easier problem that can be solved by single-plex BDA (see U.S. Patent Appln. Publn. No. 2017/0067090, which is incorporated herein by reference in its entirety for all purposes).

Figure 10:
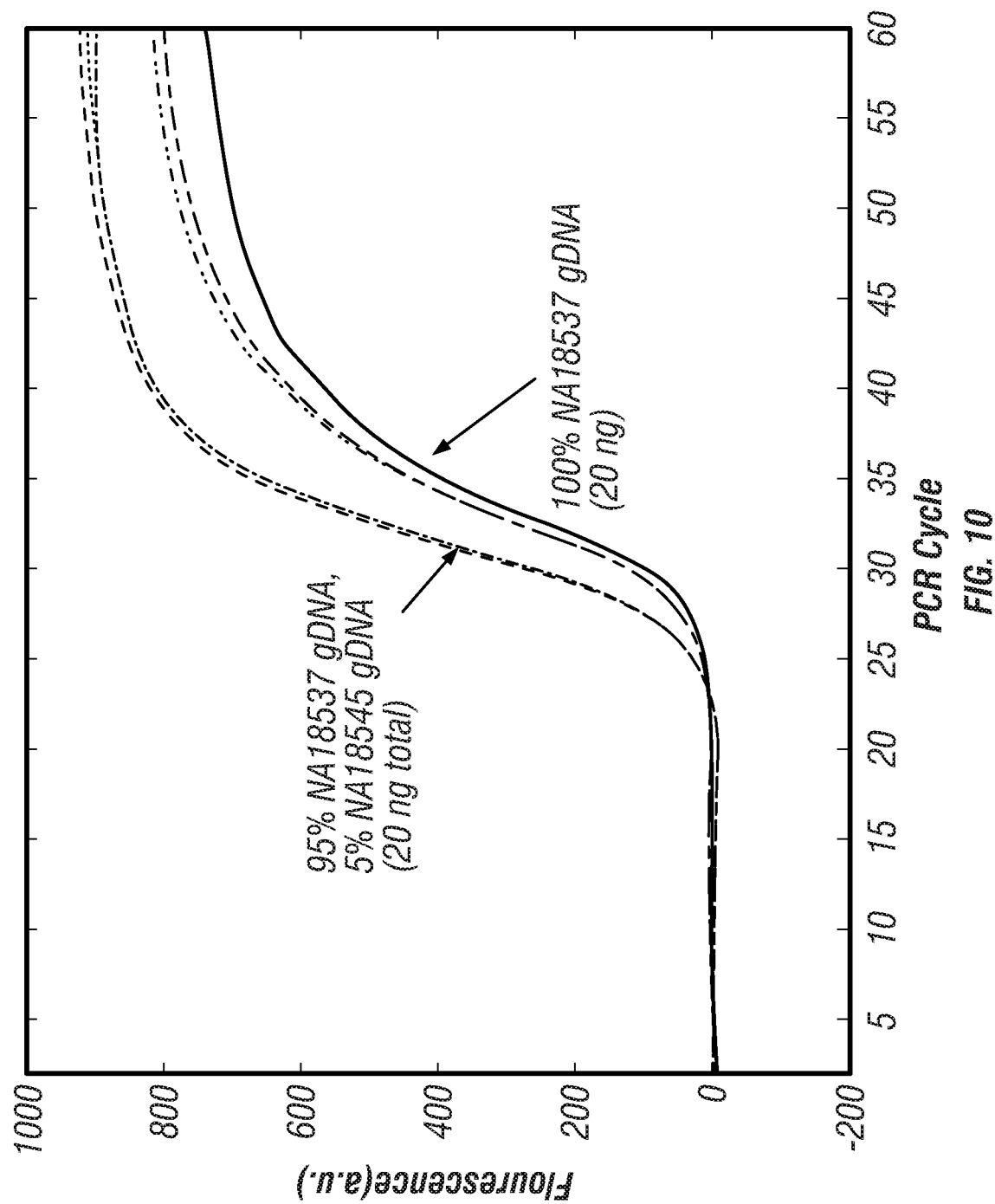
FIG. 10: Cell line contamination detection using 80-plex mBDA and qPCR readout.
Figure 10:
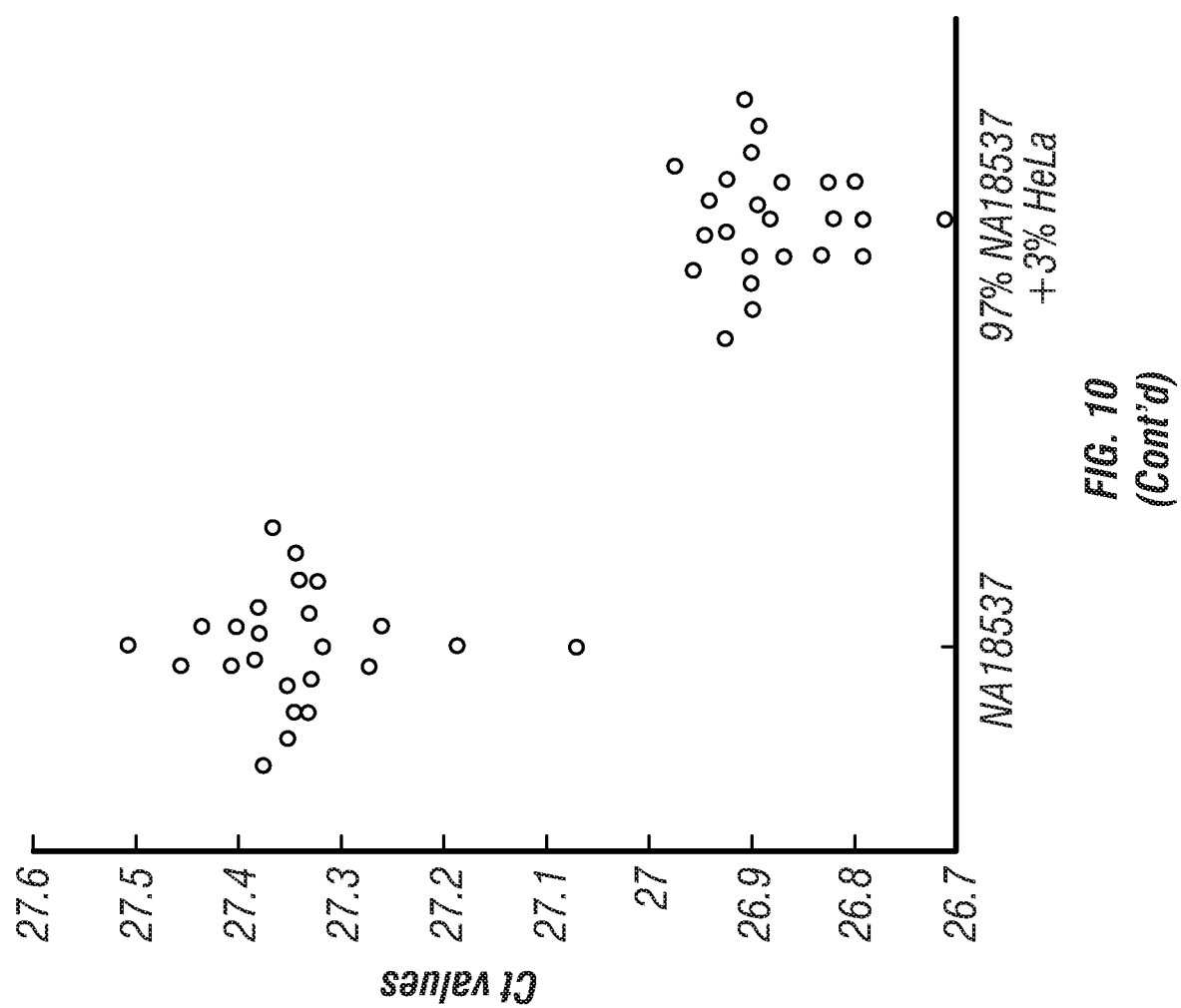

In some embodiments of the cellular contamination detection application of mBDA, qPCR is used as the readout. FIG. 10 shows results in which the NA18537 human cell line gDNA serves as the base. An 80-plex BDA system was designed to block homozygous SNP alleles of NA18537. Two different contaminants, NA18562 and HeLa, were tested at 5% and 3%, respectively. In both cases, qPCR showed an observable decrease in Ct for the contaminated samples vs. the pure NA18537 samples. In other embodiments of the cellular contamination detection application of mBDA, NGS can be used as the readout. Doing so should also provide reliable detection of cellular contamination at a less than 0.1% VAF limit of detection.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—NGS Experimental Results

Figure 4:
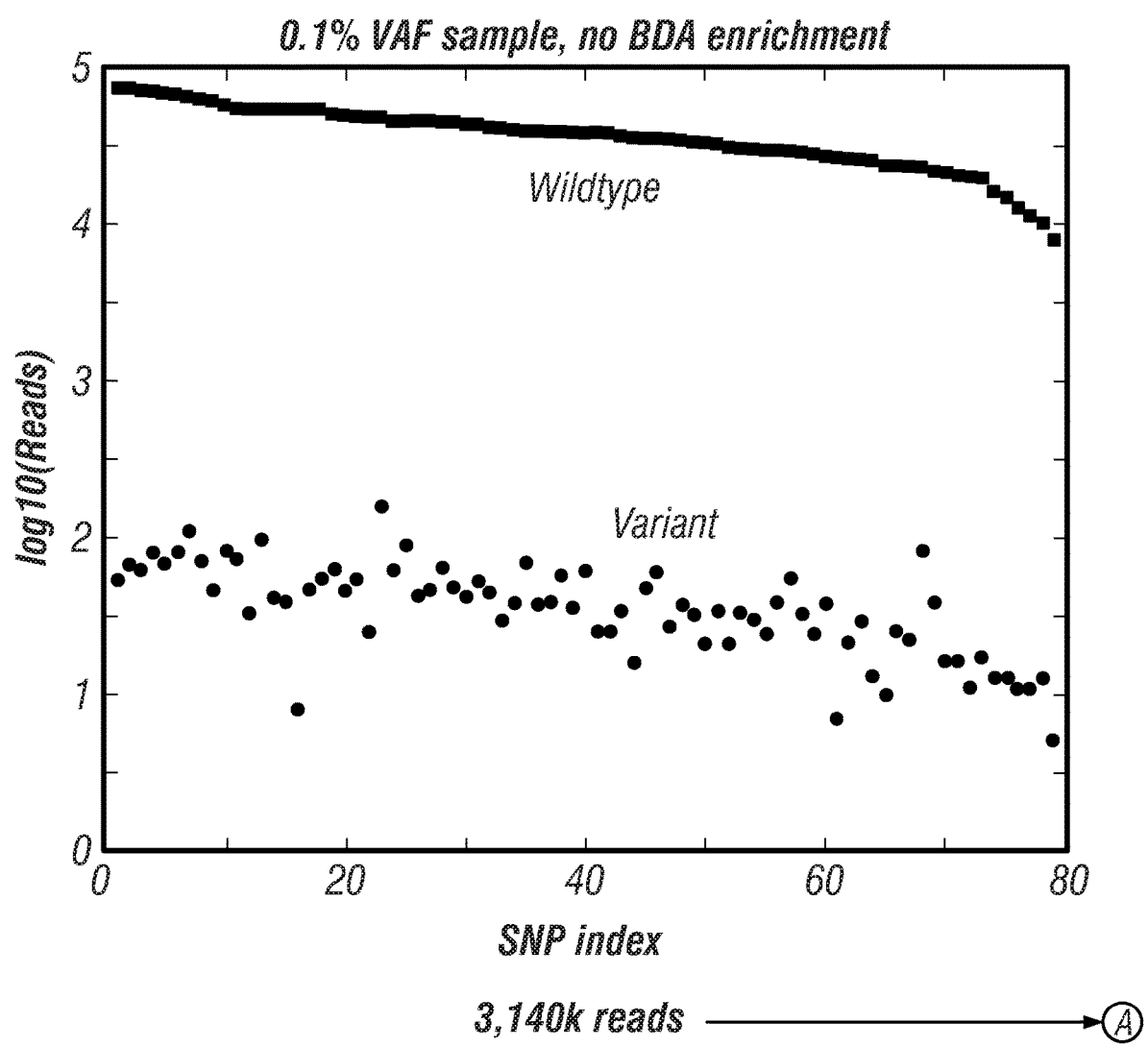
FIG. 4: Summary of NGS experimental results.
Figure 4:
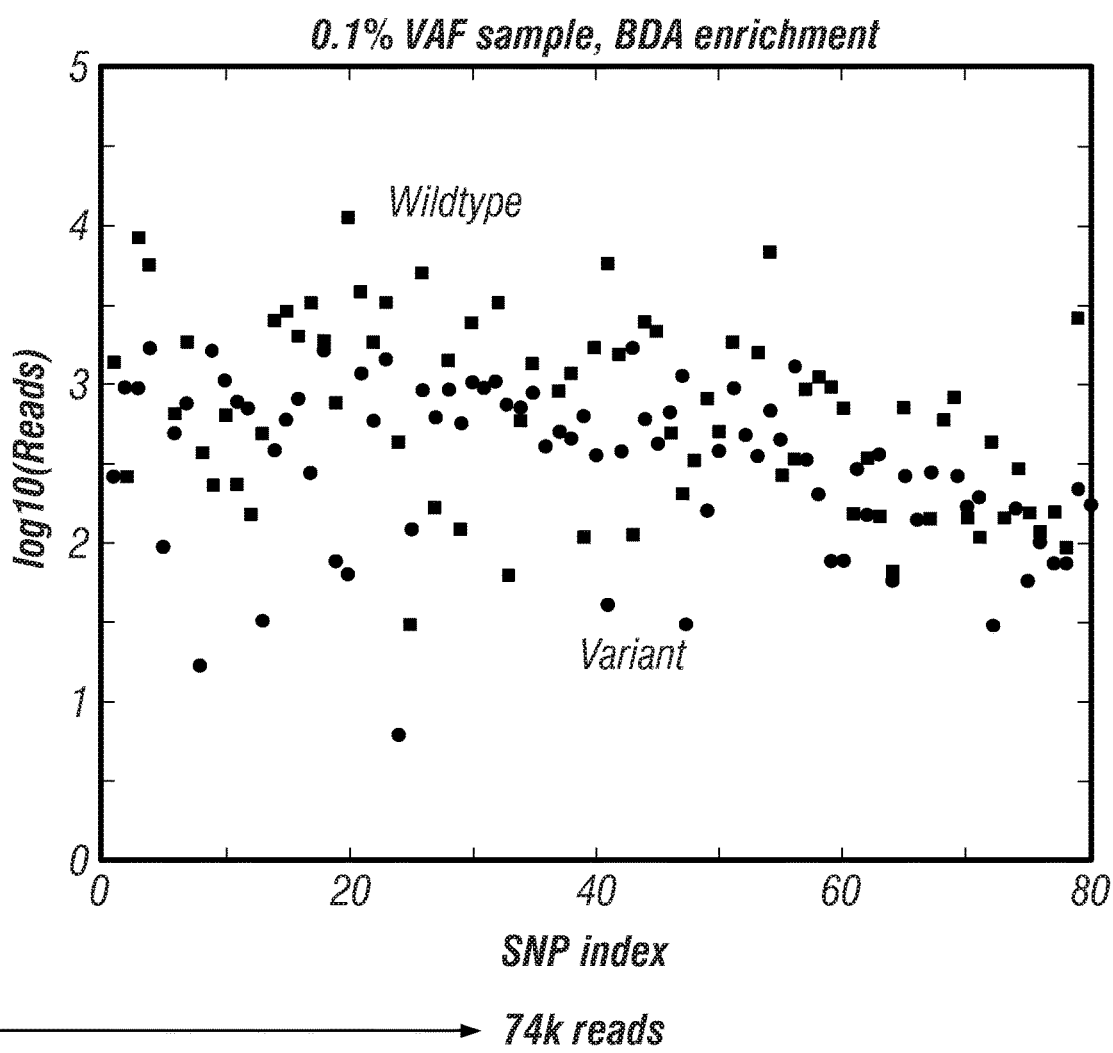
Figure 4:
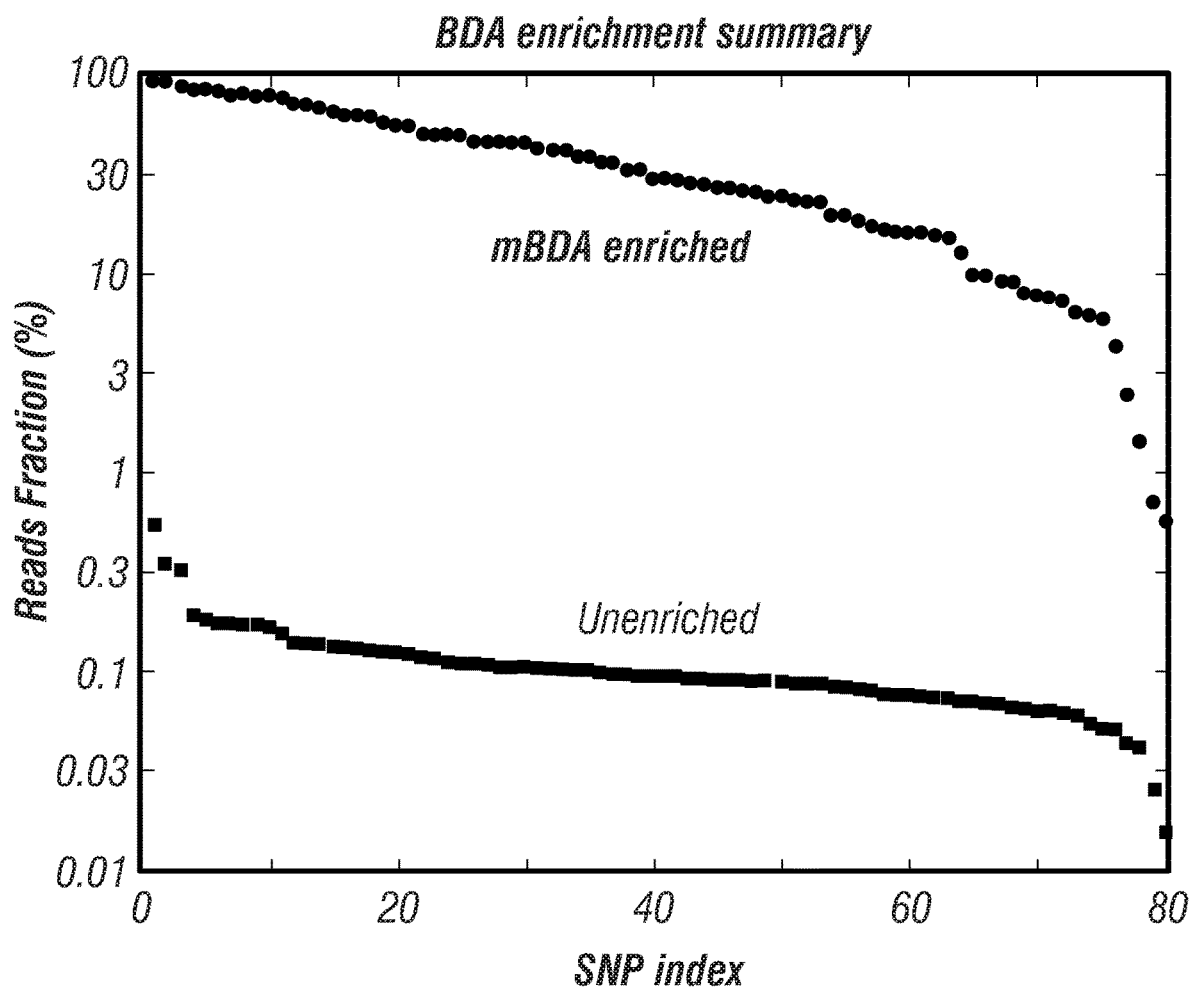

A cell line genomic DNA sample was constructed by mixing 99.9% NA18537 and 0.1% NA18562 (50 ng total). The left panel of FIG. 4 shows the number of reads mapped to the wildtype (NA18537) and variant (NA18562) alleles for each of 80 loci, following a standard 80-plex amplicon sequencing. The number of reads mapped to the variant allele is roughly 1000-fold lower than for the wildtype allele for all loci, consistent with expectations. The middle panel of FIG. 4 shows the number of reads mapped to the wildtype and variant alleles for each of the 80 loci following 80-plex mBDA. The number of reads mapped to the variant alleles is now comparable to the number of reads mapped to the wildtype alleles. Importantly, all variant alleles were sequenced at comparable or higher depth than the unenriched library, but the total number of NGS reads used is 40-fold lower. This represents a potential 40-fold savings in NGS analysis of complex DNA samples. The right panel of FIG. 4 shows the fraction of reads mapped to the variant allele with and without mBDA enrichment.

Example 2—Inferring initial VAF from post-mBDA NGS reads

Figure 6A:
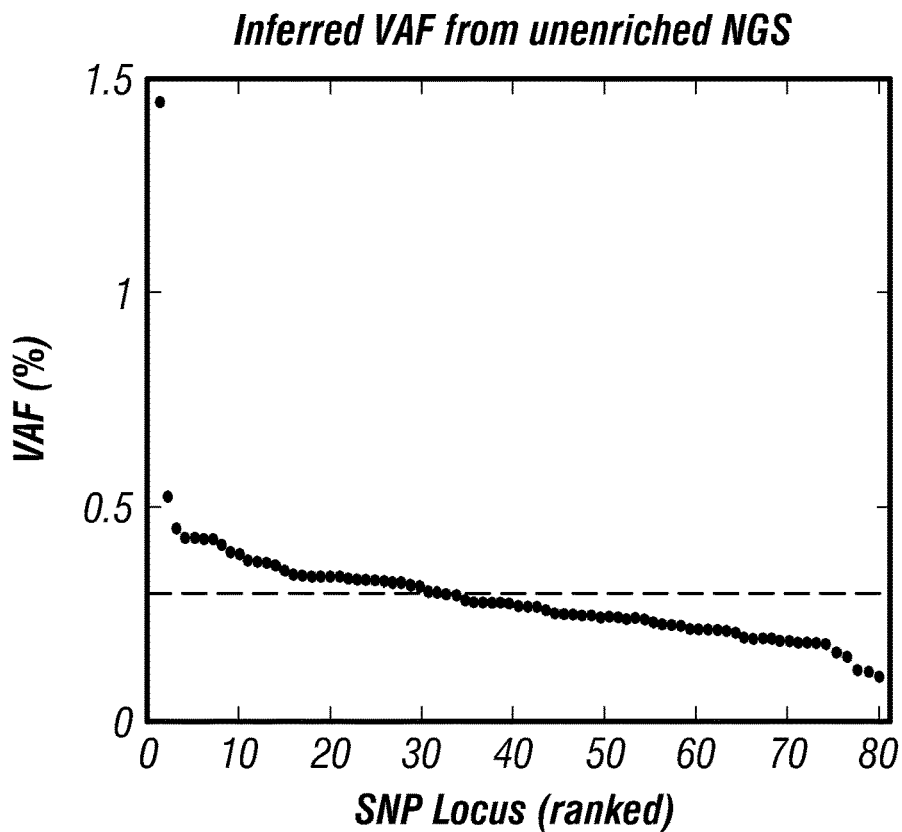
FIGS. 6A-D: Inferring initial VAF from post-mBDA NGS reads.
Figure 6B:
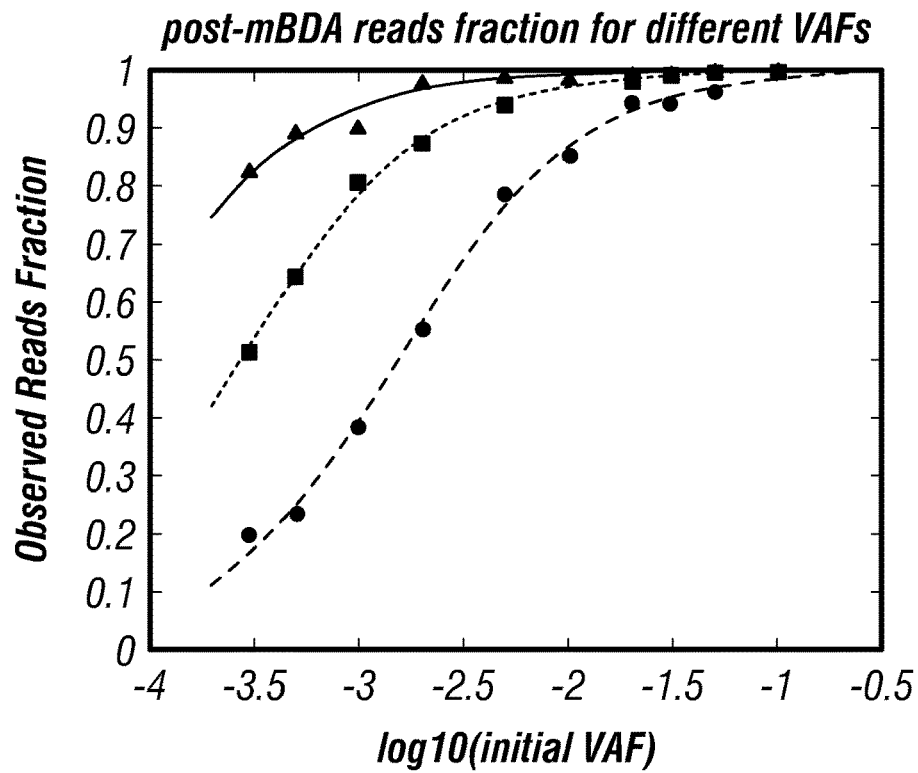
Figure 6C:
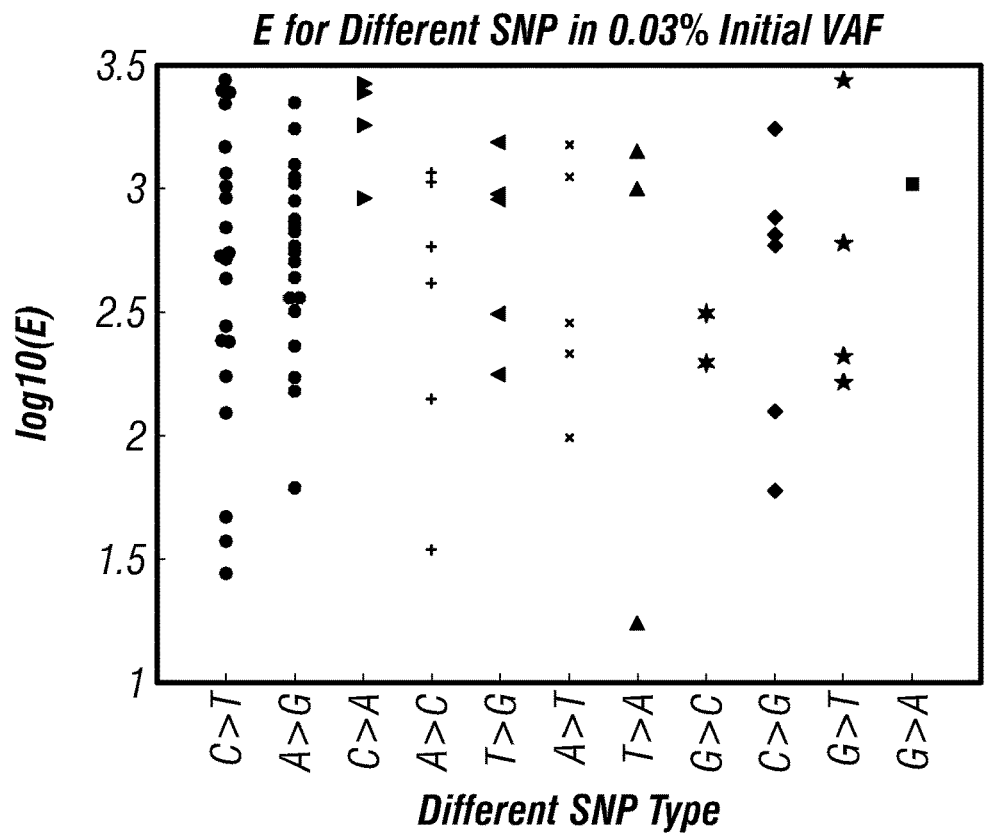
Figure 6D:
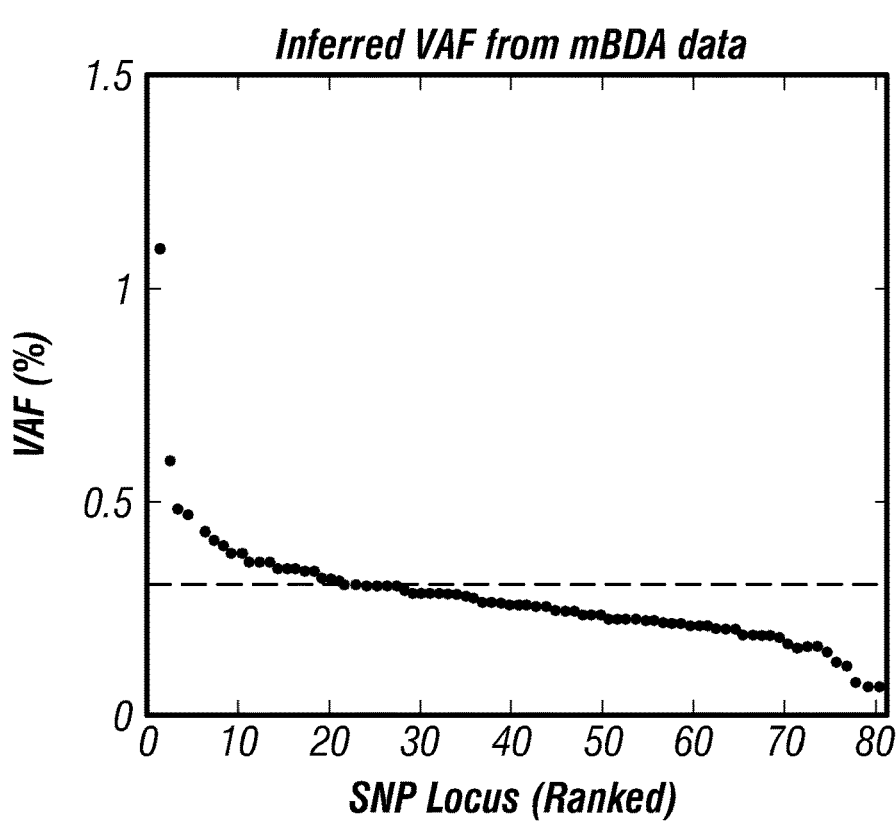

FIG. 6A shows the inference of VAF from unenriched multiplex PCR library, based on fraction of reads mapped to variant allele at each locus. The dashed horizontal line shows the expected 0.1% VAF; inferred VAF varies slightly from the expected due to NGS sequencing bias. FIG. 6B shows the relationship between initial VAF and post-mBDA NGS reads fraction mapped to variant allele. Different variants at different loci have different fold-enrichment E, but the relationship between the reads fraction and the VAF are as expected (sigmoidal line shows expectation based on theory and best-fit fold enrichment E). Here, all input samples were 50 ng of genomic DNA, and subject to 23 cycles of mBDA. FIG. 6C provides a summary of fold enrichment E for different SNP types. There does not appear to be significant sequence bias on E. FIG. 6D shows the inferred VAF from reads fraction (from post-mBDA NGS) and fitted E values. The inferred VAF values show a similar distribution as those based on direct analysis of multiplex PCR NGS.

Example 3—Using mBDA to Detect Variant DNA Sequences with Low Variant Allele Frequency (VAF) Using Low-Depth Next-Generation Sequencing (NGS)

Figure 13A:
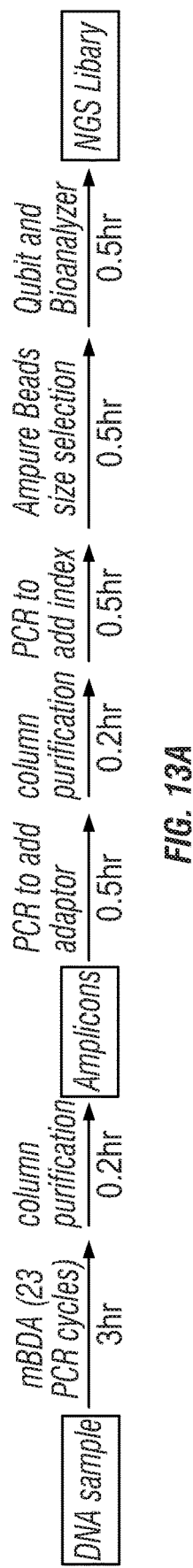
FIGS. 13A-E: Using mBDA to detect variant DNA sequences with low variant allele frequency (VAF) using low-depth next-generation sequencing (NGS).
Figure 13B:
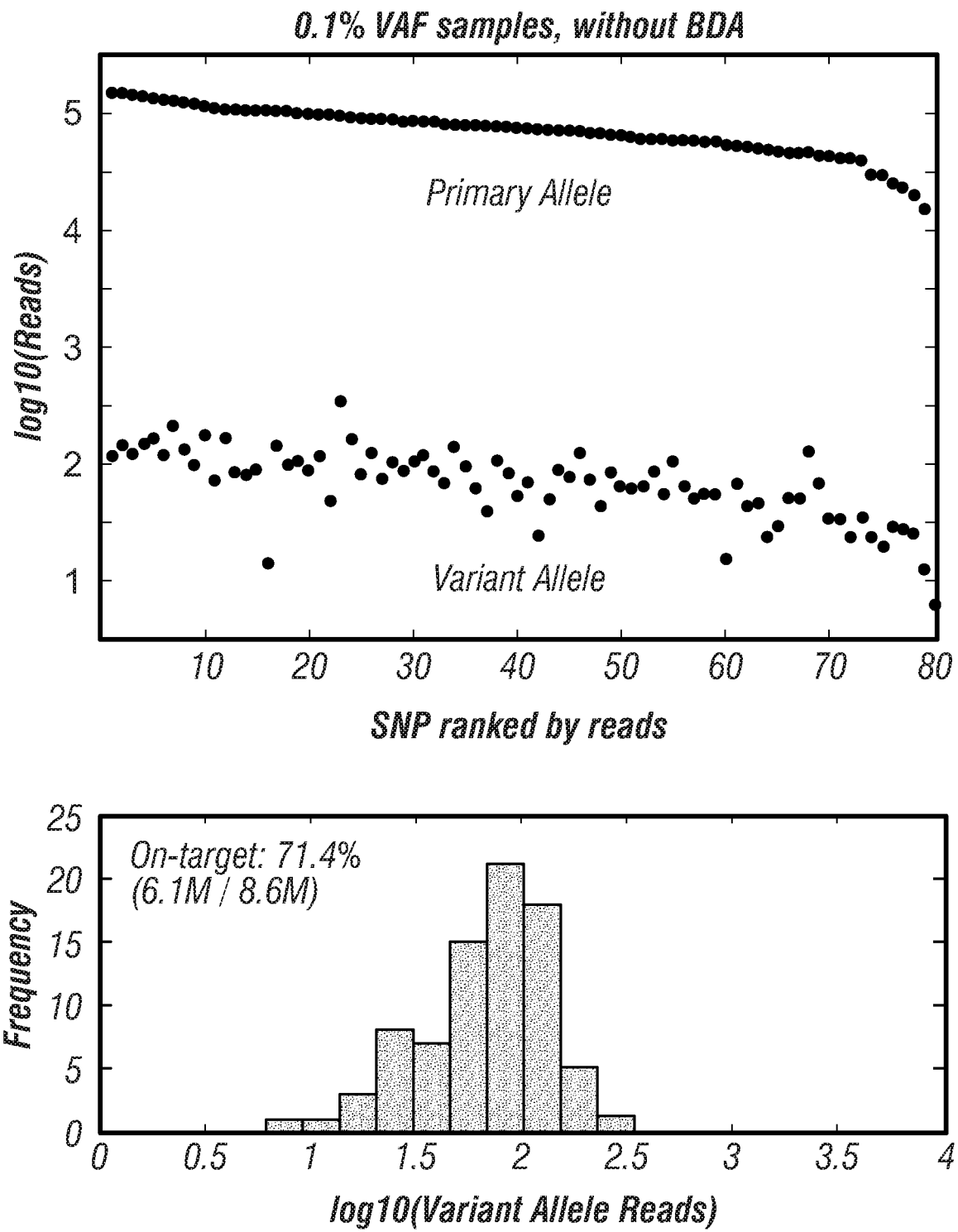
Figure 13C:
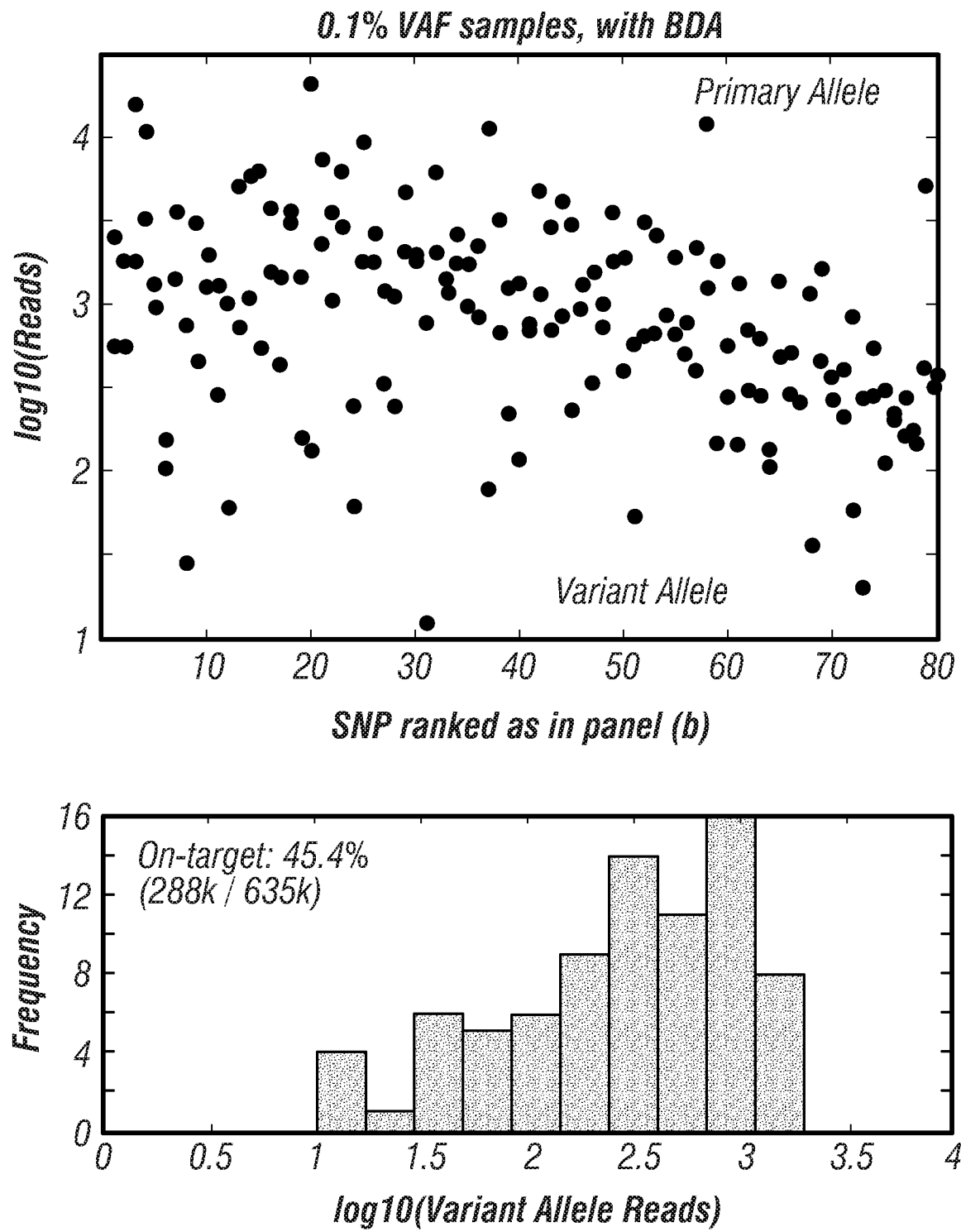
Figure 13D:
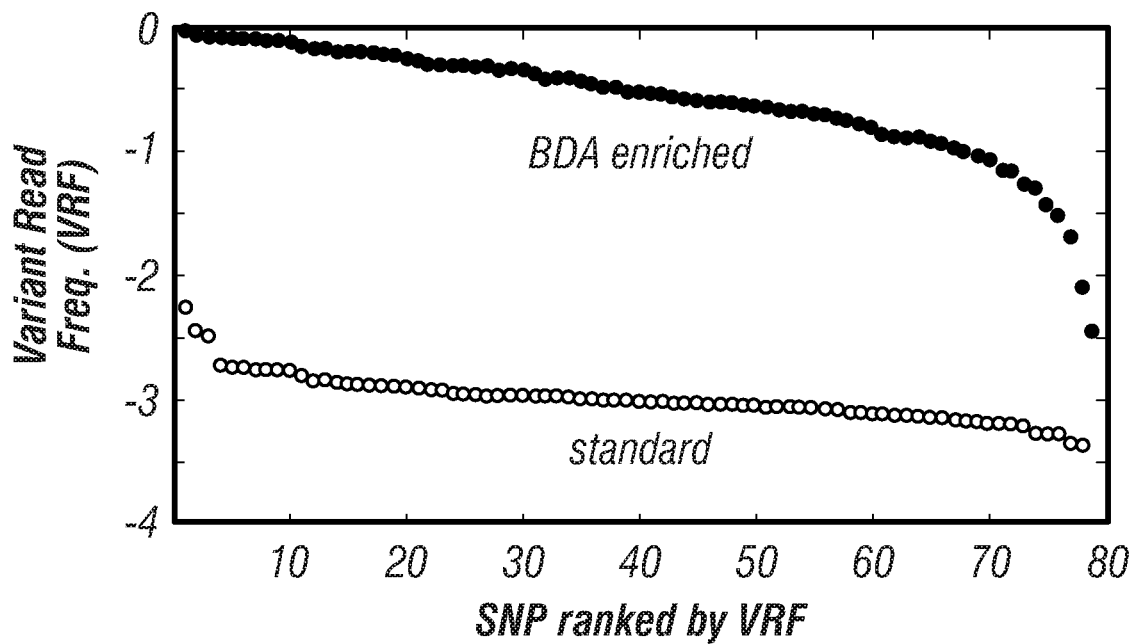
Figure 13E:
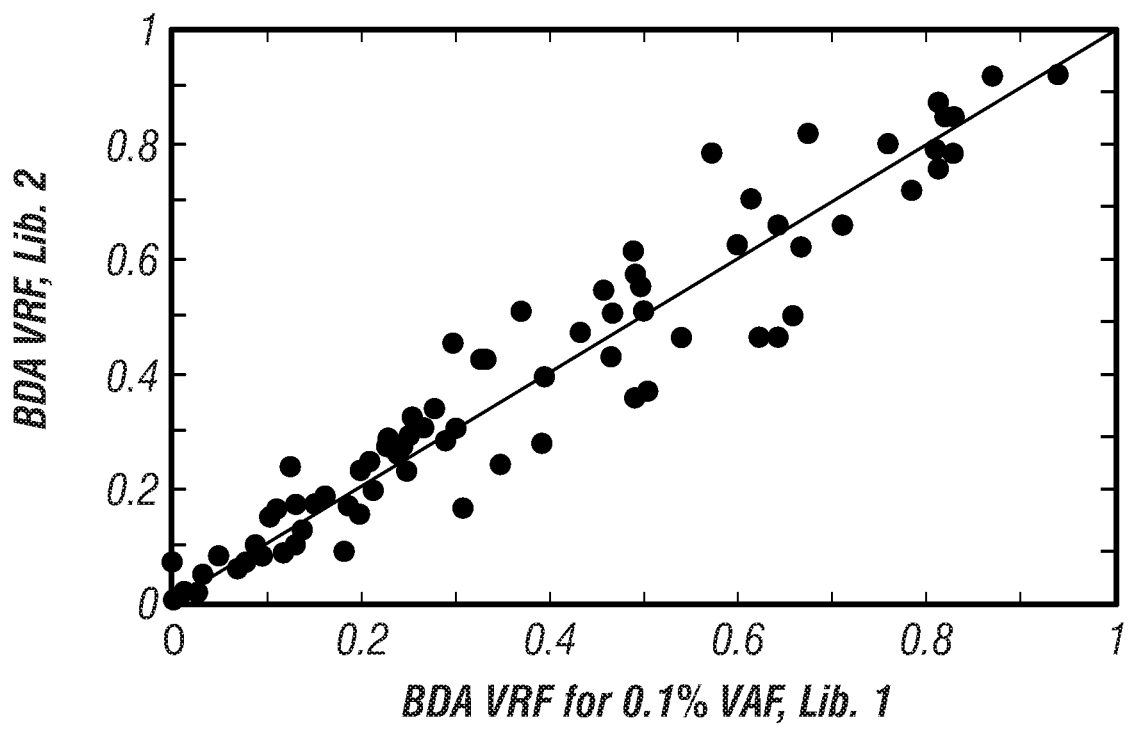

A summary of the mBDA NGS library preparation workflow is shown in FIG. 13A. And a summary of NGS results on an amplicon library without using mBDA are shown in FIG. 13B. Here, the sample was 50 ng of a 99.9%:0.1% mixture of NA18537 and NA18562. The 80 SNPs were selected such that NA18537 and NA18562 are homozygous for different alleles. 8.6 million NGS reads were used for this library, in order to ensure at least 5× sequencing depth on the variant alleles. Note that such standard amplicon sequencing is unable to confidently call variants at 0.1% VAF, due to the existence of NGS intrinsic error (see FIG. 14E). A summary of NGS results for the mBDA NGS library on the sample 0.1% VAF sample are provided in FIG. 13C. Compared to the library in panel (FIG. 13B), 13-fold fewer NGS reads were used, but the all variant alleles were sequenced to at least 10× depth. Thus, mBDA reduces the NGS required for rare variant profiling by at least a factor of 25. A summary of the variant read fraction (VRF) for each SNP locus in the libraries described in panels (FIG. 13B) and (FIG. 13C) are provided in FIG. 13D. The standard amplicon NGS library shows roughly 0.1% median VRF, as expected. The mBDA NGS library exhibits roughly 30% median VRF, indicating that variant SNP alleles are enriched typically by 300-fold. The reproducibility of the VRFs in two replicate mBDA NGS libraries using the 0.1% VAF sample is shown in FIG. 13E.

Example 4—Quantitating Variant VAFs Based on mBDA NGS VRF

Figure 14B:
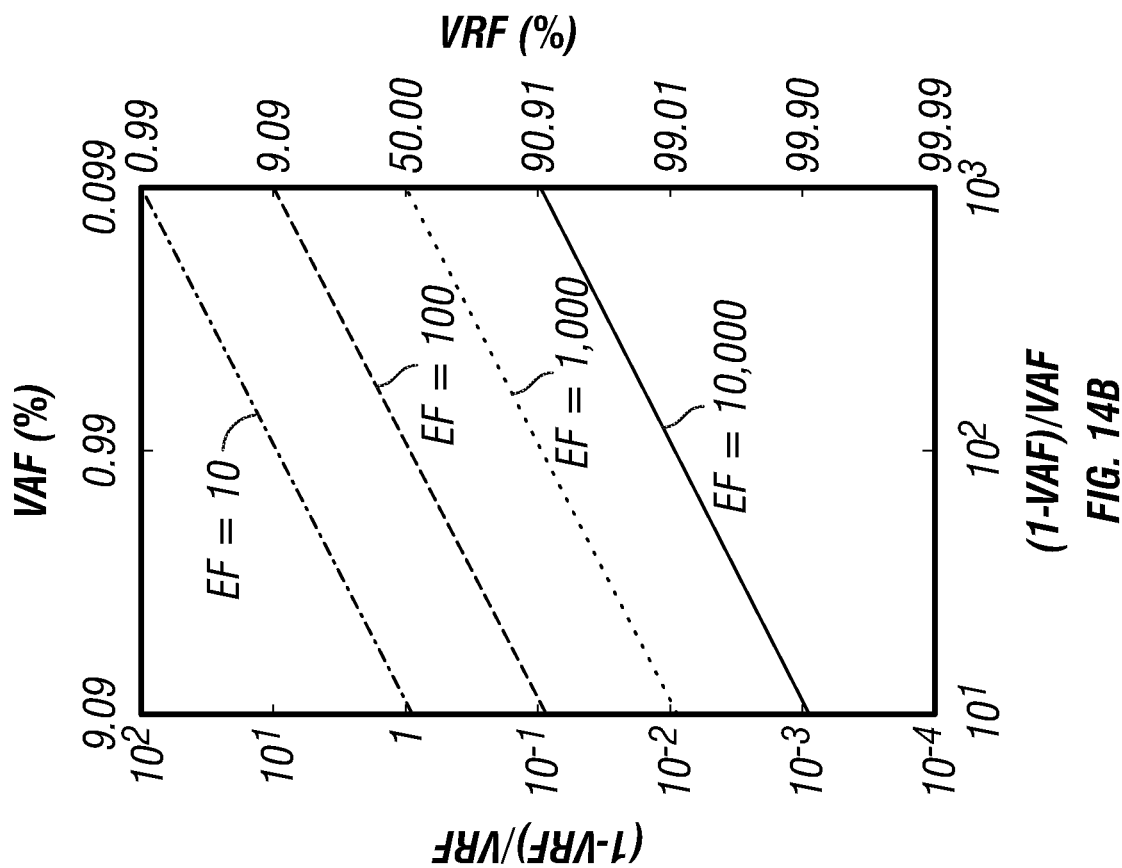
FIGS. 14A-E: Quantitating variant VAFs based on mBDA NGS VRF.
Figure 14A:
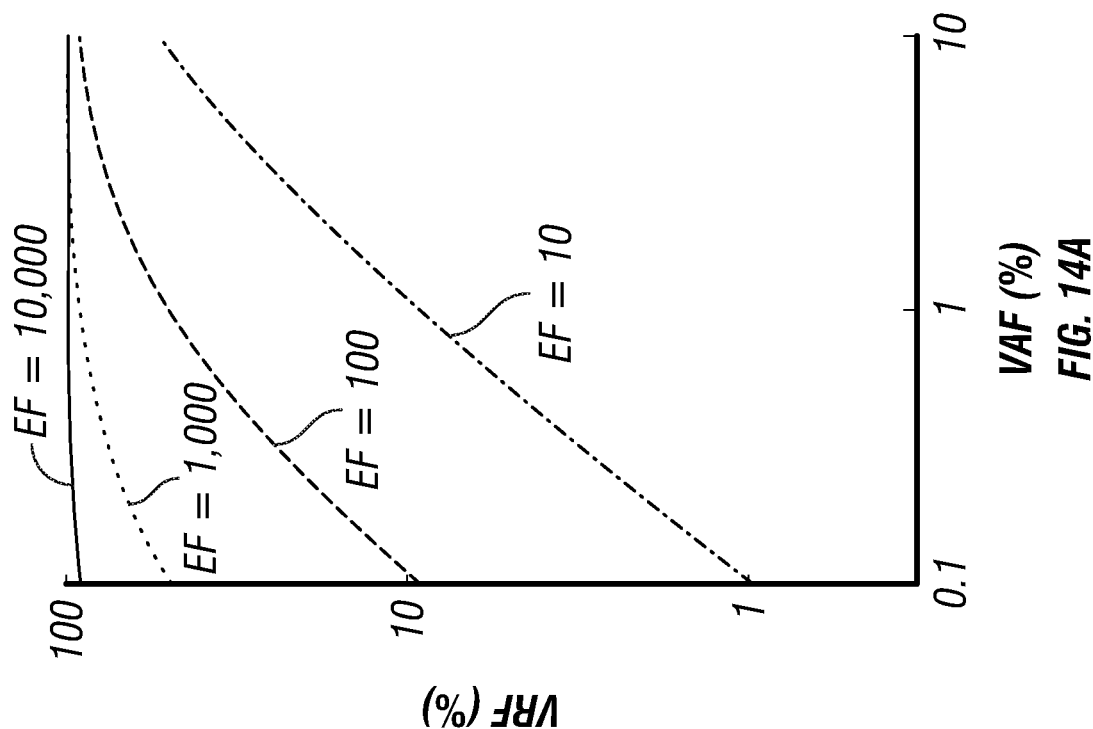
Figure 14C:
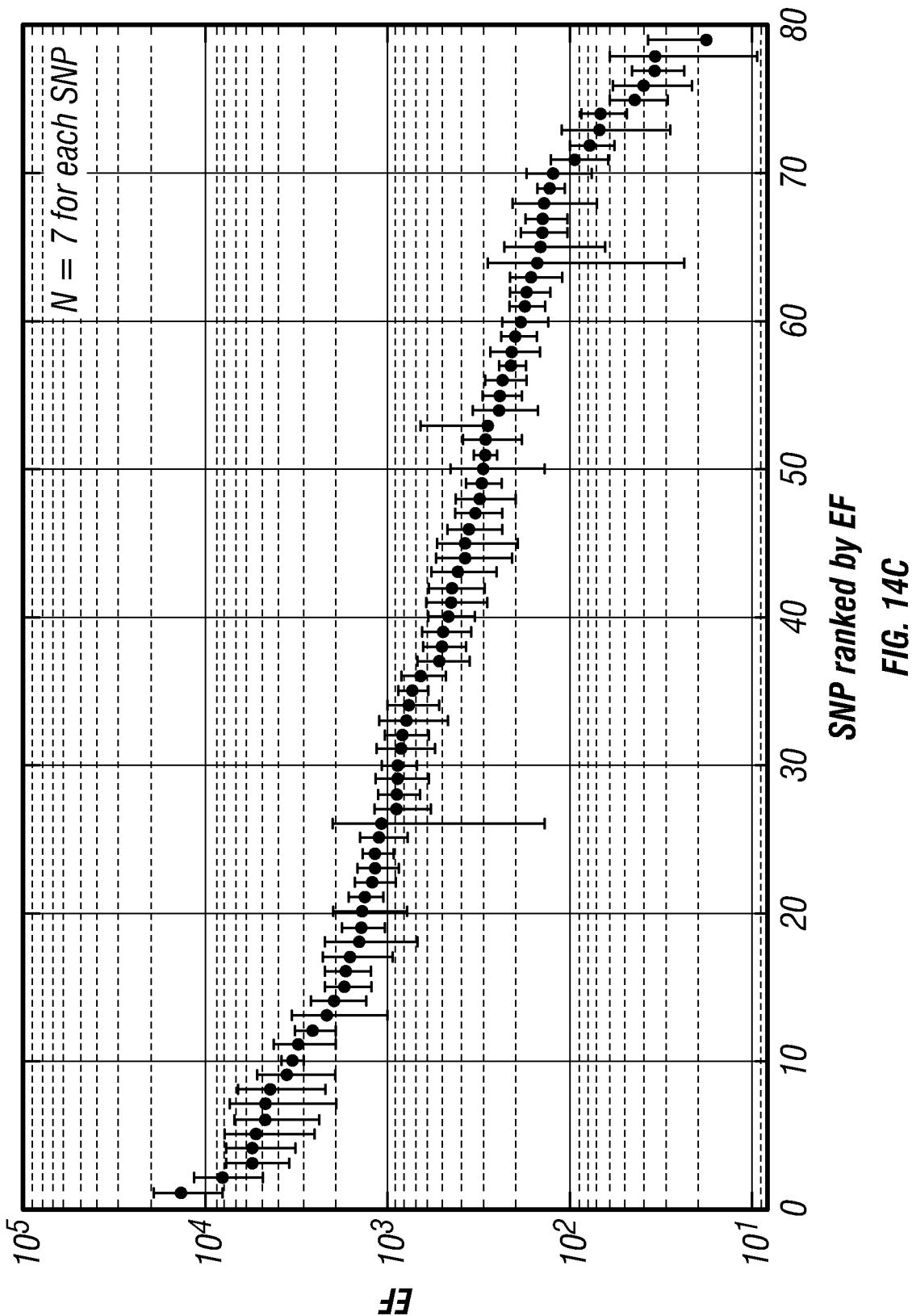
Figure 14D:
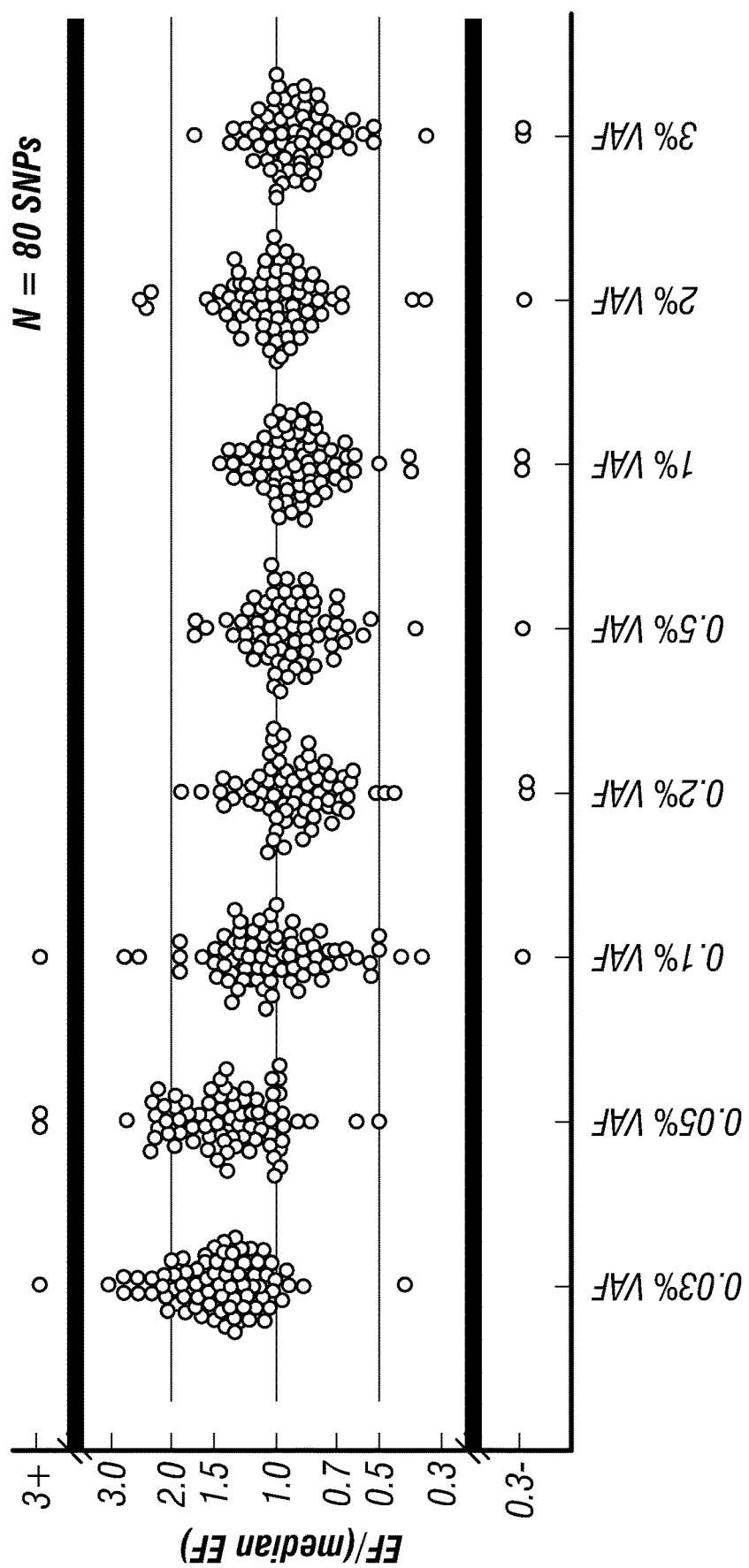
Figure 14E:
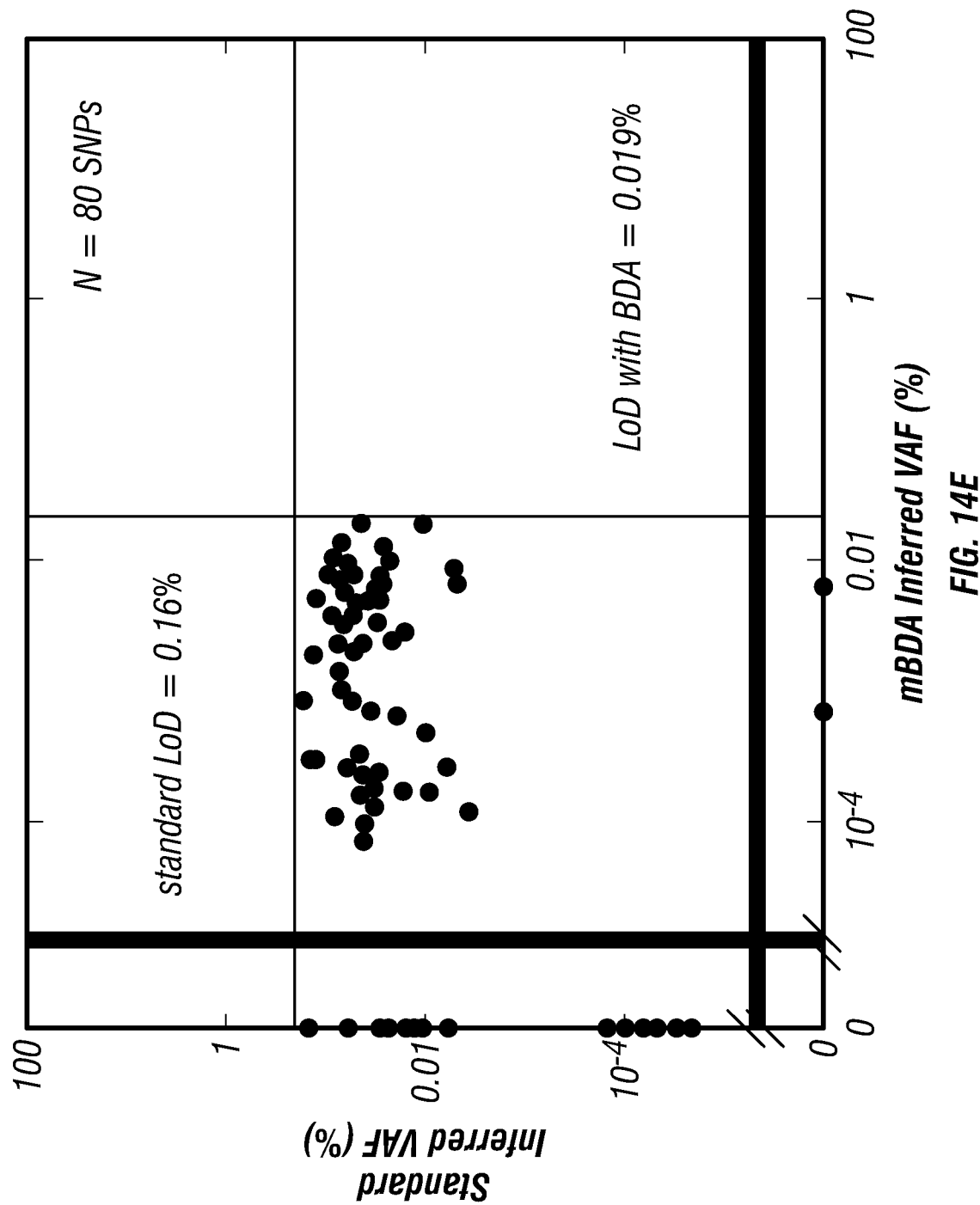

The theoretical relationship between VRF and VAF for different allele enrichment-fold (EF) is shown in FIG. 14A. EF values are expected to vary for different SNPs, but be conserved across different experiments and VAFs for the same SNP allele. The relationship between (1-VRF)/VRF and (1-VAF)/VAF is expected to be linear, with a slope of 1 and an intercept of log 10(EF) (FIG. 14B). This relationship allows simple and unbiased inferences of EF based on calibration mBDA NGS libraries using known VAF inputs. A summary of inferred EFs for each of the 80 variant SNP alleles using NA18537 as the primary alleles are shown in FIG. 14C. Dots show mean values and error bars show 1 standard deviation, based on 7 calibration mBDA NGS libraries using 0.03%, 0.05%, 0.1%, 0.2%, 0.5%, 1%, 2%, and 3% VAF samples. Relative EF values for different VAF inputs are shown in FIG. 14D. The EF/(median EF) ratio can also be interpreted as the quantitation error for the calibration samples with known VAFs; e.g. a ratio of 2 indicates under-estimation of VAF by a factor of 2. For the calibration samples, a large majority of SNPs across all 7 VAFs are quantitated accurately to within a factor of 2. Ideally, EF values should be identically distributed for all VAFs; however, a slight upwards bias was observed for EFs at very low VAFs below 0.1%. VAF limit of detection (LoD) for standard amplicon NGS vs. mBDA NGS is shown in FIG. 14E. Here, the LoD is defined as the maximum inferred VAF from a purely wildtype (0% VAF) sample; the red dots show the inferred VAFs for each of the 80 SNPs. For mBDA NGS, the VAF is calculated based on the median EF from the 7 EF values summarized in panels (FIG. 14C) and (FIG. 14D). For standard amplicon NGS, the VAF is calculated as simply the VRF. BDA improves the VAF LoD by more than 8-fold vs. standard amplicon NGS.

Example 5—Detection of Cell Line Contamination Using 80-Plex mBDA and qPCR Readout These experiments assume known base SNP genotype (of NA18537). The sequences and concentrations of primers and blockers used are shown in Table 1. The qPCR temperature cycle consisted of 2 minutes at 95° C. followed by 5 minutes at 60° C. The left panel of FIG. 10 shows triplicate qPCR traces of a pure NA18537 sample vs. a NA18537 sample with 5% NA18545 contaminant. The right panel of FIG. 10 shows a summary of Ct values observed for 24 replicate experiments of pure NA18537 and of NA18537 contaminated with 3% HeLa gDNA. Importantly, neither set of experiments utilized any genomic/genotypic information regarding NA18545 or HeLa.

Example 6—Detection of Minute Cell Line Contamination Using Multiplex Blocker Displacement Amplification (mBDA)

Figure 11A:
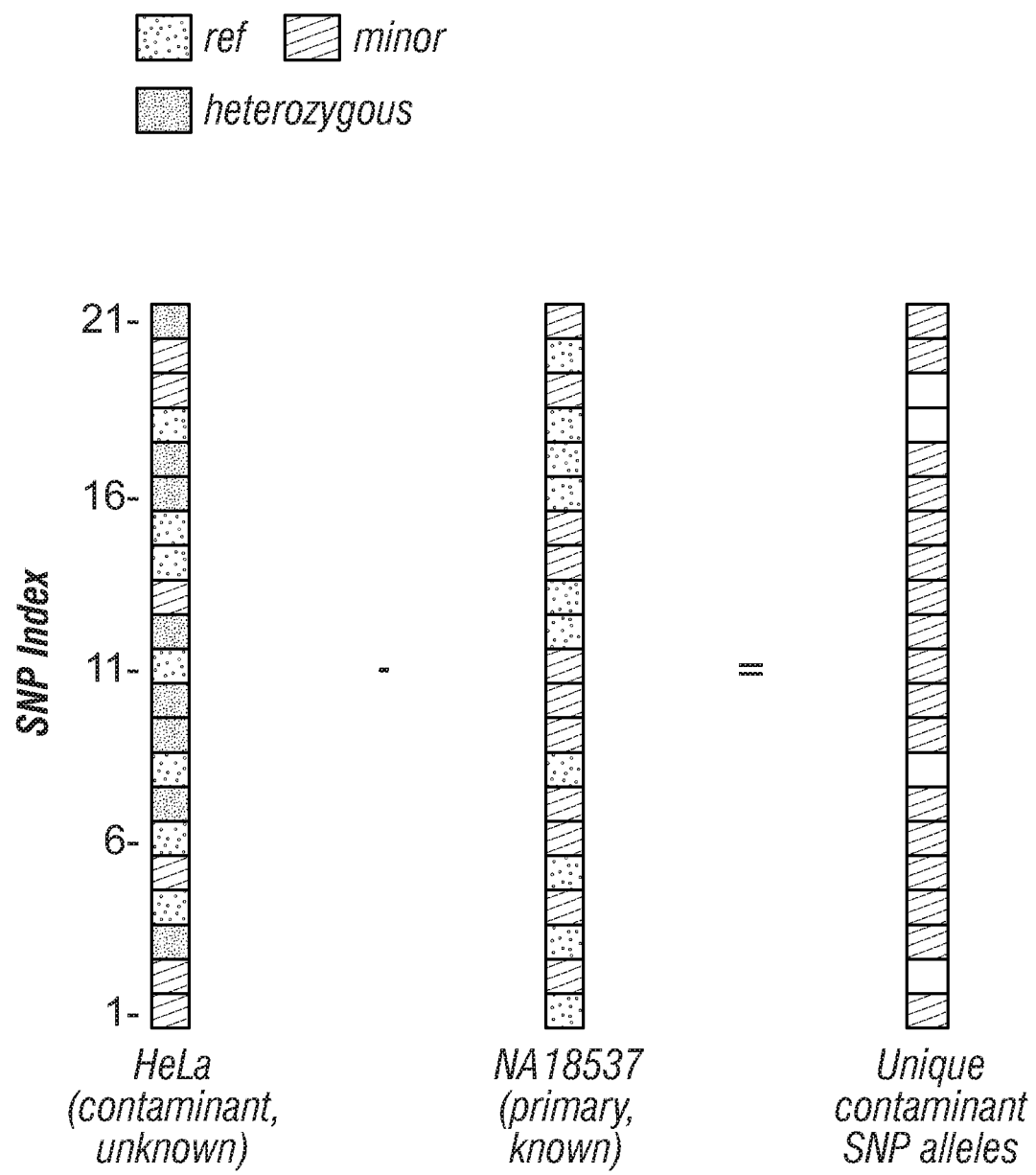
Figure 11B:
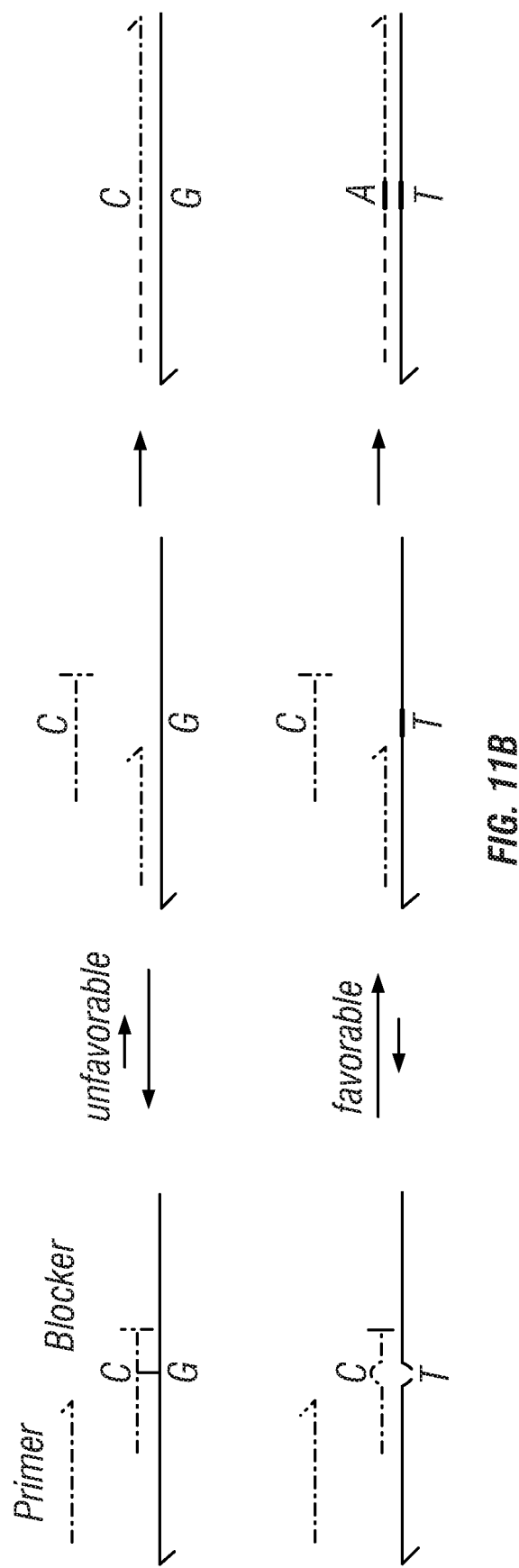
Figure 11C:
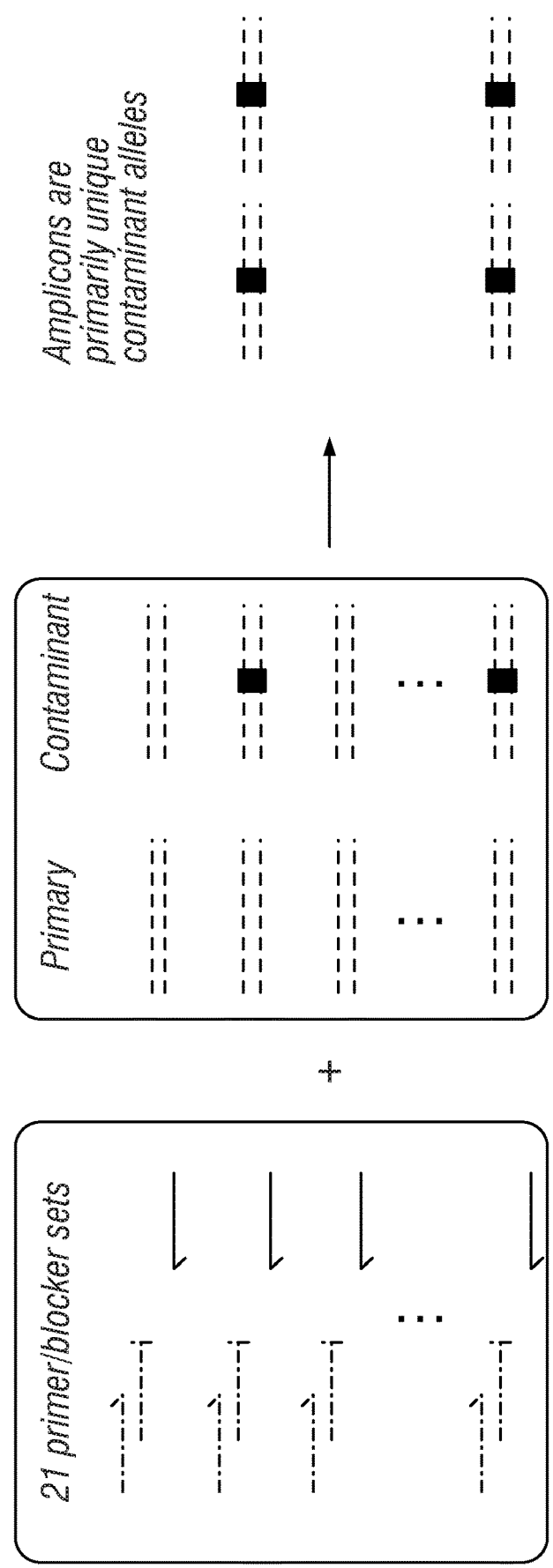
Figure 11E:
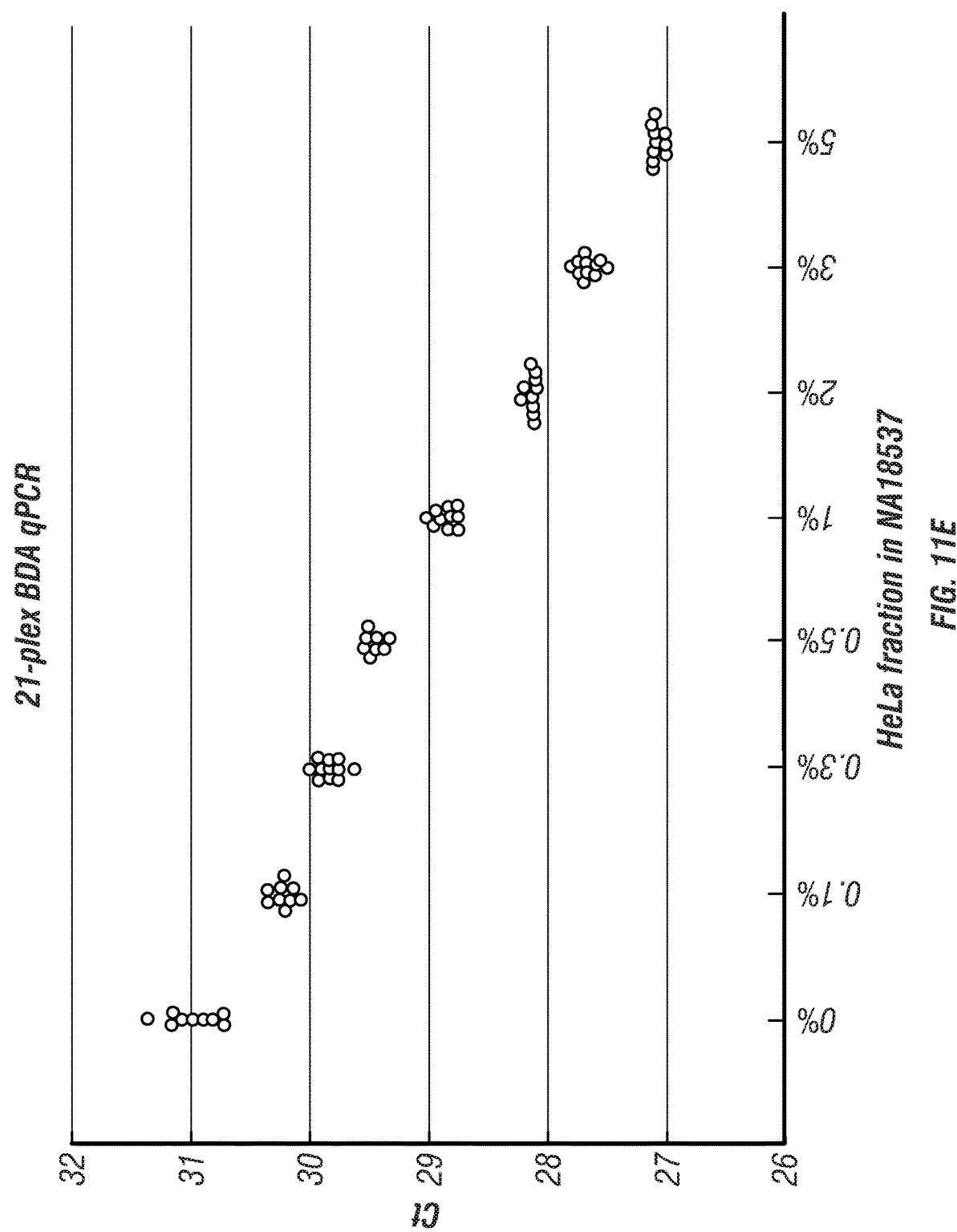

Given a known human cell line (here NA18537, referred to as the primary cell line), potential contamination by any other human cell line was sought to be detected. To this end, a list of SNPs in which the primary cell line is homozygous (either for the human reference allele, or the minor allele) was created. The unknown contaminant (here, HeLa) is overwhelming likely to differ in genotype in at least one SNP from the primary cell line, when the list of SNPs is sufficiently large. Detection of these unique contaminant SNP alleles allows detection and approximate quantitation of contamination without genotype information of the contaminant (FIG. 11A). BDA employs a rationally designed Blocker oligonucleotide that competes with the forward primer in binding to a DNA template. Here, the Blocker is designed to be perfectly complementary to the DNA template bearing the primary SNP allele, and mismatched to the variant SNP allele (FIG. 11B). This results in the variant SNP allele being preferentially amplified during PCR. A 21-plex mBDA set was designed against the primary alleles for all 21 SNP positions selected (FIG. 11C). Any contaminant present will have its unique contaminant SNP alleles be preferentially amplified, resulting in lower cycle threshold (Ct) values when using a double-stranded DNA intercalating dye such as SybrGreen I. mBDA maintains a large Ct difference between the primary and variant alleles in highly multiplexed reactions (FIG. 11D). Here, the variant DNA template tested is NA18562, which is homozygous variant in all selected SNPs. Different frequencies of HeLa contamination in NA18537 can be detected via mBDA using qPCR (FIG. 11E). The beeswarm plot shows the observed Ct values for 12 independent reactions for each sample. Even the 0.1% HeLa contaminant can be confidently distinguished from the pure NA18537 gDNA sample. Input quantity was 20 ng for all experiments summarized here.

Figure 12A:
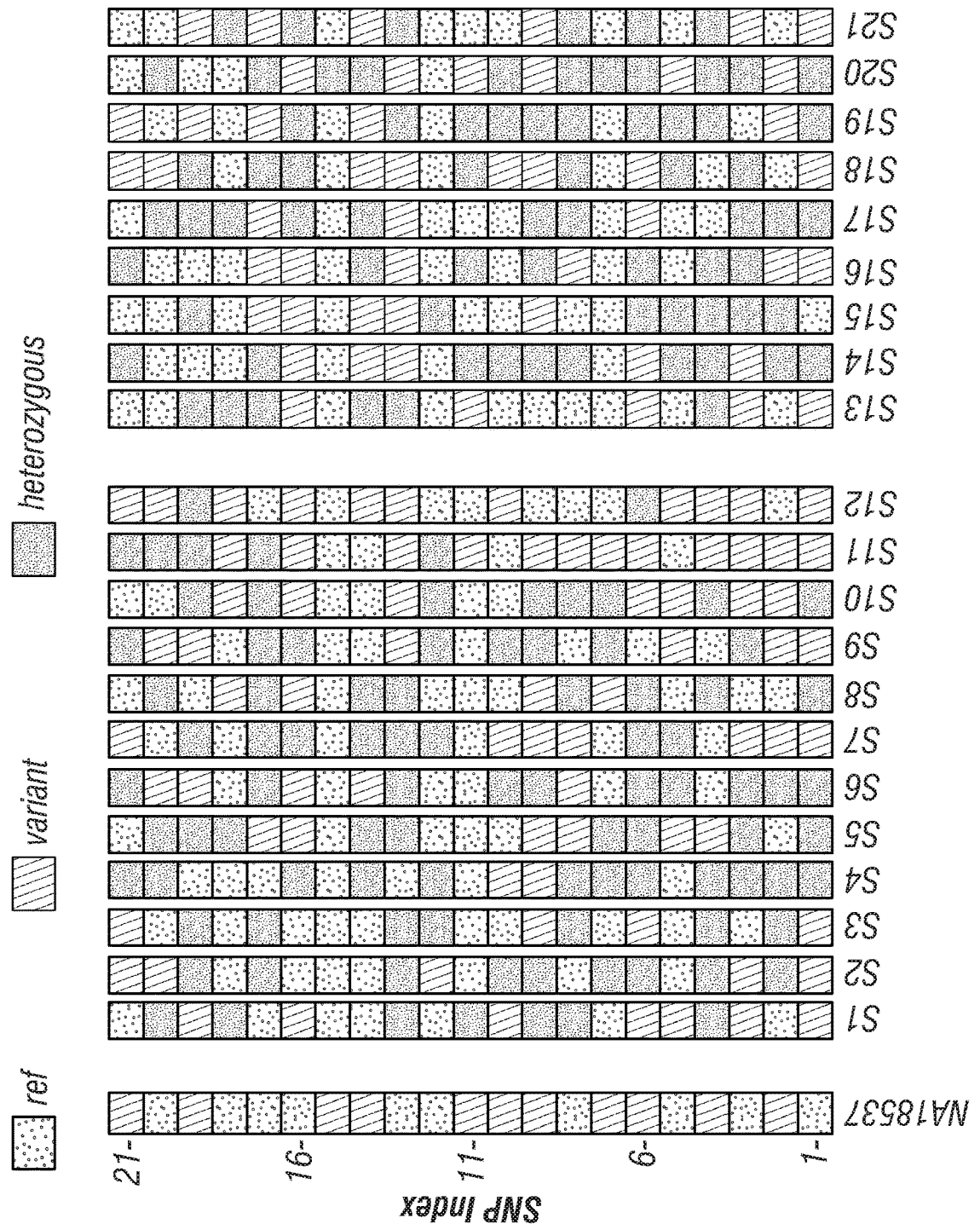
FIGS. 12A-D: Generalizability of the mBDA approach to detecting arbitrary human cell line contaminants.
Figure 12B:
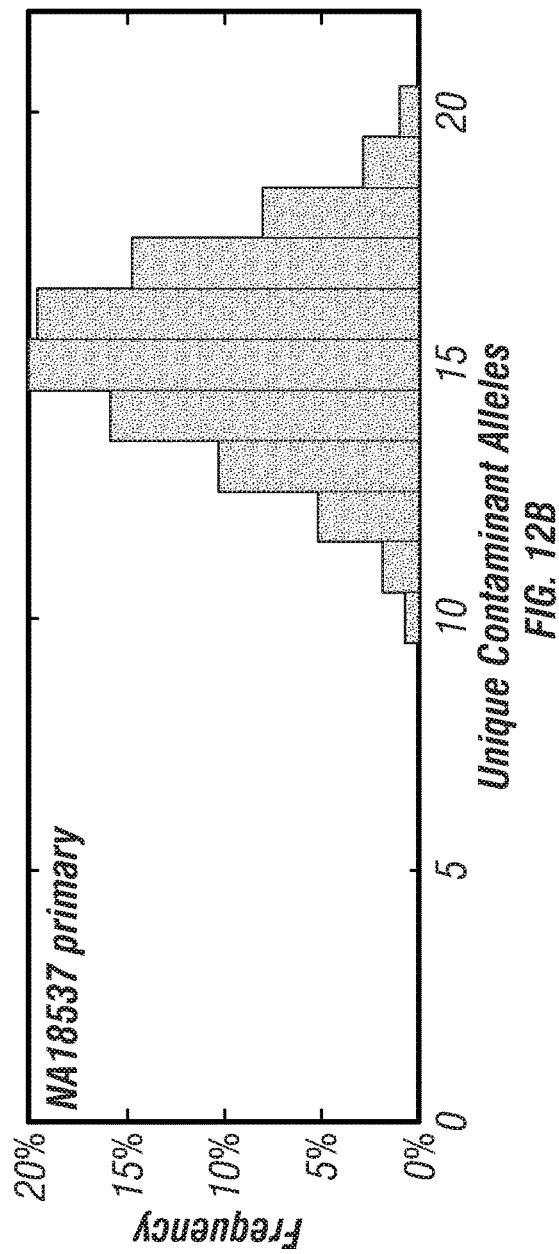
Figure 12C:
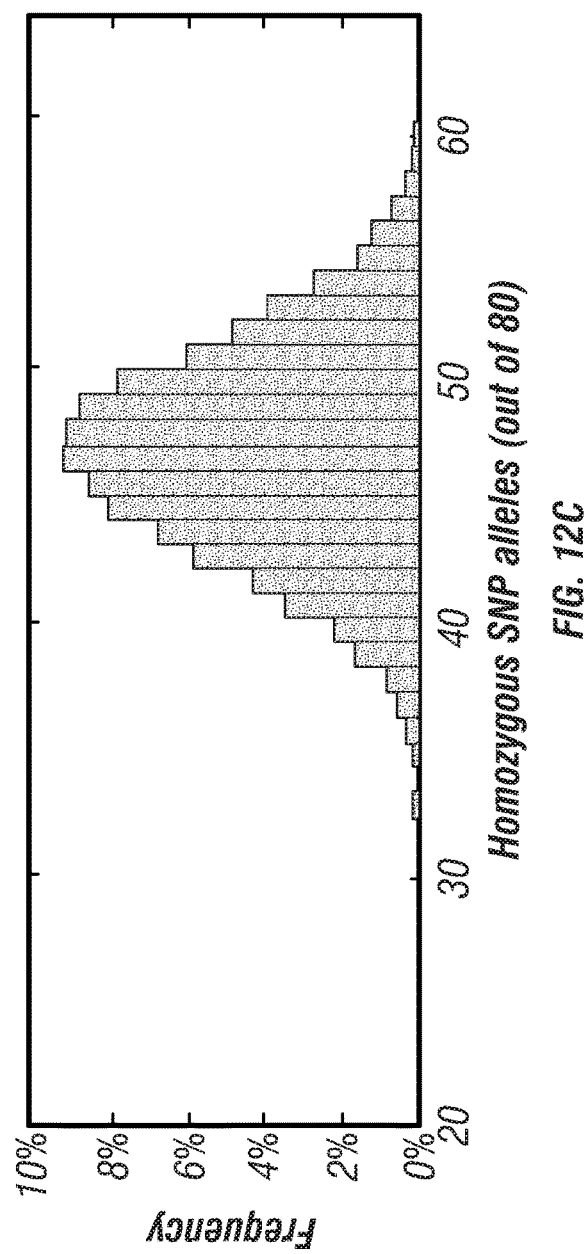
Figure 12D:
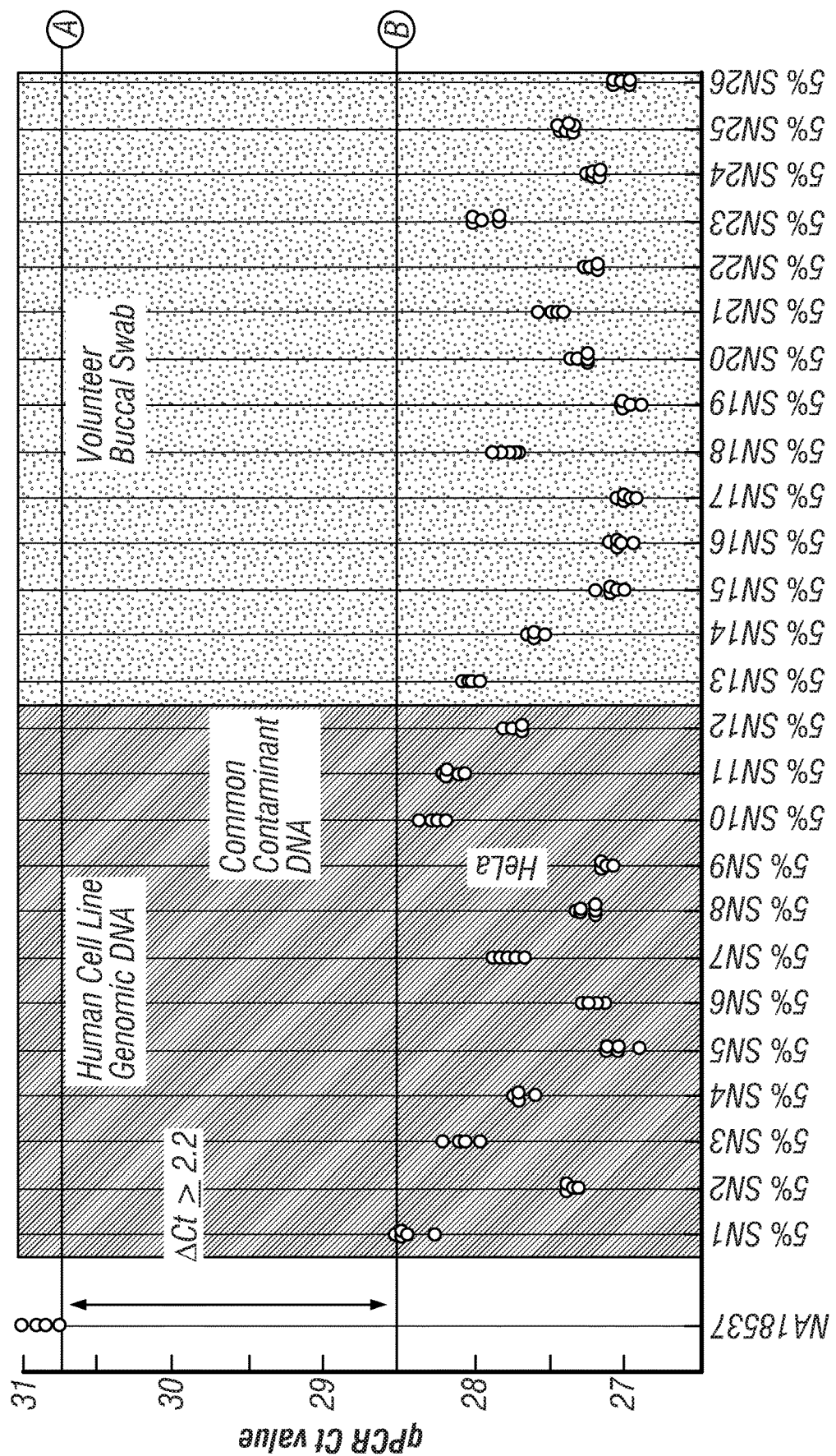
Figure 12D:
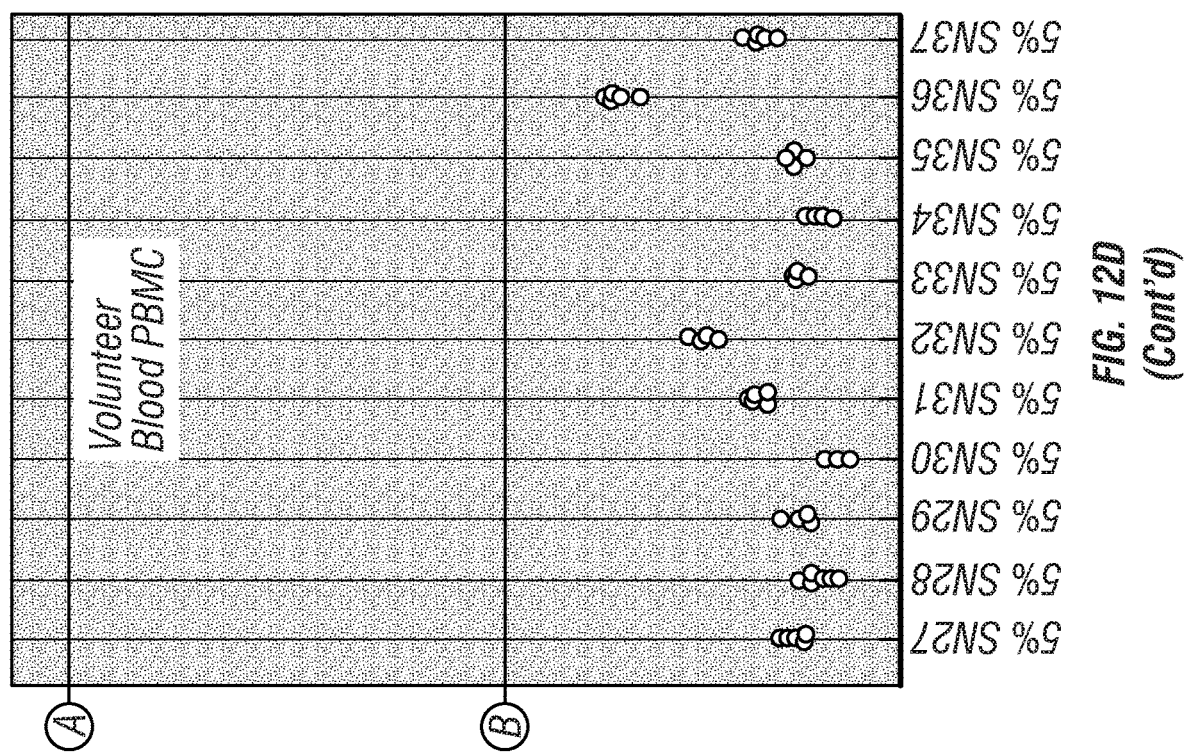

Example 7—Application of the mBDA Approach to Detecting Arbitrary Human Cell Line Contaminants SNP genotypes for 21 different contaminant samples were analyzed (FIG. 12A). S1 through S12 are cell lines purchased commercially, while S13 through S21 are deidentified DNA samples from volunteers. Note that S9 corresponds to HeLa. Simulated distribution of the number of unique contaminant alleles out of the 21 SNPs observed, against NA18537, was based on reported SNP population allele frequencies and assuming independence between SNPs (FIG. 12B). In all 100,000 simulation cases, there were at least 9 unique contaminant alleles, indicating that detecting of an arbitrary contaminant is overwhelmingly likely. An 80-plex mBDA set was designed and used to simulate the distribution of the number of homozygous SNPs for an arbitrary cell line, based on reported SNP population allele frequencies and assuming independence between SNPs (FIG. 12C). In all 100,000 simulation cases, there were at least 31 SNPs out of the 80 that were homozygous, indicating that selection of a 21-plex subset of the 80-plex mBDA set for developing a qPCR kit to detect contamination in new cell line is overwhelmingly likely. FIG. 12D provides a summary of qPCR results for detection of 5% contaminant in NA18537 with 37 different human DNA contaminants. Because the different contaminants have different numbers and groups of unique contaminant alleles, there is some difference in the Ct difference between contaminated and pure NA18537 ($\Delta$Ct). Six replicate qPCR reactions were performed for each sample, using 20 ng input DNA.

Example 8—Detection and Quantitation of DNA Contamination Using mBDA NGS

Figure 15A:
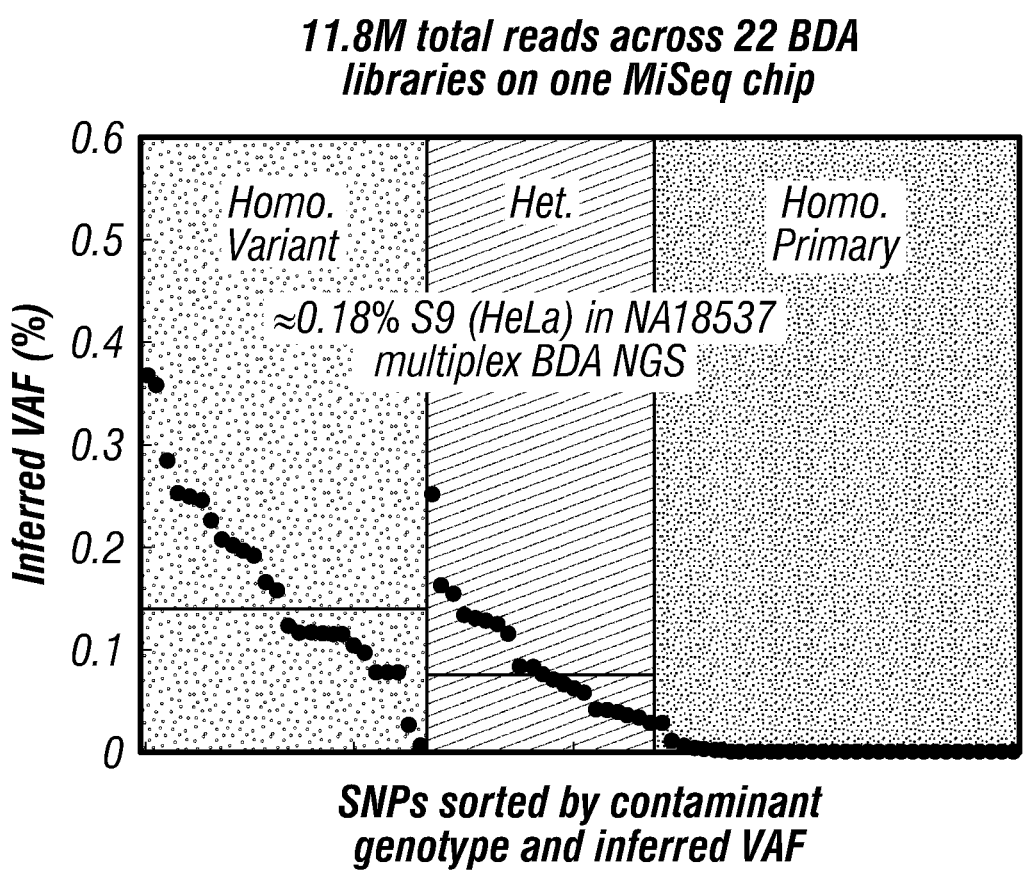
FIGS. 15A-D: Detection and quantitation of DNA contamination using mBDA NGS.
Figure 15B:
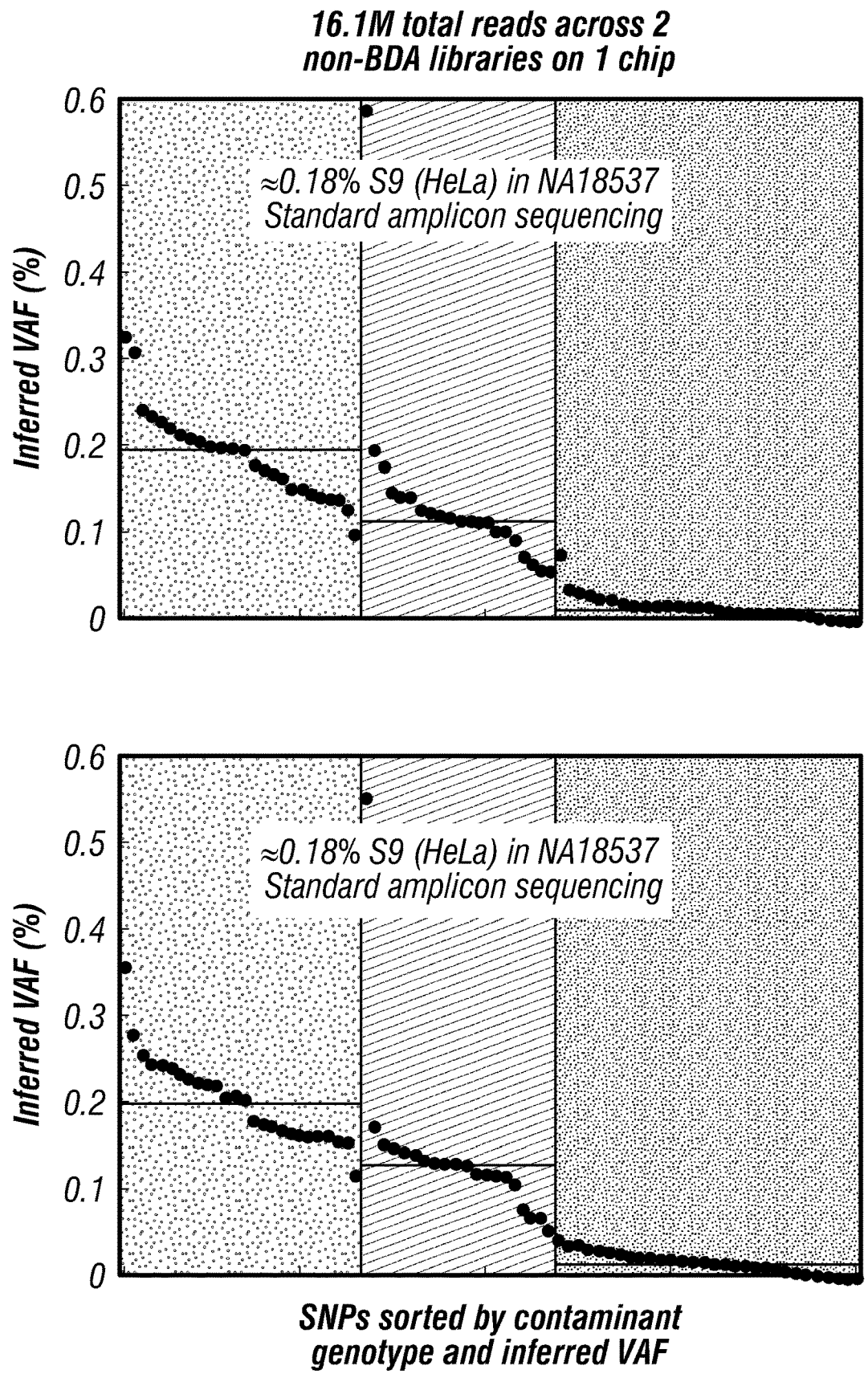
Figure 15C:
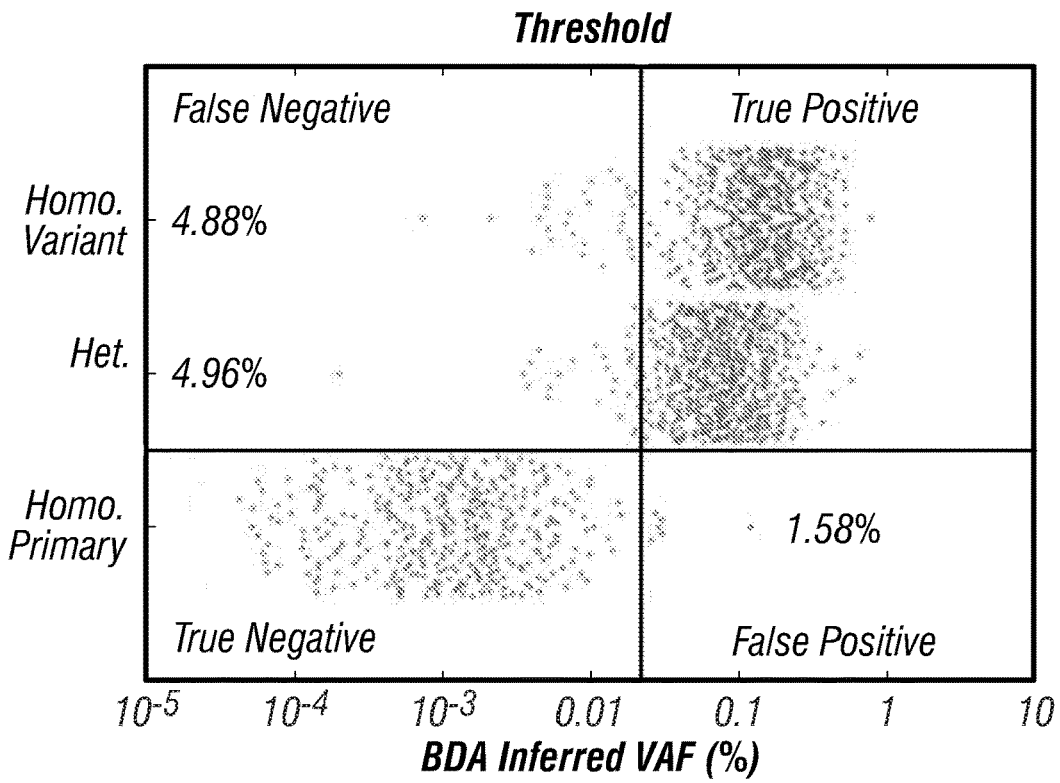
Figure 15D:
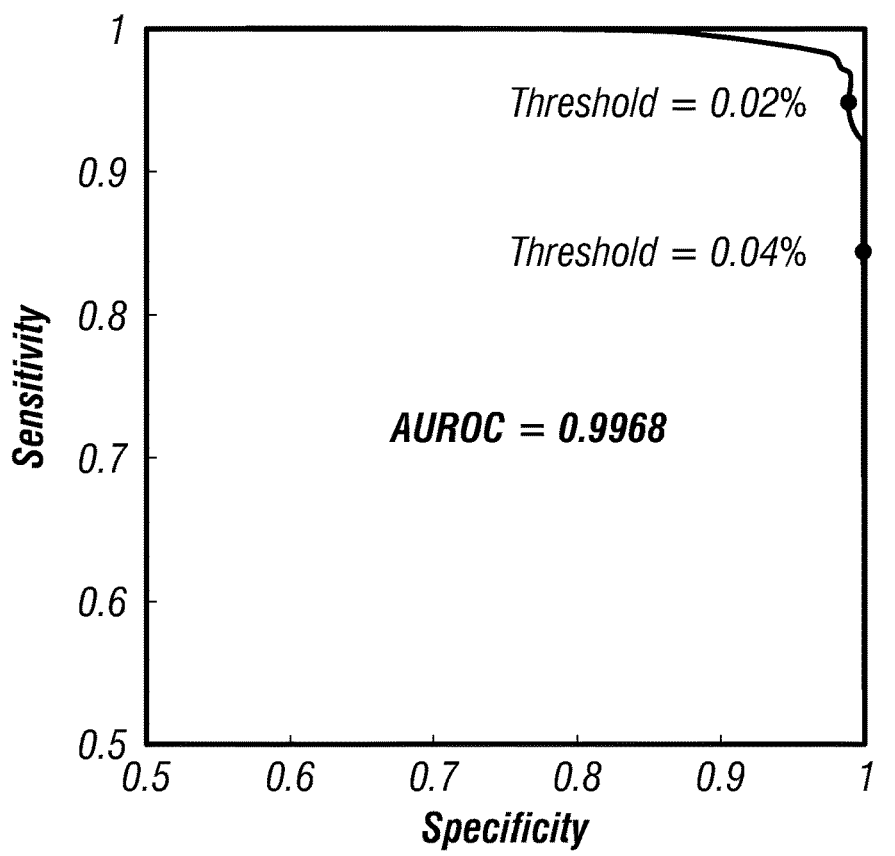

Results for 22 mBDA libraries on a single Mi Seq chip are provided in FIG. 15A. Each library corresponds to NA18537 contaminated with between roughly 0.1% and 0.2% of a different human DNA. Each subfigure shows the inferred VAF for all 80 SNPs, sorted by contaminant genotype and then by inferred VAF. The black horizontal lines show the median inferred VAF for homozygous variants and heterozygous variants. For all 22 libraries, the median inferred VAF for homozygous primary alleles were below 0.01%. Comparison libraries using standard amplicon NGS on the samples contaminated with S9 (HeLa) are shown in FIG. 15B. Note the significantly higher inferred VAF for homozygous primary alleles. A summary of variant call accuracy using the 0.019% VAF LoD threshold described in FIG. 14E is shown in FIG. 15C. All inferred VAFs from panel (FIG. 15A) are displayed in this beeswarm plot. There is a false positive variant call rate of 1.58%, and a false negative rate of 4.88% or 4.96%, depending whether the unique contaminant allele is homozygous or heterozygous, respectively. A receiver operator characteristic (ROC) plot for variant calls using the data in panel (FIG. 15C) is shown in FIG. 15D. Setting the variant call threshold at 0.04% VAF would increase specificity to 100%, at the cost of reducing sensitivity to roughly 85%. The area under the ROC curve is very high at 0.9968.

Example 9—Determination of Contaminant Identity Based on mBDA NGS Data

Figure 16A:
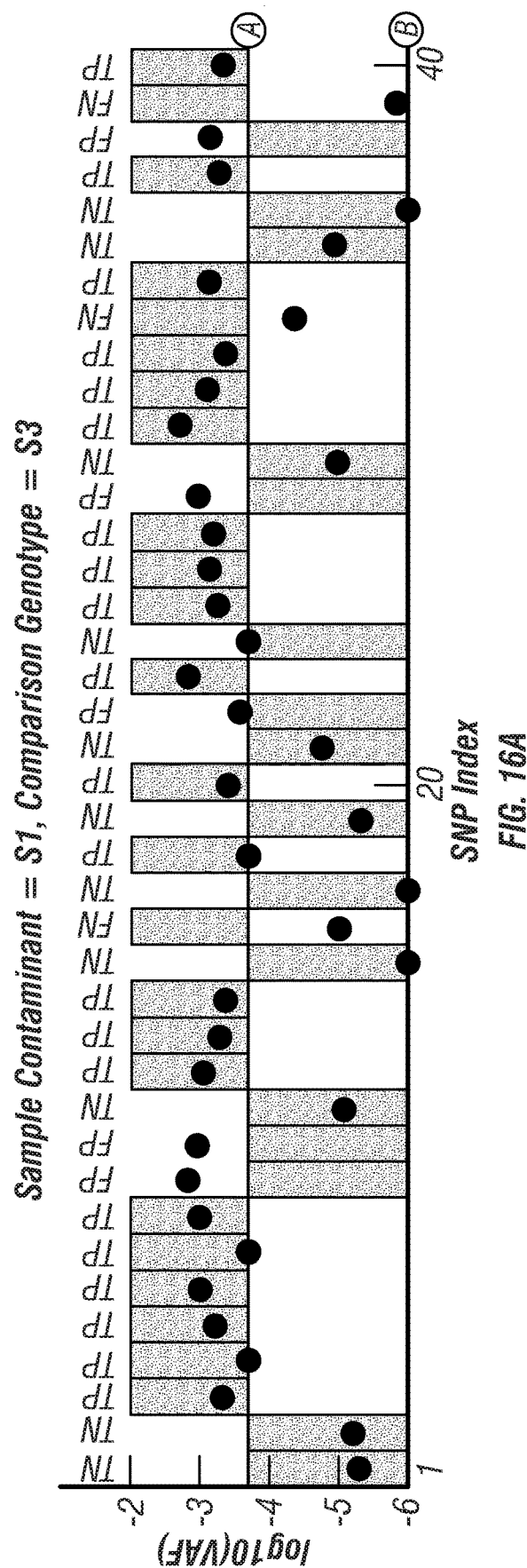
FIGS. 16A-D: Determination of contaminant identity based on mBDA NGS data.
Figure 16A:
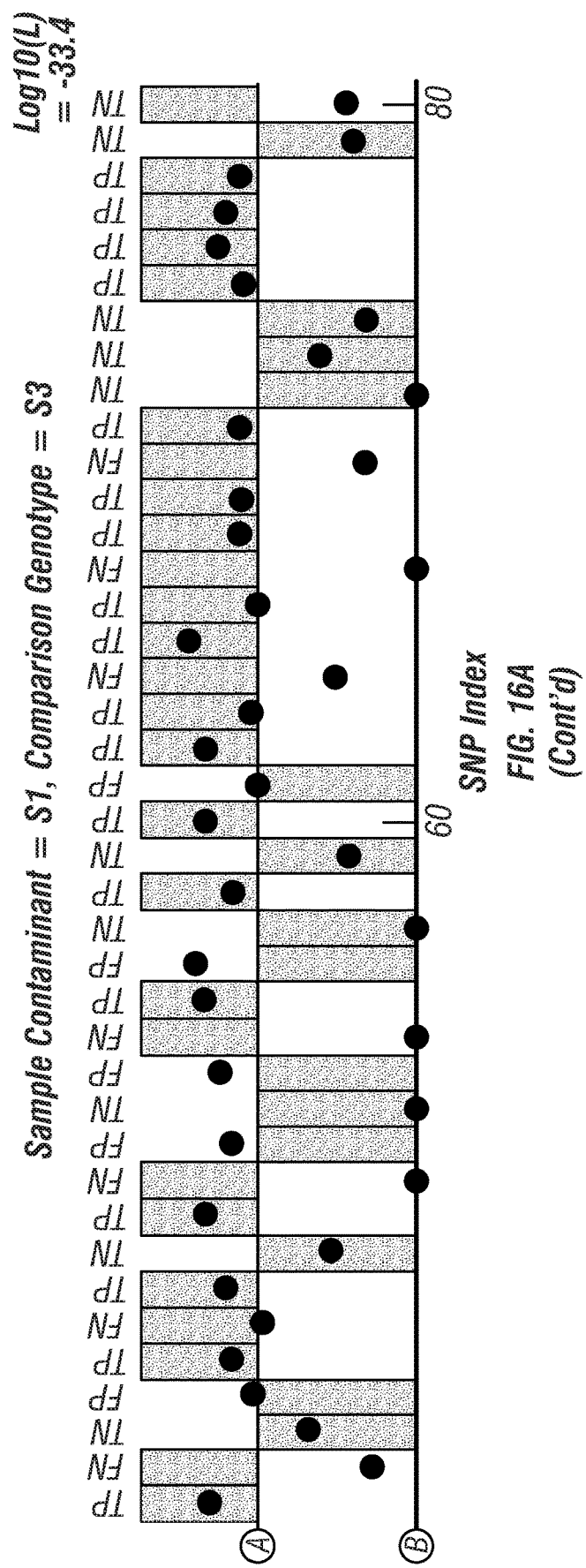
Figure 16A:
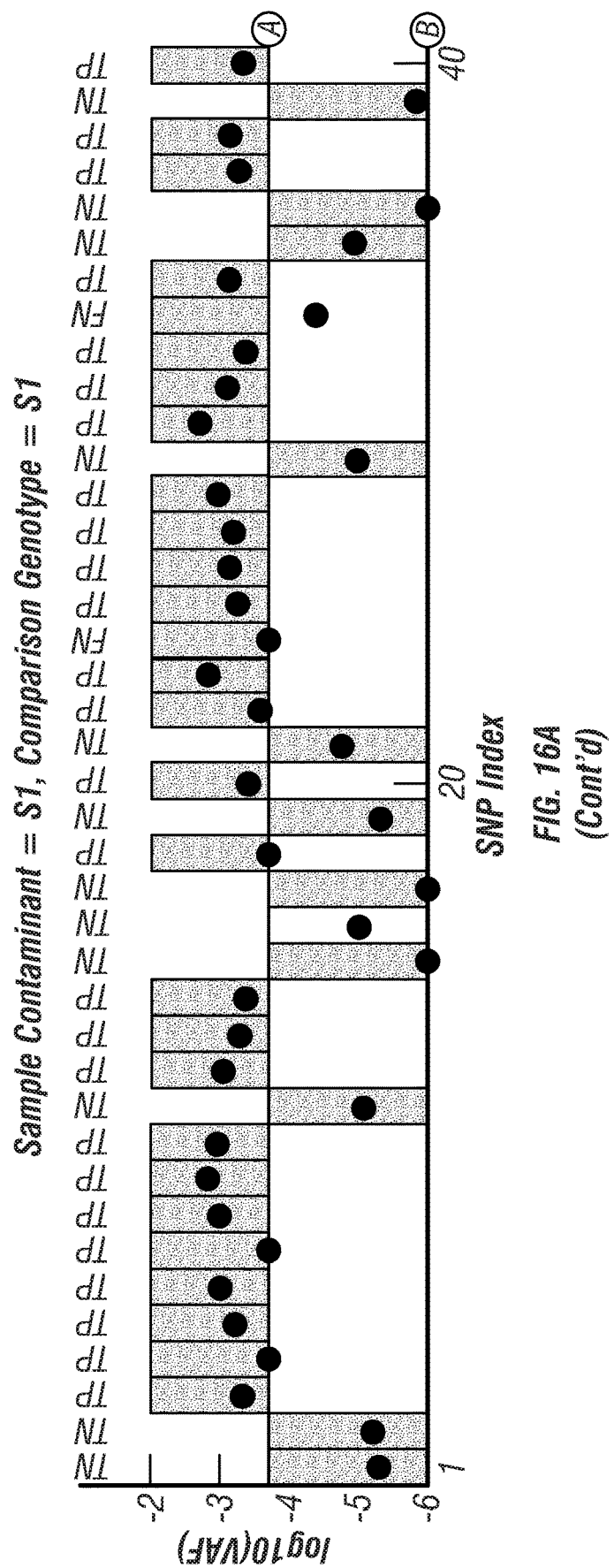
Figure 16A:
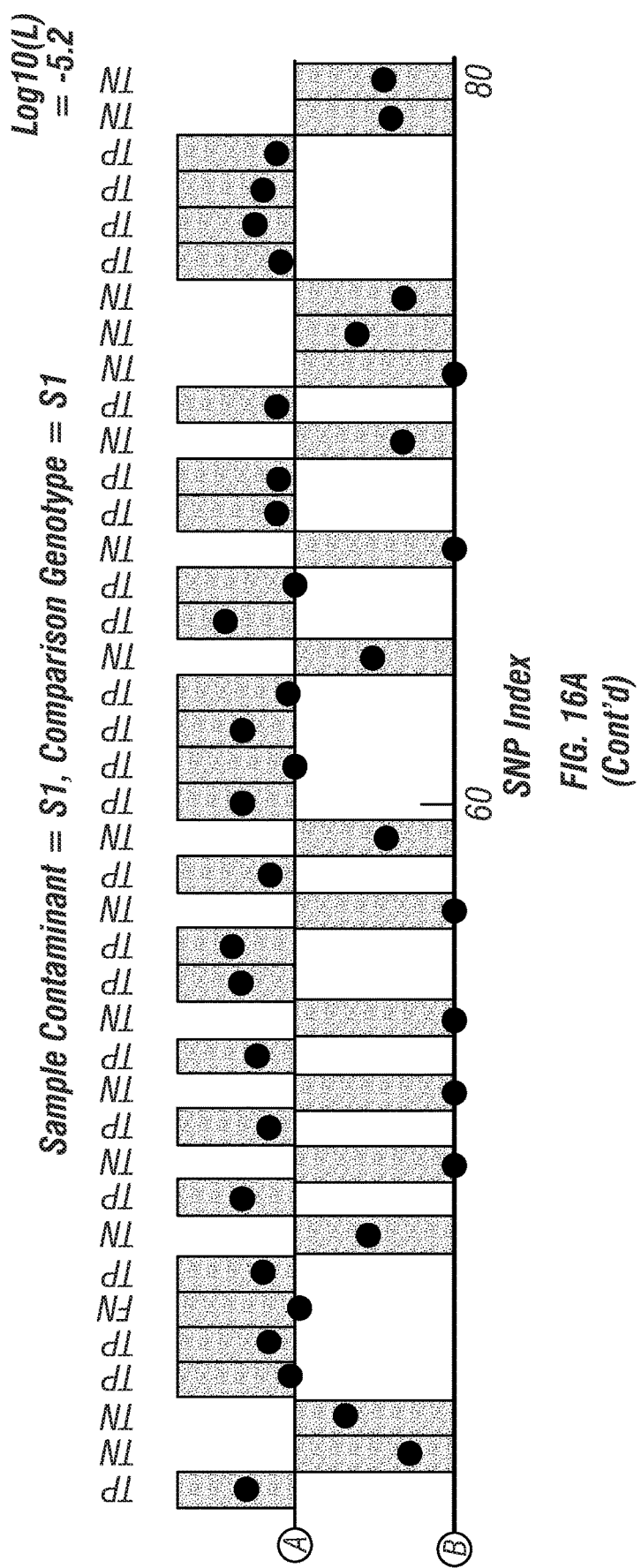
Figure 16B:
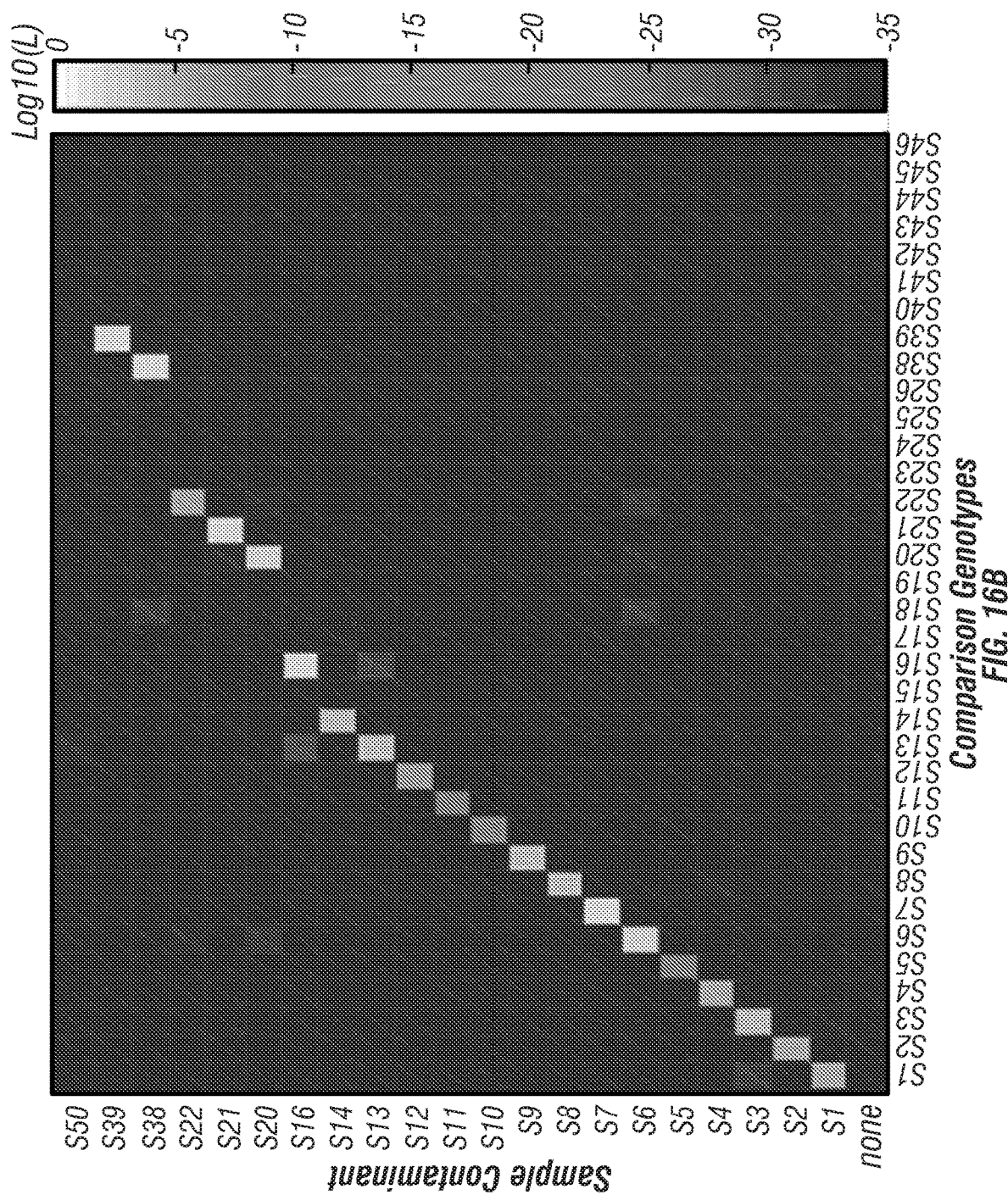
Figure 16D:
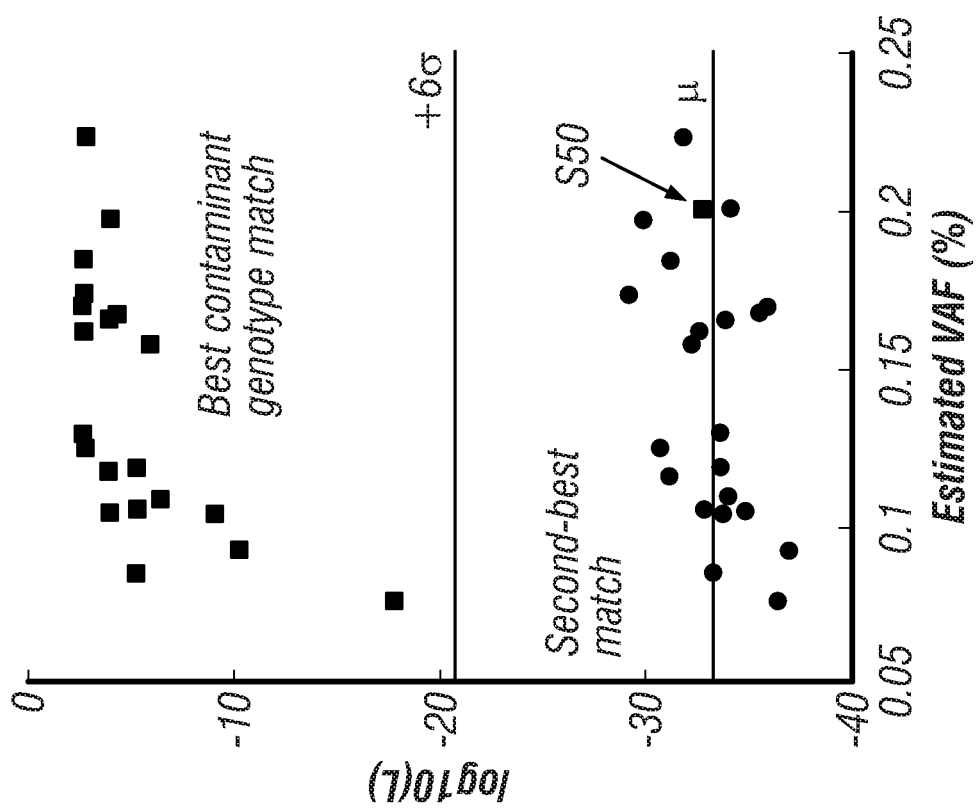
Figure 16C:
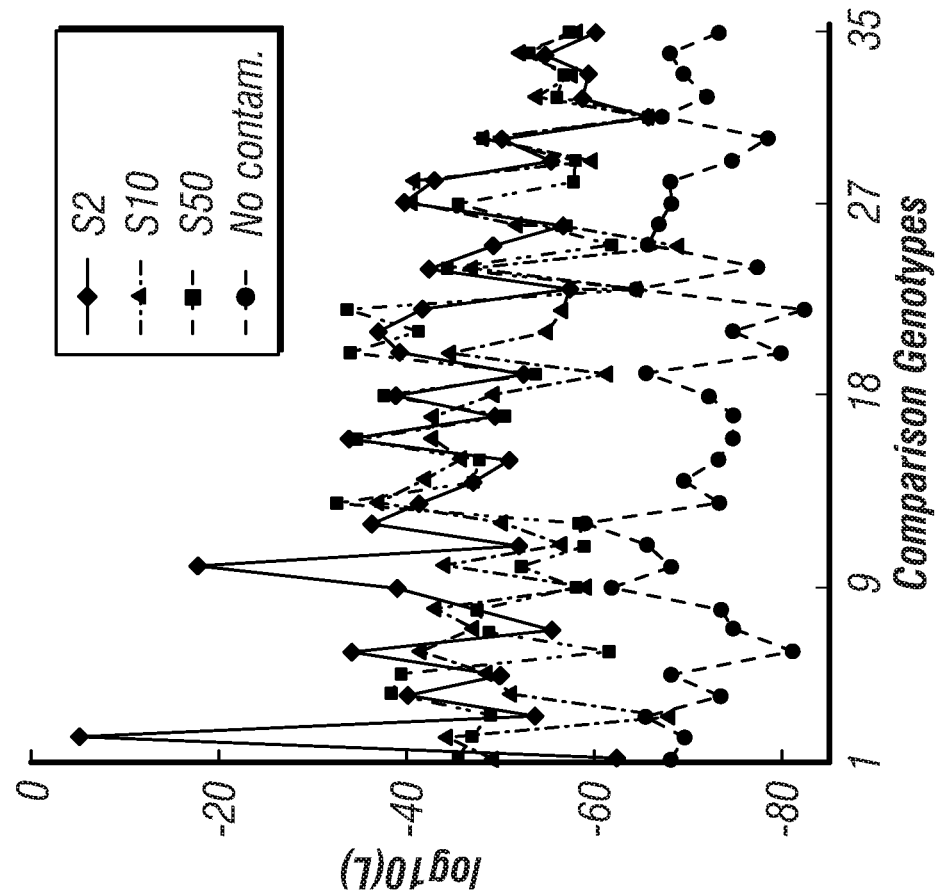

The calculation of contaminant likelihood based on mBDA variant calls is shown in FIG. 16A. For each SNP, a positive or negative variant allele call is made based on whether the inferred VAF (dots) is greater than the threshold of 0.019%. For each potential contaminant, whether a variant allele exists for each SNP (gray boxes) is considered, and thus whether the mBDA-inferred variant would be a True Positive (TP), True Negative (TN), False Positive (FP), or False Negative (FN) relative to the potential contaminant is determined. The overall likelihood L for the potential contaminant is calculated as the product of the likelihoods of all SNPs, with the likelihood of TP, TN, FP, and FN assigned as 95.08%, 98.42%, 1.58%, and 4.92%, respectively, based on FIG. 15C. The correct contaminant is expected to have a much higher value of L than incorrect contaminants. Heatmap plot of log 10(L) values for all pairwise combinations of all 22 tested samples (with contamination fraction between 0.07% and 0.22%) vs. 35 database genotypes is shown in FIG. 16B, based on data from FIG. 15A. Representative distributions of log 10(L) for 4 different samples are shown in FIG. 16C. S2 shows a typical sample whose contaminant genotype exists within the database. S10 shows the sample with the weakest maximum log 10(L) value whose genotype exists in the database. S50 shows a sample whose genotype is not included in the database of 35 genotypes. No contamination shows a sample of pure NA18537. A plot of highest and second-highest log 10(L) values against the contamination fraction is shown in FIG. 16D. The value of log 10(L) decreases for lower contamination fractions, consistent with expectations. However, even the S10 sample with 0.07% contamination is confidently identified, at over 6 standard deviations above the mean second-highest log 10(L) value. The S50 sample, which was not in the database, can also be confidently identified as an unknown contaminant based on its highest log 10(L) value.

Example 10—Patterns of SNPs Across 85 SNP Loci for 23 Individuals

The patterns of SNPs across 85 SNP loci were analyzed for 23 individuals (volunteers from the Houston area). In the left panel of FIG. 9, each column corresponds to one individual. The top right panel of FIG. 9 shows the number of valid SNP alleles for detecting contamination assuming known base genotype, given every possible pair of genotypes from the left panel (23*22). The bottom right panel of FIG. 9 shows the number of valid SNP alleles for detecting contamination assuming known contaminant genotype (randomly selecting blockers for heterozygous loci), given every possible pair of genotypes from the left panel. In both cases, there is a significant number of valid SNP loci for detecting possible contamination.

TABLE 1

Sequences and concentrations of forward primers (fP), blockers (B), and reverse primers (rP) used for the multiplex BDA experiments with results shown in FIGs. 4, 6, and 10. Note that the left panel of FIG. 4 did not use blockers.

| Name | Sequence | SEQ ID NO: | Conc. |
|---|---|---|---|
| rs10230708_fP | ACCAATGGGAGTCACTGCTG | 1 | 15 nM |
| rs10104396_fP | GAGGGGTATTAGAAGAATGACTATGTGA | 2 | 15 nM |
| rs199032_fP | GCTCTTCCTCTCACATCTTTATTTAACC | 3 | 15 nM |
| rs926850_fP | CAGAGTAAAATTTACTGCTCCGTCATAA | 4 | 15 nM |
| rs17149369_fP | GGATTCCCTAAGCTCTTCAATATTGC | 5 | 15 nM |
| rs869720_fP | CCTCATCTGTAAAGCAGGGAGAGA | 6 | 15 nM |
| rs12478327_fP | ACTTCTGCCAACATTCAAATTCAGG | 7 | 15 nM |
| rs2638145_fP | GGATGGGACTCCAATGCAAAACT | 8 | 15 nM |
| rs2170091_fP | CATCTTGCTCTTCATAGATAGCTTCAGA | 9 | 15 nM |
| rs2043583_fP | CCTGAATGTCAGTTTTGTTAGAGCAAC | 10 | 15 nM |
| rs955456_fP | CAGACTTAATCAAAGCCCTTGAAAAGA | 11 | 15 nM |
| rs966516_fP | CCTCCCATAGTGATTCTTATGAAGTCA | 12 | 15 nM |
| rs354169_fP | AATGCTTTGCTTGCTGAGAACTT | 13 | 15 nM |
| rs1898170_fP | AATGGGAAAACACATTTTAAGGGCA | 14 | 15 nM |
| rs11247921_fP | CCACACTCTGCCTCTCATGGTAT | 15 | 15 nM |
| rs1635718_fP | ACTTAAGAGGTCAACACAGATGAAAATTATC | 16 | 15 nM |
| rs10510620_fP | TCCGCAAAACCTACAATCTCTGAA | 17 | 15 nM |
| rs7104025_fP | TCAGATGCTTTAGGCTCATGAGTTA | 18 | 15 nM |
| rs2246745_fP | CTCCTTGGAATCACCAACAAACAT | 19 | 15 nM |
| rs3789806_fP | CTTGTATATAGACGGTAAAATAAACACCAAGA | 20 | 15 nM |
| rs706714_fP | TGAAGCAGATGTTGAACAACAAGG | 21 | 15 nM |
| rs1884444_fP | TTCCTGCTTCCAGACATGAATCA | 22 | 15 nM |
| rs2510152_fP | ACCCAGGTGAGTTTTGTTTCACAT | 23 | 15 nM |
| rs16754_fP | CTCTCTGCCTGCAGGATGTG | 24 | 15 nM |
| rs206781_fP | CACTTCCTCCAGAAGGTCCAAAG | 25 | 15 nM |
| rs28932178_fP | ACTAAGAGTGCAGAGCCTGGAA | 26 | 15 nM |
| rs10186821_fP | GCGTTGTGCTGTCCATTGG | 27 | 15 nM |
| rs10508599_fP | GGGTTAAAATCTTTTGCTTTCATATTGAGC | 28 | 15 nM |

TABLE 1-continued

Sequences and concentrations of forward primers (fP), blockers (B), and reverse primers (rP) used for the multiplex BDA experiments with results shown in FIGs. 4, 6, and 10. Note that the left panel of FIG. 4 did not use blockers.

| Name | Sequence | SEQ ID NO: | Conc. |
| --- | --- | --- | --- |
| rs10738578_fP | CCCGTTATATAAGAGGACATAATTGCAT | 29 | 15 nM |
| rs10741037_fP | CACTTTATCAGACACAGTTATGTGCT | 30 | 15 nM |
| rs10770674_fP | GCCCTATAGGTTTTCCTCCTACTGT | 31 | 15 nM |
| rs10805227_fP | CTATCTGCAGGATTGTGTTCAATGTA | 32 | 15 nM |
| rs10833604_fP | CTCTCTAGAGTGCAGATTGGTAGAA | 33 | 15 nM |
| rs10964389_fP | CAAAGTTGATAAATTAAAGGACTAAGGCAC | 34 | 15 nM |
| rs11015816_fP | CTGACCTAAGGCATGGGACTT | 35 | 15 nM |
| rs11045749_fP | CATTCTGTCTGGGATGAGGTGAT | 36 | 15 nM |
| rs1123828_fP | TGGAATCAAACATACTATGTGTCAAACA | 37 | 15 nM |
| rs11708584_fP | GCGAAGTCATTTCGGTCCTCTTTAA | 38 | 15 nM |
| rs12192635_fP | CCTCTGATTCCCAGACATAATGCT | 39 | 15 nM |
| rs12213948_fP | TGAAAGACGTCACAGCAAGGT | 40 | 15 nM |
| rs12259813_fP | TGTAGGAGAGATTGGGCTAGAGAG | 41 | 15 nM |
| rs12541300_fP | ACAGAAACCAATTACCTATGAGGAGTAA | 42 | 15 nM |
| rs12681931_fP | GAAAGTGGCACAGAAACTCAGAC | 43 | 15 nM |
| rs12782580_fP | GCATTAGATCATTTAACACACAAAACCCTAT | 44 | 15 nM |
| rs1375977_fP | TGCTCCTAAAAGCACCCAGC | 45 | 15 nM |
| rs1516755_fP | CTAACTTCCTAACTAAAACTTTACAGTGGA | 46 | 15 nM |
| rs1524303_fP | GGATTTCACACCCATTAGAATAACTACTAT | 47 | 15 nM |
| rs1667087_fP | CCTCTAGAAAAAATGGAGATTTGGGAAT | 48 | 15 nM |
| rs16871316_fP | GGACTTTTTTGCTTTTTGACACCTTTAC | 49 | 15 nM |
| rs16925478_fP | ACGTATTTCTAACTATAGTGAGTGCATTATG | 50 | 15 nM |
| rs17560702_fP | ACATGTCCAAAGAGAGAAGTCGTAG | 51 | 15 nM |
| rs1937037_fP | GCACGTAGATGAAATTGCCCCATA | 52 | 15 nM |
| rs2215492_fP | GCCCCAAAGGTTACCCCATG | 53 | 15 nM |
| rs2301720_fP | GTAGCCGCTTCTCTGTGAGTT | 54 | 15 nM |
| rs2616187_fP | GGAAAATATGTCTAAAAAGGCTCTGGAG | 55 | 15 nM |
| rs2710998_fP | GTTTGTTCTAAGGTTCATCTGGTGAT | 56 | 15 nM |
| rs2807238_fP | GTGGGCTTACATGATTGGATTAACTT | 57 | 15 nM |
| rs2874755_fP | TGTCCCACTTTTTACCTCCCTTC | 58 | 15 nM |
| rs3813787_fP | GGGCTTCGGAATCGGACTTG | 59 | 15 nM |
| rs4665582_fP | TGTGCTACGACAGAGCTAAGTAC | 60 | 15 nM |
| rs4712476_fP | CCCCGGATGTCAGGGAATG | 61 | 15 nM |
| rs611628_fP | CCAGGCACCACTGCTTTGT | 62 | 15 nM |
| rs6452035_fP | GCAGAAAAAAATGATATCTGAATTCTGGAT | 63 | 15 nM |
| rs6816854_fP | CCTTTTTCACTGTTATGAAATGTACTTTCTT | 64 | 15 nM |

TABLE 1-continued

Sequences and concentrations of forward primers (fP), blockers (B), and reverse primers (rP) used for the multiplex BDA experiments with results shown in FIGs. 4, 6, and 10. Note that the left panel of FIG. 4 did not use blockers.

| Name | Sequence | SEQ ID NO: | Conc. |
|---|---|---|---|
| rs6937778_fP | AGGATGCTGGGGCTTGC | 65 | 15 nM |
| rs7003044_fP | GTAAAGTGCATGGGGTCAAGTC | 66 | 15 nM |
| rs7032336_fP | TGAGAAGTCTAACAAGTTAAATTCAGGAC | 67 | 15 nM |
| rs7816009_fP | GGTAGAATGTTAGTGACTATGTACAATTTCA | 68 | 15 nM |
| rs7893462_fP | ACCTTGTCAAGAACCTAAATAGTGAGAA | 69 | 15 nM |
| rs7902135_fP | CGTGGGCTAGTCAAGAATATAAAATGTTAG | 70 | 15 nM |
| rs898476_fP | CCTATATAGACTAATTTACTTAAACATTTAAACCCCA | 71 | 15 nM |
| rs9368431_fP | GGTTCAACTCTCAGTTTTATTAGTTGTGT | 72 | 15 nM |
| rs9438621_fP | AGCATCGTGAGGTTCTGAAAAGA | 73 | 15 nM |
| rs9466035_fP | CCTAACACCAGTTCTTCCTCCAC | 74 | 15 nM |
| rs9466930_fP | TGTGTGGCTCAGTATACCACTTAG | 75 | 15 nM |
| rs9973865_fP | GAAAAAAAGGGTCTCATTAGGAATCATTAC | 76 | 15 nM |
| rs4712498_fP | GTTTTTATATGTTAGTGTCCCCATGGTATA | 77 | 15 nM |
| rs2073149_fP | AGTGATCAGAAGGCTTTGATTTGA | 78 | 15 nM |
| rs2862909_fP | GCACATCATACATTATTTCTGTTGCTAT | 79 | 15 nM |
| rs1338945_fP | GAAATATTGCTGGGGTCAGCG | 80 | 15 nM |
| rs10230708_B | ACTGCTGCAGGCGCCCTGT/iSpC3//iSpC3/TC | 81 | 150 nM |
| rs10104396_B | GACTATGTGACAAAATAGCTAAGGATACAGGAAATATG/iSpC3//iSpC3/GA | 82 | 150 nM |
| rs199032_B | CATCTTTATTTAACCCATTAGAAAATCCTATCAGCTCT/iSpC3//iSpC3/CG | 83 | 150 nM |
| rs926850_B | CCGTCATAACAAAAACATATTTACTTTCTCTGGC/iSpC3//iSpC3/CC | 84 | 150 nM |
| rs17149369_B | CTTCAATATTGCAGAAGTGTTGCAAGCCl/iSpC3//iSpC3/GT | 85 | 150 nM |
| rs869720_B | AGGGAGAGAACCTCCTCCCTCACAGA/iSpC3//iSpC3/TC | 86 | 150 nM |
| rs12478327_B | TCAAATTCAGGTACCTTAGAGGGACAGCTAAA/iSpC3//iSpC3/CT | 87 | 150 nM |
| rs2638145_B | AATGCAAAACTCAATGTATCAGTGTGAGGATGT/iSpC3//iSpC3/AT | 88 | 150 nM |
| rs2170091_B | TAGCTTCAGAAACATTCCAGTGTATGTGCAG/iSpC3//iSpC3/GA | 89 | 150 nM |
| rs2043583_B | GTTAGAGCAACTTTCCTTGATTCCCAGAGTAG/iSpC3//iSpC3/CT | 90 | 150 nM |
| rs955456_B | CCTTGAAAAGAGGGCTTAGGTTTTCTTTGC/iSpC3//iSpC3/TA | 91 | 150 nM |
| rs966516_B | CTTATGAAGTCATGGAACAATGCCTACTTCTATATTT/iSpC3//iSpC3/AG | 92 | 150 nM |
| rs354169_B | CTGAGAACTTAGCATTAATTACCTTTTTTCATGAGAAT/iSpC3//iSpC3/TA | 93 | 150 nM |

TABLE 1-continued

Sequences and concentrations of forward primers (fP), blockers (B), and reverse primers (rP) used for the multiplex BDA experiments with results shown in FIGs. 4, 6, and 10. Note that the left panel of FIG. 4 did not use blockers.

| Name | Sequence | SEQ ID NO: | Conc. |
|---|---|---|---|
| rs1898170_B | AGGGCATTTTTTACAGTGTTGAATATTGAAACTG/iSpC3//iSpC3/TG | 94 | 150 nM |
| rs11247921_B | CTCTCATGGTATGGTGTTTTTCTGTGCTCC/iSpC3//iSpC3/CG | 95 | 150 nM |
| rs1635718_B | CAGATGAAAATTATCTGTGCTTTTTTGTAAGCTGATATATT/iSpC3//iSpC3/TC | 96 | 150 nM |
| rs10510620_B | CAATCTCTGAATCTCAGAATAGTAGCCTAGAAAACG/iSpC3//iSpC3/GC | 97 | 150 nM |
| rs7104025_B | CTCATGAGTTAACAAGGAGATGATGTAGTGTAAAG/iSpC3//iSpC3/GC | 98 | 150 nM |
| rs2246745_B | CAACAAACATGCCTTCTCCTTCTCCTGA/iSpC3//iSpC3/AA | 99 | 150 nM |
| rs3789806_B | TAAACACCAAGACGTGGTAAATATTTACCTGGT/iSpC3//iSpC3/CG | 100 | 150 nM |
| rs706714_B | CAACAAGGTCAGTATTGATAAGTGGTTGCT/iSpC3//iSpC3/AG | 101 | 150 nM |
| rs1884444_B | ACATGAATCATGTCACTATTCAATGGGATGC/iSpC3//iSpC3/TT | 102 | 150 nM |
| rs2510152_B | TTTTGTTTCACATGATAACCATATCACTGGACACA/iSpC3//iSpC3/CC | 103 | 150 nM |
| rs16754_B | AGGATGTGCGACGTGTGCCTG/iSpC3//iSpC3/GG | 104 | 150 nM |
| rs206781_B | GGTCCAAAGCCGGAAGGGCCTAAA/iSpC3//iSpC3 /AA | 105 | 150 nM |
| rs28932178_B | GCCTGGAACCGAGACGCCTCAG/iSpC3//iSpC3/TG | 106 | 150 nM |
| rs10186821_B | TCCATTGGCTACTCAGTCTCGGCT/iSpC3//iSpC3/AT | 107 | 150 nM |
| rs10508599_B | TCATATTGAGCTTAAGAGTTCAGAACACTGATGG/iSpC3//iSpC3/AT | 108 | 150 nM |
| rs10738578_B | CATAATTGCATATAACCTACACACATTCTCCCA/iSpC3//iSpC3/TT | 109 | 150 nM |
| rs10741037_B | GTTATGTGCTGGAAAGAGCATAAATTTTGGAAT/iSpC3//iSpC3/AA | 110 | 150 nM |
| rs10770674_B | CTCCTACTGTACATACATATTATCTTAAGGAAAAAATCCAAAT/iSpC3//iSpC3/AT | 111 | 150 nM |
| rs10805227_B | TGTTCAATGTATTAAATAATCATCAGCATATTTTTGTATTCAC/iSpC3//iSpC3/AA | 112 | 150 nM |
| rs10833604_B | GATTGGTAGAAGACACTGATTGCATCTTCAA/iSpC3//iSpC3/GT | 113 | 150 nM |
| rs10964389_B | AAGGCACAGAACAATCATGCAACTTGC/iSpC3//iSpC3/AT | 114 | 150 nM |
| rs11015816_B | GGGACTTTCTTGAGGGATGGCATCC/iSpC3//iSpC3/CT | 115 | 150 nM |
| rs11045749_B | GAGGTGATATCTCATTTTGGCTTCTATTTGCA/iSpC3//iSpC3/TA | 116 | 150 nM |

TABLE 1-continued

Sequences and concentrations of forward primers (fP), blockers (B), and reverse primers (rP) used for the multiplex BDA experiments with results shown in FIGs. 4, 6, and 10. Note that the left panel of FIG. 4 did not use blockers.

| Name | Sequence | SEQ ID NO: | Conc. |
| --- | --- | --- | --- |
| rs1123828_B | TGTCAAACACCCATGCTCACCCTT/iSpC3//iSpC3/CA | 117 | 150 nM |
| rs11708584_B | GGTCCTCTTTAAGGTCTCTACAATAAATTGCCA/iSpC3//iSpC3/AA | 118 | 150 nM |
| rs12192635_B | GACATAATGCTTTTGGTTGGACTTTCAAAAGG/iSpC3//iSpC3/GT | 119 | 150 nM |
| rs12213948_B | GCAAGGTTCAAATCATTCTCTCCTATCTCATC/iSpC3//iSpC3/TT | 120 | 150 nM |
| rs12259813_B | GCTAGAGAGATAATTGAGTGTCATCAGAACTAGAT/iSpC3//iSpC3/TT | 121 | 150 nM |
| rs12541300_B | ATGAGGAGTAATTGAAATCATTAATACCCACAAACA/iSpC3//iSpC3/TT | 122 | 150 nM |
| rs12681931_B | AACTCAGACCAATTTGGCCATAGATTATTAGC/iSpC3//iSpC3/TT | 123 | 150 nM |
| rs12782580_B | ACAAAACCCTATAAGGAAGATGTCATTACCCATATTTTA/iSpC3//iSpC3/TT | 124 | 150 nM |
| rs1375977_B | ACCCAGCTTTATACATTCACAAAGATATGGTTTG/iSpC3//iSpC3/AA | 125 | 150 nM |
| rs1516755_B | ACAGTGGAACAGCTCTCTCCTTCTTTTTT/iSpC3//iSpC3/CA | 126 | 150 nM |
| rs1524303_B | ATTAGAATAACTACTATTAAAAAAACCCCACAAAATAACTCTT/iSpC3//iSpC3/CT | 127 | 150 nM |
| rs1667087_B | TTTGGGAATTAAAAGCCAATAGATTAGCTGAAAATTC/iSpC3//iSpC3/AT | 128 | 150 nM |
| rs16871316_B | ACACCTTTACATGAAGGCTTTGAAGTACTCTT/iSpC3//iSpC3/AT | 129 | 150 nM |
| rs16925478_B | GTGCATTATGGGTAAGAATGTTCATTTATTATTTCACTTATA/iSpC3//iSpC3/GA | 130 | 150 nM |
| rs17560702_B | GAAGTCGTAGCTATTCGGCAAAGGAAATG/iSpC3//iSpC3/TT | 131 | 150 nM |
| rs1937037_B | TGCCCCATAGGCAGTGTTTGGTGAAG/iSpC3//iSpC3/GT | 132 | 150 nM |
| rs2215492_B | TACCCCATGTGTATCAAATGGTCAGCAAG/iSpC3//iSpC3/TT | 133 | 150 nM |
| rs2301720_B | CTGTGAGTTGGGAGCAAAGGAGCA/iSpC3//iSpC3/AT | 134 | 150 nM |
| rs2616187_B | CTCTGGAGACGGGGGATGTTAAGTTGA/iSpC3//iSpC3/AA | 135 | 150 nM |
| rs2710998_B | TCTGGTGATTGAGAAAGCGTTCCAGA/iSpC3//iSpC3/GA | 136 | 150 nM |
| rs2807238_B | ATTGGATTAACTTTGGTGGAACCTACTTCGAT/iSpC3//iSpC3/AT | 137 | 150 nM |
| rs2874755_B | CTCCCTTCTTTCATCCCTACATCATGTCC/iSpC3//iSpC3/AA | 138 | 150 nM |
| rs3813787_B | CGGACTTGGCTGGGGTAGAGCTT/iSpC3//iSpC3/AA | 139 | 150 nM |

TABLE 1-continued

Sequences and concentrations of forward primers (fP),
blockers (B), and reverse primers (rP) used for the multiplex
BDA experiments with results shown in FIGs. 4, 6, and 10.
Note that the left panel of FIG. 4 did not use blockers.

| Name | Sequence | SEQ ID NO: | Conc. |
| --- | --- | --- | --- |
| rs4665582_B | GAGCTAAGTACCAGGTATGATGCTCGC/iSpC3//iSpC3/AT | 140 | 150 nM |
| rs4712476_B | AGGGAATGCTCTAGACAAAACACTGTTCC/iSpC3//iSpC3/TA | 141 | 150 nM |
| rs611628_B | TGCTTTGTGCTAGCTCAAAGACTCACAT/iSpC3//iSpC3/TT | 142 | 150 nM |
| rs6452035_B | AATTCTGGATCAAATTAAATATGTCGCATTCTCC/iSpC3//iSpC3/GT | 143 | 150 nM |
| rs6816854_B | TGTACTTTCTTTTTAGCCATAAGATGATTTCCCAT/iSpC3//iSpC3/AT | 144 | 150 nM |
| rs6937778_B | GCTTGCTTTCCCACACCACTACCT/iSpC3//iSpC3/TA | 145 | 150 nM |
| rs7003044_B | GGTCAAGTCTGAGGCTGTTGAGCTTA/iSpC3//iSpC3/GA | 146 | 150 nM |
| rs7032336_B | TTCAGGACGTGAAAGCACGAGAACG/iSpC3//iSpC3/AT | 147 | 150 nM |
| rs7816009_B | ATGTACAATTTCAACTGGAGTTTCCATTGCA/iSpC3//iSpC3/GT | 148 | 150 nM |
| rs7893462_B | AAATAGTGAGAACGAGCAGCTGCAGG/iSpC3//iSpC3/CT | 149 | 150 nM |
| rs7902135_B | AAGAATATAAAATGTTAGAGAACCACATACAACGAGC/iSpC3//iSpC3/CT | 150 | 150 nM |
| rs898476_B | AACCCCAGAACACTAGCAGCTAAGGG/iSpC3//iSpC3/TA | 151 | 150 nM |
| rs9368431_B | TTTTATTAGTTGTGTAATCCAGTTACTTAACTTTAAAAGCC/iSpC3//iSpC3/AT | 152 | 150 nM |
| rs9438621_B | GTTCTGAAAAGAGCCTCCACTCCTGT/iSpC3//iSpC3/TT | 153 | 150 nM |
| rs9466035_B | CCTCCACTCCACCATGGCACCTATTA/iSpC3//iSpC3/AA | 154 | 150 nM |
| rs9466930_B | GTATACCACTTAGGCTATAGTTATTCTAAACTTTGATAAAC/iSpC3//iSpC3/GT | 155 | 150 nM |
| rs9973865_B | AGGAATCATTACAGGAAAACATCGTTTAAATTGGA/iSpC3//iSpC3/AA | 156 | 150 nM |
| rs4712498_B | CCATGGTATATTGTAAGTTGTAGGTACATACCC/iSpC3//iSpC3/AA | 157 | 150 nM |
| rs2073149_B | TTTGATTTGAATAAACCAGAGAACTCTTCTGAG/iSpC3//iSpC3/TT | 158 | 150 nM |
| rs2862909_B | TGTTGCTATCTTGCTTTTAGCATTTAGTGC/iSpC3//iSpC3/AA | 159 | 150 nM |
| rs1338945_B | TCAGCGTTGAGTAATACCGTCTGCC/iSpC3//iSpC3/CA | 160 | 150 nM |
| rs10230708_rP | TAAGTGGAAAGAACTGGGGTGTC | 161 | 2.02 nM |
| rs10104396_rP | ACATGGTTAGATATTAGCCTGACCTATG | 162 | 3.71 nM |
| rs199032_rP | GCAGCCAAGTGTGAAAGTATTGA | 163 | 16.47 nM |
| rs926850_rP | TGATGTTGAGTTGAGACAGGTTACA | 164 | 13.99 nM |

TABLE 1-continued

Sequences and concentrations of forward primers (fP), blockers (B), and reverse primers (rP) used for the multiplex BDA experiments with results shown in FIGs. 4, 6, and 10. Note that the left panel of FIG. 4 did not use blockers.

| Name | Sequence | SEQ ID NO: | Conc. |
| --- | --- | --- | --- |
| rs17149369_rP | AAATGTAGTTCTATTATGGTCAGCACAC | 165 | 7.77 nM |
| rs869720_rP | AGTATCCCCAAAAGGTTGCAGAT | 166 | 6.23 nM |
| rs12478327_rP | GTGCAAGCTGGAGGCACT | 167 | 3.23 nM |
| rs2638145_rP | ACAGGAAAAGAAACTAAAATTGTACCCTT | 168 | 5.47 nM |
| rs2170091_rP | GAAGCCAGATCTCAAAGTGTCCT | 169 | 5.17 nM |
| rs2043583_rP | GTTATTGGGAATGCTATGAAAGAGACA | 170 | 7.73 nM |
| rs955456_rP | AGAACTCATTTCCTTATAGCTGAAGAACT | 171 | 30.06 nM |
| rs966516_rP | GCAGACACTTAGGATGTTTCCAGT | 172 | 2.61 nM |
| rs354169_rP | GAGCCTTAGTTCCTCCATCAGTAAA | 173 | 8.31 nM |
| rs1898170_rP | AAATTTACGTTGGTAATTGGGTCTTGT | 174 | 9.53 nM |
| rs11247921_rP | CACAGAGGTGACAGAACACAGT | 175 | 8.00 nM |
| rs1635718_rP | TAGTTATTCATGGTGGGAAGGCAA | 176 | 54.00 nM |
| rs10510620_rP | AAAAGATAATGTTCTTGTTTATATGCCCTTG | 177 | 6.34 nM |
| rs7104025_rP | TACAGCAACTCACAAACTAATGACTCT | 178 | 6.56 nM |
| rs2246745_rP | GGCTGCGATGAGACAGGAA | 179 | 3.68 nM |
| rs3789806_rP | AGGCACCAGAAGTCATCAGAATG | 180 | 9.35 nM |
| rs706714_rP | GACCAAGCTTTTATGCACCACA | 181 | 3.92 nM |
| rs1884444_rP | TGAAAGATAGCAATAGATACATAAAACACCA | 182 | 12.29 nM |
| rs2510152_rP | TGAAACCACATACACACAAATTCACT | 183 | 4.07 nM |
| rs16754_rP | CTTCCTGCTGTGCATCTGTAAGT | 184 | 16.06 nM |
| rs206781_rP | AAAAAGAAGAAACGGAAGGCAGAG | 185 | 20.05 nM |
| rs28932178_rP | TGCTGCCCCACCCTTTATTAAC | 186 | 2.38 nM |
| rs10186821_rP | CCTATTGGAAGAACCTGCCAGAA | 187 | 2.92 nM |
| rs10508599_rP | TGCAAAATGAAGCACAGCCC | 188 | 3.01 nM |
| rs10738578_rP | GCAGATGGAAAATACTTGGGAAAAAAAT | 189 | 21.81 nM |
| rs10741037_rP | GCAAAAATTACTATACCGACTTTAATAACGAAA | 190 | 27.73 nM |
| rs10770674_rP | ACTCATTGTAGGCTGAACCTTGG | 191 | 3.31 nM |
| rs10805227_rP | TGTATTGAGCATTTAGCACATGCC | 192 | 9.75 nM |
| rs10833604_rP | CAATTTCCAAGACAGAAGCACTCC | 193 | 15.58 nM |
| rs10964389_rP | ACTTACTGAGCACATGGCCTG | 194 | 2.20 nM |
| rs11015816_rP | GGAGAGGGTGAGAAGTTGCAC | 195 | 1.74 nM |
| rs11045749_rP | GGCAAAGACATTTTTCCAAGGAAGATAT | 196 | 4.40 nM |
| rs1123828_rP | CACTGCCAGCTTGTGCCT | 197 | 6.66 nM |
| rs11708584_rP | GCCCTAAATCCTAAATGAAATTGGCA | 198 | 2.97 nM |
| rs12192635_rP | AGAGGAGAAATAGATGTAGCTGCC | 199 | 1.96 nM |

TABLE 1-continued

Sequences and concentrations of forward primers (fP), blockers (B), and reverse primers (rP) used for the multiplex BDA experiments with results shown in FIGs. 4, 6, and 10. Note that the left panel of FIG. 4 did not use blockers.

| Name | Sequence | SEQ ID NO: | Conc. |
| --- | --- | --- | --- |
| rs12213948_rP | AATCCAGTGACATTCTTTAAACTGTCTT | 200 | 7.64 nM |
| rs12259813_rP | GCTGAGCTGTCACATCACTTCA | 201 | 2.72 nM |
| rs12541300_rP | GCTGTGTAGCTTGGCAAATTAACTA | 202 | 13.62 nM |
| rs12681931_rP | GCACTCTTGGGTAACAGGCTTT | 203 | 2.46 nM |
| rs12782580_rP | CCATGCCCAGCCTGGC | 204 | 4.03 nM |
| rs1375977_rP | TGGCTCCTCATAAGTTATGCAGATTT | 205 | 11.15 nM |
| rs1516755_rP | CAGTAGGATTGGCTTTATCAAAGAGATC | 206 | 56.85 nM |
| rs1524303_rP | ACCATAATGTTTTCCATAGAAGATGCAC | 207 | 18.98 nM |
| rs1667087_rP | GGTTCTGTACTGAAGTAAAAATCTCATACTAT | 208 | 30.60 nM |
| rs16871316_rP | GGCAAAGAAACATGGCAGAAATATCATA | 209 | 24.77 nM |
| rs16925478_rP | CCTTTGGCATTTTGGTCAAGATTGT | 210 | 13.76 nM |
| rs17560702_rP | GGGGGAAAATGGTTTCTTAGGATGA | 211 | 3.48 nM |
| rs1937037_rP | CTCCCATTTTTCTAAGACATTTTTTTTCTC | 212 | 9.86 nM |
| rs2215492_rP | AGCATGCCGCCCTTGG | 213 | 1.82 nM |
| rs2301720_rP | TCACAGGTCAAAATTATGAGTTCTTCG | 214 | 126.08 nM |
| rs2616187_rP | TGAGAGTGTGCAAGTCACTTGT | 215 | 12.88 nM |
| rs2710998_rP | GCAGGCAGCATGTATCCCAG | 216 | 4.92 nM |
| rs2807238_rP | GTTTAATGGACAGTAGATGCTAAATTCTAGA | 217 | 12.28 nM |
| rs2874755_rP | CGCCATAGTTAGCCGCTTCC | 218 | 3.33 nM |
| rs3813787_rP | TGAGCCTCGGTCTCTACCTG | 219 | 30.51 nM |
| rs4665582_rP | CCTTTAAGGCCCAGCAACTG | 220 | 3.56 nM |
| rs4712476_rP | GGGTGACCTTTCCCTTTTGATGA | 221 | 4.37 nM |
| rs611628_rP | TGTGTGTGAAAGCACTTTATAAACCA | 222 | 4.33 nM |
| rs6452035_rP | CTATCCTCAGAATTTTCCATTGATACTAGAAATA | 223 | 70.00 nM |
| rs6816854_fP | GAGTGTCTCCCAAACAAGGATCA | 224 | 126.08 nM |
| rs6937778_rP | ACAGCCATCAGATATCCAGCAG | 225 | 1.44 nM |
| rs7003044_rP | ACTTCGAGAATTGACTCTAAGTGGT | 226 | 4.68 nM |
| rs7032336_rP | AATTTAGCTTCCTTGAGGATAGAAGTAAC | 227 | 25.22 nM |
| rs7816009_rP | CCCGGCCACCCATACAG | 228 | 21.44 nM |
| rs7893462_rP | GAAAACTACCTAAACTATGTGAGAAAGAAC | 229 | 51.24 nM |
| rs7902135_rP | ACCCTCACTAATCTTTTCTGTTTGTTT | 230 | 3.01 nM |
| rs898476_rP | GTTTTTCTCCCAGCTGTAAAAGCA | 231 | 39.43 nM |
| rs9368431_rP | GCTTTAGTTTCTTTGCATATTTTCTGCAATA | 232 | 49.29 nM |
| rs9438621_rP | AGCTGATCTGCAAGGTCTATTTGA | 233 | 21.17 nM |
| rs9466035_rP | TGGGCTCAAGTGATCCACCTA | 234 | 2.93 nM |
| rs9466930_rP | GTAAAGAGAAGGGCTACCAGGATTA | 235 | 4.97 nM |

TABLE 1-continued

Sequences and concentrations of forward primers (fP), blockers (B), and reverse primers (rP) used for the multiplex BDA experiments with results shown in FIGs. 4, 6, and 10. Note that the left panel of FIG. 4 did not use blockers.

| Name | Sequence | SEQ ID NO: | Conc. |
|---|---|---|---|
| rs9973865_rP | CCCTATGCCTGGGATACTTCCTT | 236 | 17.08 nM |
| rs4712498_rP | ACAAATCTTTCATTTGTCTAAGGTATCAACT | 237 | 5.09 nM |
| rs2073149_rP | AGTGTCTTGCATTTTCAAGTATTCCT | 238 | 7.02 nM |
| rs2862909_rP | CCTAGGTTATTTGCTGTTCTCTTTCATTA | 239 | 4.55 nM |
| rs1338945_rP | GCTTGCATATAGACCTACAAATACCACT | 240 | 3.40 nM |

TABLE 2

Forward primers (fp) and reverse primers (rp) used for analysis of the SNP alleles of 23 individuals shown in FIG. 9. No blockers were used for this experiment.

| Name | Sequence | SEQ ID NO: | Conc. |
|---|---|---|---|
| rs10230708_fP | ACCAATGGGAGTCACTGCTG | 1 | 15 nM |
| rs10104396_fP | GAGGGGTATTAGAAGAATGACTATGTGA | 2 | 15 nM |
| rs199032_fP | GCTCTTCCTCTCACATCTTTATTTAACC | 3 | 15 nM |
| rs926850_fP | CAGAGTAAAATTTACTGCTCCGTCATAA | 4 | 15 nM |
| rs17149369_fP | GGATTCCCTAAGCTCTTCAATATTGC | 5 | 15 nM |
| rs869720_fP | CCTCATCTGTAAAGCAGGGAGAGA | 6 | 15 nM |
| rs12478327_fP | ACTTCTGCCAACATTCAAATTCAGG | 7 | 15 nM |
| rs2638145_fP | GGATGGGACTCCAATGCAAAACT | 8 | 15 nM |
| rs2170091_fP | CATCTTGCTCTTCATAGATAGCTTCAGA | 9 | 15 nM |
| rs2043583_fP | CCTGAATGTCAGTTTTGTTAGAGCAAC | 10 | 15 nM |
| rs955456_fP | CAGACTTAATCAAAGCCCTTGAAAAGA | 11 | 15 nM |
| rs966516_fP | CCTCCCATAGTGATTCTTATGAAGTCA | 12 | 15 nM |
| rs354169_fP | AATGCTTTGCTTGCTGAGAACTT | 13 | 15 nM |
| rs1898170_fP | AATGGGAAAACACATTTTAAGGGCA | 14 | 15 nM |
| rs11247921_fP | CCACACTCTGCCTCTCATGGTAT | 15 | 15 nM |
| rs10510620_fP | TCCGCAAAACCTACAATCTCTGAA | 17 | 15 nM |
| rs7104025_fP | TCAGATGCTTTAGGCTCATGAGTTA | 18 | 15 nM |
| rs2246745_fP | CTCCTTGGAATCACCAACAAACAT | 19 | 15 nM |
| rs3789806_fP | CTTGTATATAGACGGTAAAATAAACACCAAGA | 20 | 15 nM |
| rs706714_fP | TGAAGCAGATGTTGAACAACAAGG | 21 | 15 nM |
| rs1884444_fP | TTCCTGCTTCCAGACATGAATCA | 22 | 15 nM |
| rs2510152_fP | ACCCAGGTGAGTTTTGTTTCACAT | 23 | 15 nM |
| rs16754_fP | CTCTCTGCCTGCAGGATGTG | 24 | 15 nM |
| rs206781_fP | CACTTCCTCCAGAAGGTCCAAAG | 25 | 15 nM |

TABLE 2-continued

Forward primers (fp) and reverse primers (rp) used for analysis of the SNP alleles of 23 individuals shown in FIG. 9. No blockers were used for this experiment.

| Name | Sequence | SEQ ID NO: | Conc. |
|---|---|---|---|
| rs28932178_fP | ACTAAGAGTGCAGAGCCTGGAA | 26 | 15 nM |
| rs10186821_fP | GCGTTGTGCTGTCCATTGG | 27 | 15 nM |
| rs10508599_fP | GGGTTAAAATCTTTTGCTTTCATATTGAGC | 28 | 15 nM |
| rs10738578_fP | CCCGTTATATAAGAGGACATAATTGCAT | 29 | 15 nM |
| rs10741037_fP | CACTTTATCAGACACAGTTATGTGCT | 30 | 15 nM |
| rs10770674_fP | GCCCTATAGGTTTTCCTCCTACTGT | 31 | 15 nM |
| rs10805227_fP | CTATCTGCAGGATTGTGTTCAATGTA | 32 | 15 nM |
| rs10833604_fP | CTCTCTAGAGTGCAGATTGGTAGAA | 33 | 15 nM |
| rs10964389_fP | CAAAGTTGATAAATTAAAGGACTAAGGCAC | 34 | 15 nM |
| rs11015816_fP | CTGACCTAAGGCATGGGACTT | 35 | 15 nM |
| rs11045749_fP | CATTCTGTCTGGGATGAGGTGAT | 36 | 15 nM |
| rs1123828_fP | TGGAATCAAACATACTATGTGTCAAACA | 37 | 15 nM |
| rs11573214_fP | GGCACCATGCATCCAGCC | 241 | 15 nM |
| rs11708584_fP | GCGAAGTCATTTCGGTCCTCTTTAA | 38 | 15 nM |
| rs12192635_fP | CCTCTGATTCCCAGACATAATGCT | 39 | 15 nM |
| rs12213948_fP | TGAAAGACGTCACAGCAAGGT | 40 | 15 nM |
| rs12259813_fP | TGTAGGAGAGATTGGGCTAGAGAG | 41 | 15 nM |
| rs12541300_fP | ACAGAAACCAATTACCTATGAGGAGTAA | 42 | 15 nM |
| rs12681931_fP | GAAAGTGGCACAGAAACTCAGAC | 43 | 15 nM |
| rs12782580_fP | GCATTAGATCATTTAACACACAAAACCCTAT | 44 | 15 nM |
| rs1375977_fP | TGCTCCTAAAAGCACCCAGC | 45 | 15 nM |
| rs1516755_fP | CTAACTTCCTAACTAAAACTTTACAGTGGA | 46 | 15 nM |
| rs1524303_fP | GGATTTCACACCCATTAGAATAACTACTAT | 47 | 15 nM |
| rs1667087_fP | CCTCTAGAAAAAATGGAGATTTGGGAAT | 48 | 15 nM |
| rs16871316_fP | GGACTTTTTGCTTTTGACACCTTTAC | 49 | 15 nM |
| rs16925478_fP | ACGTATTTCTAACTATAGTGAGTGCATTATG | 50 | 15 nM |
| rs17560702_fP | ACATGTCCAAAGAGAGAAGTCGTAG | 51 | 15 nM |
| rs1937037_fP | GCACGTAGATGAAATTGCCCCATA | 52 | 15 nM |
| rs2215492_fP | GCCCCAAAGGTTACCCCATG | 53 | 15 nM |
| rs2616187_fP | GGAAAATATGTCTAAAAAGGCTCTGGAG | 55 | 15 nM |
| rs2710998_fP | GTTTGTTCTAAGGTTCATCTGGTGAT | 56 | 15 nM |
| rs2807238_fP | GTGGGCTTACATGATTGGATTAACTT | 57 | 15 nM |
| rs2874755_fP | TGTCCCACTTTTTACCTCCCTTC | 58 | 15 nM |
| rs4665582_fP | TGTGCTACGACAGAGCTAAGTAC | 60 | 15 nM |
| rs4712476_fP | CCCCGGATGTCAGGGAATG | 61 | 15 nM |
| rs611628_fP | CCAGGCACCACTGCTTTGT | 62 | 15 nM |
| rs6452035_fP | GCAGAAAAAAATGATATCTGAATTCTGGAT | 63 | 15 nM |

TABLE 2-continued

Forward primers (fp) and reverse primers (rp) used for analysis of the SNP alleles of 23 individuals shown in FIG. 9. No blockers were used for this experiment.

| Name | Sequence | SEQ ID NO: | Conc. |
|---|---|---|---|
| rs6816854_fP | CCTTTTTCACTGTTATGAAATGTACTTTCTT | 64 | 15 nM |
| rs6937778_fP | AGGATGCTGGGGCTTGC | 65 | 15 nM |
| rs7003044_fP | GTAAAGTGCATGGGGTCAAGTC | 66 | 15 nM |
| rs7032336_fP | TGAGAAGTCTAACAAGTTAAATTCAGGAC | 67 | 15 nM |
| rs7816009_fP | GGTAGAATGTTAGTGACTATGTACAATTTCA | 68 | 15 nM |
| rs7893462_fP | ACCTTGTCAAGAACCTAAATAGTGAGAA | 69 | 15 nM |
| rs7902135_fP | CGTGGGCTAGTCAAGAATATAAAATGTTAG | 70 | 15 nM |
| rs898476_fP | CCTATATAGACTAATTTACTTAAACATTTAACCCCA | 71 | 15 nM |
| rs9368431_fP | GGTTCAACTCTCAGTTTTATTAGTTGTGT | 72 | 15 nM |
| rs9438621_fP | AGCATCGTGAGGTTCTGAAAAGA | 73 | 15 nM |
| rs9466035_fP | CCTAACACCAGTTCTTCCTCCAC | 74 | 15 nM |
| rs9466930_fP | TGTGTGGCTCAGTATACCACTTAG | 75 | 15 nM |
| rs9973865_fP | GAAAW1GGGTCTCATTAGGATCATTAC | 76 | 15 nM |
| rs4712498_fP | GTTTTTATATGTTAGTGTCCCCATGGTATA | 77 | 15 nM |
| rs2862909_fP | GCACATCATACATTATTTCTGTTGCTAT | 79 | 15 nM |
| rs1338945_fP | GAAATATTGCTGGGGTCAGCG | 80 | 15 nM |
| rs2301720_fP | GTAGCCGCTTCTCTGTGAGTT | 54 | 15 nM |
| rs955429_fP | GTCCAAGAGTGGAGGATTGGG | 242 | 15 nM |
| rs12095834_fP | GGAAATCGTACAGTTCCAAAGTACAA | 243 | 15 nM |
| rs10829268_fP | ACAGCAACAGAAACTACCCAAAAG | 244 | 15 nM |
| rs1635718_fP | ACTTAAGAGGTCAACACAGATGAAAATTATC | 16 | 15 nM |
| rs2073149_fP | AGTGATCAGAAGGCTTTGATTTGA | 78 | 15 nM |
| rs9358720_fP | CAAGCATCTTCTCCTTCCTCTCT | 245 | 15 nM |
| rs3813787_fP | GGGCTTCGGAATCGGACTTG | 59 | 15 nM |
| rs10230708_rP | TAAGTGGAAAGAACTGGGGTGTC | 161 | 15 nM |
| rs10104396_rP | ACATGGTTAGATATTAGCCTGACCTATG | 162 | 15 nM |
| rs199032_rP | GCAGCCAAGTGTGAAAGTATTGA | 163 | 15 nM |
| rs926850_rP | TGATGTTGAGTTGAGACAGGTTACA | 164 | 15 nM |
| rs17149369_rP | AAATGTAGTTCTATTATGGTCAGCACAC | 165 | 15 nM |
| rs869720_rP | AGTATCCCCAAAAGGTTGCAGAT | 166 | 15 nM |
| rs12478327_rP | GTGCAAGCTGGAGGCACT | 167 | 15 nM |
| rs2638145_rP | ACAGGAAAAGAAACTAAAATTGTACCCTT | 168 | 15 nM |
| rs2170091_rP | GAAGCCAGATCTCAAAGTGTCCT | 169 | 15 nM |
| rs2043583_rP | GTTATTGGGAATGCTATGAAAGAGACA | 170 | 15 nM |
| rs955456_rP | AGAACTCATTTCCTTATAGCTGAAGAACT | 171 | 15 nM |
| rs966516_rP | GCAGACACTTAGGATGTTTCCAGT | 172 | 15 nM |

TABLE 2-continued

Forward primers (fp) and reverse primers (rp) used
for analysis of the SNP alleles of 23 individuals shown in
FIG. 9. No blockers were used for this experiment.

| Name | Sequence | SEQ ID NO: | Conc. |
|---|---|---|---|
| rs354169_rP | GAGCCTTAGTTCCTCCATCAGTAAA | 173 | 15 nM |
| rs1898170_rP | AAATTTACGTTGGTAATTGGGTCTTGT | 174 | 15 nM |
| rs11247921_rP | CACAGAGGTGACAGAACACAGT | 175 | 15 nM |
| rs10510620_rP | AAAAGATAATGTTCTTGTTTATATGCCCTTG | 177 | 15 nM |
| rs7104025_rP | TACAGCAACTCACAAACTAATGACTCT | 178 | 15 nM |
| rs2246745_rP | GGCTGCGATGAGACAGGAA | 179 | 15 nM |
| rs3789806_rP | AGGCACCAGAAGTCATCAGAATG | 180 | 15 nM |
| rs706714_rP | GACCAAGCTTTTATGCACCACA | 181 | 15 nM |
| rs1884444_rP | TGAAAGATAGCAATAGATACATAAAACACCA | 182 | 15 nM |
| rs2510152_rP | TGAAACCACATACACACAAATTCACT | 183 | 15 nM |
| rs16754_rP | CTTCCTGCTGTGCATCTGTAAGT | 184 | 15 nM |
| rs206781_rP | AAAAAGAAGAAACGGAAGGCAGAG | 185 | 15 nM |
| rs28932178_rP | TGCTGCCCCACCCTTTATTAAC | 186 | 15 nM |
| rs10186821_rP | CCTATTGGAAGAACCTGCCAGAA | 187 | 15 nM |
| rs10508599_rP | TGCAAAATGAAGCACAGCCC | 188 | 15 nM |
| rs10738578_rP | GCAGATGGAAAATACTTGGGAAAAAAAT | 189 | 15 nM |
| rs10741037_rP | GCAAAAATTACTATACCGACTTTAATAACGAAA | 190 | 15 nM |
| rs10770674_rP | ACTCATTGTAGGCTGAACCTTGG | 191 | 15 nM |
| rs10805227_rP | TGTATTGAGCATTTAGCACATGCC | 192 | 15 nM |
| rs10833604_rP | CAATTTCCAAGACAGAAGCACTCC | 193 | 15 nM |
| rs10964389_rP | ACTTACTGAGCACATGGCCTG | 194 | 15 nM |
| rs11015816_rP | GGAGAGGGTGAGAAGTTGCAC | 195 | 15 nM |
| rs11045749_rP | GGCAAAGACATTTTTCCAAGGAAGATAT | 196 | 15 nM |
| rs1123828_rP | CACTGCCAGCTTGTGCCT | 197 | 15 nM |
| rs11573214_rP | CCTAGTCCTTAACCACTCCTTACAG | 246 | 15 nM |
| rs11708584_rP | GCCCTAAATCCTAAATGAAATTGGCA | 198 | 15 nM |
| rs12192635_rP | AGAGGAGAAATAGATGTAGCTGCC | 199 | 15 nM |
| rs12213948_rP | AATCCAGTGACATTCTTTAAACTGTCTT | 200 | 15 nM |
| rs12259813_rP | GCTGAGCTGTCACATCACTTCA | 201 | 15 nM |
| rs12541300_rP | GCTGTGTAGCTTGGCAAATTAACTA | 202 | 15 nM |
| rs12681931_rP | GCACTCTTGGGTAACAGGCTTT | 203 | 15 nM |
| rs12782580_rP | CCATGCCCAGCCTGGC | 204 | 15 nM |
| rs1375977_rP | TGGCTCCTCATAAGTTATGCAGATTT | 205 | 15 nM |
| rs1516755_rP | CAGTAGGATTGGCTTTATCAAAGAGATC | 206 | 15 nM |
| rs1524303_rP | ACCATAATGTTTTCCATAGAAGATGCAC | 207 | 15 nM |
| rs1667087_rP | GGTTCTGTACTGAAGTAAAAATCTCATACTAT | 208 | 15 nM |

TABLE 2-continued

Forward primers (fp) and reverse primers (rp) used for analysis of the SNP alleles of 23 individuals shown in FIG. 9. No blockers were used for this experiment.

| Name | Sequence | SEQ ID NO: | Conc. |
|---|---|---|---|
| rs16871316_rP | GGCAAAGAAACATGGCAGAAATATCATA | 209 | 15 nM |
| rs16925478_rP | CCTTTGGCATTTTGGTCAAGATTGT | 210 | 15 nM |
| rs17560702_rP | GGGGGAAAATGGTTTCTTAGGATGA | 211 | 15 nM |
| rs1937037_rP | CTCCCATTTTTCTAAGACATTTTTTTTCTC | 212 | 15 nM |
| rs2215492_rP | AGCATGCCGCCCTTGG | 213 | 15 nM |
| rs2616187_rP | TGAGAGTGTGCAAGTCACTTGT | 215 | 15 nM |
| rs2710998_rP | GCAGGCAGCATGTATCCCAG | 216 | 15 nM |
| rs2807238_rP | GTTTAATGGACAGTAGATGCTAAATTCTAGA | 217 | 15 nM |
| rs2874755_rP | CGCCATAGTTAGCCGCTTCC | 218 | 15 nM |
| rs4665582_rP | CCTTTAAGGCCCAGCAACTG | 220 | 15 nM |
| rs4712476_rP | GGGTGACCTTTCCCTTTTGATGA | 221 | 15 nM |
| rs611628_rP | TGTGTGTGAAAGCACTTTATAAACCA | 222 | 15 nM |
| rs6452035_rP | CTATCCTCAGAATTTTCCATTGATACTAGAAATA | 223 | 15 nM |
| rs6816854_rP | GAGTGTCTCCCAAACAAGGATCA | 224 | 15 nM |
| rs6937778_rP | ACAGCCATCAGATATCCAGCAG | 225 | 15 nM |
| rs7003044_rP | ACTTCGAGAATTGACTCTAAGTGGT | 226 | 15 nM |
| rs7032336_rP | AATTTAGCTTCCTTGAGGATAGAAGTAAC | 227 | 15 nM |
| rs7816009_rP | CCCGGCCACCCATACAG | 228 | 15 nM |
| rs7893462_rP | GAAAACTACCTTAAACTATGTGAGAAAGAAC | 229 | 15 nM |
| rs7902135_rP | ACCCTCACTAATCTTTTCTGTTTGTTT | 230 | 15 nM |
| rs898476_rP | GTTTTTCTCCCAGCTGTAAAAGCA | 231 | 15 nM |
| rs9368431_rP | GCTTTAGTTTCTTTGCATATTTTCTGCAATA | 232 | 15 nM |
| rs9438621_rP | AGCTGATCTGCAAGGTCTATTTGA | 233 | 15 nM |
| rs9466035_rP | TGGGCTCAAGTGATCCACCTA | 234 | 15 nM |
| rs9466930_rP | GTAAAGAGAAGGGCTACCAGGATTA | 235 | 15 nM |
| rs9973865_rP | CCCTATGCCTGGGATACTTCCTT | 236 | 15 nM |
| rs4712498_rP | ACAAATCTTTCATTTGTCTAAGGTATCAACT | 237 | 15 nM |
| rs2862909_rP | CCTAGGTTATTGCTGTTCTCTTTCATTA | 239 | 15 nM |
| rs1338945_rP | GCTTGCATATAGACCTACAAATACCACT | 240 | 15 nM |
| rs2301720_rP | TCACAGGTCAAAATTATGAGTTCTTCG | 214 | 15 nM |
| rs955429_rP | TCCAAACTGGAAATGGCTGTATCT | 247 | 15 nM |
| rs12095834_rP | GCTTTCTATTTATTTAAAAGAAAGTGAAGTCCC | 248 | 15 nM |
| rs10829268_rP | TTTCCCCCCTTCTCTCTTCTTTTT | 249 | 15 nM |
| rs1635718_rP | TAGTTATTCATGGTGGGAAGGCAA | 176 | 15 nM |
| rs2073149_rP | AGTGTCTTGCATTTTCAAGTATTCCT | 238 | 15 nM |

TABLE 2-continued

Forward primers (fp) and reverse primers (rp) used for analysis of the SNP alleles of 23 individuals shown in FIG. 9. No blockers were used for this experiment.

| Name | Sequence | SEQ ID NO: | Conc. |
|---|---|---|---|
| rs9358720_rP | CAGCAGTACACTGAACAGAATCC | 250 | 15 nM |
| rs3813787_rP | TGAGCCTCGGTCTCTACCTG | 219 | 15 nM |

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method for simultaneously amplifying and detecting allelic variants at at least ten genetic loci, the method comprising:
   (a) mixing a sample comprising DNA with a DNA polymerase and a blocker displacement amplification (BDA) oligo set for each genetic locus, each BDA oligo set comprising (i) a BDA forward primer, (ii) a BDA blocker, and (iii) a BDA reverse primer, wherein at least four nucleotides at the 3' end of each BDA forward primer sequence are also present at or near the 5' end of its respective BDA blocker sequence, wherein each BDA blocker contains a 3' sequence or modification that prevents extension by DNA polymerase, and wherein the concentration of each BDA blocker is at least twice that of its respective BDA forward primer; and
   (b) subjecting the mixture to at least four cycles of amplification, thereby producing amplicons;
   (c) performing next-generation sequencing (NGS) of the amplicons.

2. The method of claim 1, wherein the DNA polymerase has 3' to 5' exonuclease activity.

3. The method of claim 2, wherein each BDA blocker has a 3' modification that prevents 3' to 5' exonuclease activity.

4. The method of claim 1, wherein the concentration of each BDA reverse primer and/or each BDA forward primer is determined based on a reads analysis of a previous calibration NGS experiment, wherein the concentration of each BDA reverse primer and/or each BDA forward primer is increased relative to the concentration used for the previous calibration NGS experiment.

5. The method of claim 4, wherein the concentration of each BDA reverse primer follows a formula: [rP]new=[rP]old * (Reads_median/Reads_amplicon)^X, where [rP]old is the previous concentration of the reverse primer, Reads_median is the median reads mapped to each amplicon, Reads_amplicon is the reads mapped to the amplicon corresponding to said reverse primer, and X is an adjustment factor between 0.25 and 1.

6. The method of claim 4, wherein the concentration of each BDA forward primer follows a formula: [fP]new=[fP]old * (Reads_median/Reads_amplicon)^X, where [fP]old is the previous concentration of the forward primer, Reads_median is the median reads mapped to each amplicon, Reads_amplicon is the reads mapped to the amplicon corresponding to said forward primer, and X is an adjustment factor between 0.25 and 1.

7. The method of claim 1, wherein the BDA oligo set comprises at least 10 BDA oligo sets, each BDA oligo set comprising (i) a BDA forward primer, (ii) a BDA blocker, and (iii) a BDA reverse primer, wherein at least four nucleotides at the 3' end of each BDA forward primer sequence are also present at or near the 5' end of its corresponding BDA blocker sequence, wherein each BDA blocker contains a 3' sequence or modification that prevents extension by DNA polymerase, and wherein the concentration of each BDA blocker is at least twice that of its corresponding BDA forward primer, wherein each BDA blocker is complementary to a genomic region bearing a single nucleotide polymorphism (SNP) in which the alternative allele has a population frequency of between 10% and 90%, and wherein each corresponding BDA forward primer is not complementary to the SNP locus.

8. The method of claim 7, wherein none of the BDA forward primers and none of the BDA reverse primers are complementary to any SNP in which the alternative allele has a population frequency of over 1%.

9. The method of claim 7, wherein the genomic position that each BDA reverse primer binds is located between 100 nt and 500 nt away from the genomic position that its corresponding BDA forward primer binds.

10. The method of claim 7, wherein the calculated $\Delta G°$'s for each BDA forward primer binding to its corresponding complement are all within 2 kcal/mol of each other at 60° C. in 0.18 M $Na^+$.

11. The method of claim 7, wherein the calculated $\Delta G°$ for each BDA blocker binding to its corresponding complement is between 0.5 kcal/mol and 3.5kcal/mol more favorable than the $\Delta G°$ of binding between the corresponding BDA forward primer and its complement at 60° C. in 0.18 M $Na^+$.

12. A method for detecting contamination of a base cell line, the method comprising:
 (a) extracting genomic DNA from a cell sample;
 (b) producing and detecting amplicons according to the method of claim 1
 (c) further detecting contamination, wherein the further detecting comprises identifying the presence of amplicons that are not amplicons from the base cell line.

* * * * *